(12) United States Patent
Vinetz

(10) Patent No.: US 6,815,183 B1
(45) Date of Patent: Nov. 9, 2004

(54) PLASMODIUM SP. CHITINASE

(75) Inventor: Joseph M. Vinetz, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 09/579,383

(22) Filed: May 26, 2000

Related U.S. Application Data

(60) Provisional application No. 60/136,508, filed on May 28, 1999, and provisional application No. 60/180,051, filed on Feb. 3, 2000.

(51) Int. Cl.[7] .................. C12N 15/09; C12N 15/30; C07H 21/04; A61K 39/015; A61K 39/002
(52) U.S. Cl. .................. 435/69.3; 435/243; 435/320.1; 435/69.7; 435/70.1; 435/71.1; 424/191.1; 424/268.1; 424/272.1; 536/23.1; 536/23.5; 536/23.7
(58) Field of Search .................. 536/23.5, 23.1, 536/23.7; 424/191.1, 268.1, 272.1; 435/243, 320.1, 325, 455, 471, 69.3, 69.7, 70.1, 71.1

(56) References Cited

U.S. PATENT DOCUMENTS

| | | |
|---|---|---|
| 5,783,431 A | 7/1998 | Peterson et al. |
| 5,824,485 A | 10/1998 | Thompson et al. |

OTHER PUBLICATIONS

Boehringer Mannheim Biochemicals (1991 Catalog p. 557).*
Stratagene (1991 Product Catalog, p. 66).*
Gibco BRL (Catalogue & Reference Guide 1992, p. 292).*
Promega (1993/1994 Catalog, pp. 90–91) or New England BioLabs (Catalog 1986/1987, pp. 60–62).*
Bowie et al. Science, vol. 247: 1990; p. 1306; p. 1308.*
Sim et al 1989 (Molecular and Biochemical Parasitology: 34:127–134).*
Vinetz et al 1999(PNAS: 96: 14061–14066).*
Marra et al. , The WashU–HHmi Mouse EST Project (Sep. 12, 1996).
Vinetz et al., J. Biol. Chem., 275(14):10331–10341(2000).
Vinetz et al., Experimental Parasitology, 90:199–202(1998).
Duffy et al., Infection and Immunity, 65(3):1109–1113(1997).
Shahabuddin et al., Proc. Natl. Acad. Sci. USA, 90:4266–4270(1993).
Shahabuddin et al., Experimental Parasitology, 79:85–88 (1994).
Huber et al., Proc. Natl. Acad. Sci. USA, 88:2807–2810(1991).
Wagner et al., Nature Biotech., 14:840–844(1996).

* cited by examiner

Primary Examiner—Lynette R. F. Smith
Assistant Examiner—Padma Baskar
(74) Attorney, Agent, or Firm—Rogalskyj & Weyand, LLP

(57) ABSTRACT

The present invention is directed to isolated nucleic acid molecules encoding *Plasmodium* sp. *chitinases*. Expression vectors and host cells comprising the nucleic acid molecules are also provided, as well as methods for increasing or decreasing the expression of the *chitinase* in host cells. The invention further provides methods of screening a substance for the ability of the substance to modify *chitinase* function, and a method for isolating other *chitinase* molecules. DNA oligomers capable of hybridizing to the nucleic acid molecule encoding the *chitinase* are provided, which can be used to detect *chitinase* in a sample. An isolated *Plasmodium* sp. *chitinase* is also provided. Antibodies specific for the *chitinase*, and fragments thereof, are provided, as are compositions comprising the *chitinase* and a compatible carrier. The subject invention further provides methods of preventing infection of mosquitoes by *Plasmodium* sp. and methods of preventing transmission of malaria.

9 Claims, 17 Drawing Sheets

MNFKISIFLLIYSILYSANSRDLKGKNNINNSLGIIRENKNKTHQTEIHE  50

SFSHLKSNNSNFYEYGSYCGDGCNSRITKNNKNINKNDRKPRQILEEYK  100
          N-terminal 1      N-terminal 2

KRKQGIIAGYYGSWNSQGDRAKHMIDSNPHVSILYIAFARINHLYDVSRP  150

Substrate binding site
FNGRQRFLLRKHGLEYETYGMHLNEIRRIRKVRPQVILLSLGGETYMID  200
                    Active site peptide
IEKEIDYVDKILKLVNDXXXXXXXXXXHGKFYNLNELNFSNYYIKLIN  250
                  Catalytic active site

LLRKTIPEEKLISISGSSNAALSCYSGVASFCKDEESPYNTKFLSEQIET  300

NKELHRAAAMLSAGTFINIFNTAKEKIDLVFIQTYNLETTNPDIMVDHYL  350

SHLYFGLKYNITIILGFSLEHNRGGFSPENKELLELVGKTIHDKNQNNNR  400

AQGIGIWHLFMKEQLPTGSFDVDIFLTNIWKHLNPEVQTPKDLTITENPE  450
                                GT33

QCSTIDEYVPGLVIPTIGIYYKHNDAIWKTRSYSIHAPGVQRYEWDLVKY  500
                 C-terminus peptide
CYEKICQGKAAHYINIDYKESSIIIWKGEPYLIKWQQGPPEGQALESYT  550
              GT29

KLDASKCPGIEEWNKKTPHKPLEVEEQYEQEVDLPLQ*            587
              GT34

```
PfCHT1    MNFTVKYSPLVICLLGCLLSTYVSVIEG------------------------------   28
                 Pro-enzyme domain
PgCHT1    MNIKISIFLIIVSILVSANSRT------LKGRNNINNSLGIRENKNITHQTEIHRSPSHLKSNNSNEVE   64
                                                    Catalytic domain begins
PfCHT1    HRARPGESR------------KN------------PRBIIKTPICBSGKGIIQGYYPSMVSYNRNLKDL-   72
                                                                            Substrate-binding
                                                                                 site
PgCHT1    ------YGSYCGDGCNSRITQNMNINTNQNDRKSPRQILEYTGKRKQGIIAGTYGSWNSQQDRAKGBMI  125
                 NT1              NT2
PfCHT1    --NPNLNVVHMSPAKQDLSYDSIBSIVGSPLLPKSLIGLEYIGLNBYPNDAMNLRKIARPDIIMLLSLGGE  140
PgCHT1    DSNPMVSILYIAPARINMLYDVSRPPNGRQRFLLRKHGLEYETYGMMLNEIRIRKVRPDVIILLSLGGE  195
                 Active site
PfCHT1    TYHPSSPDSALNAVBKIANLVDBLGPDGIDVDYBPNGSPTGLNDEEKADFFVQYVTKLREYMCDDKLISI  210
PgCHT1    TYM-IDIBKEIDYVDKILKLVNDPDLDGVDIDMEPHGKPYNLNELNFSNYYIKLINLLRKTIPBEKLISI  264
PfCHT1    SQSSNGALSCI-GPNDPKKICHDDBAPYNSKYPNKP-DVKKBLLRAACMASAGGAIYLMNLKMHIDMVP  278
PgCHT1    SGSSNAALSCVSGVAS---PCKQBBSPYNTKPLSBQIBTNKBLHKAAAMLSAGTPININFNTAKEKIDLVF  331
PfCHT1    VQTPNYTNSTDSTVMKBLYDSYAYYGKKYDYVIIMGPTTLMFPSTPPNPNDKMLVKSIQDPVKTENKLMKR  348
PgCHT1    IQTYNL-BTTNPDIMVDMYLSHLYPGLKYNITITIILGFSLBHNRGGPSPENKELLELVGKTIHDKNQNNMR  400
              Catalytic domain ends                                  Chitin-binding domain
                                                                           begins
PfCHT1    ADGFGLMSLSSDNAARNBQLAIEYPVBSLH. 378
PgCHT1    ADGIGIMHLPMKBQLPTGSPDVDIPLTNIMKHLNPEVQTPKQLTITBNPEDCSTIDBYVPGLVIPTIGIN  470
PgCHT1    DYYKHAIWKTRSYSIHABPGVDRYBMDLVKVCYBKICDGKAAHYYNTDYKBSSIIIWKGBPYLIKWMQQGP  540
PgCHT1    PBGQALBSYTTKLDASKCPGIBEMNTKYPHKPLBVEBQYBQEVDLPLQ. 587
```

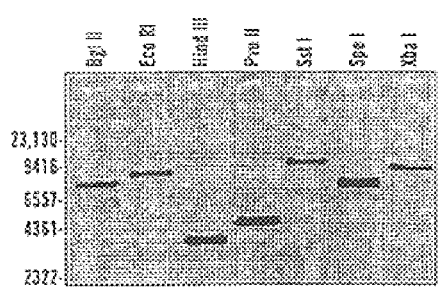 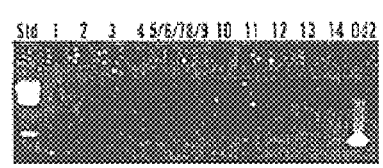 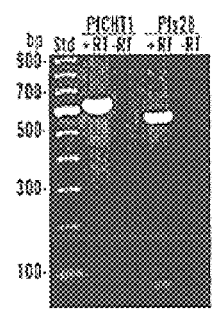
*FIG. 12A*                *FIG. 12B*                *FIG. 12C*

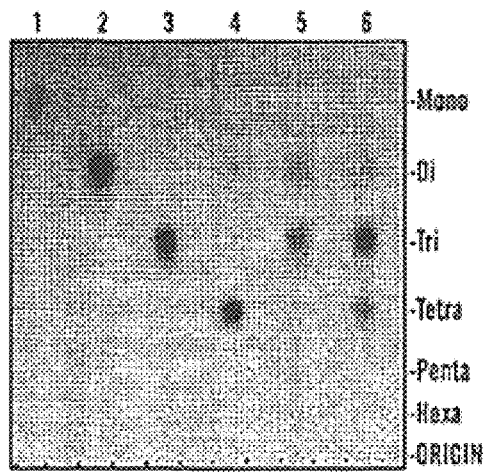 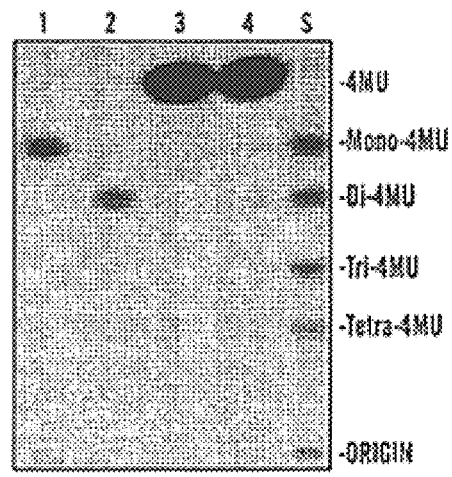
*FIG. 14A*     *FIG. 14B*
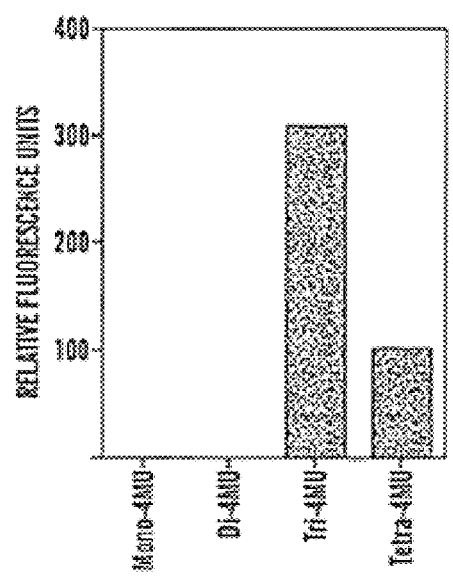
*FIG. 14C*

PLASMODIUM SP. CHITINASE

This application claims priority of U.S. Provisional Patent Application No. 60/136,508, filed May 28, 1999, and of U.S. Provisional Patent Application No. 60/180,051, filed Feb. 3, 2000.

FIELD OF THE INVENTION

The present invention relates generally to a parasite protein, and more particularly to *Plasmodium* sp. *chitinase* and uses thereof.

BACKGROUND OF THE INVENTION

Throughout this application various publications are referenced, many in parenthesis. Full citations for each of these publications are provided at the end of the Detailed Description and throughout the Detailed Description. The disclosures of each of these publications in their entireties are hereby incorporated by reference in this application.

Defining molecular targets for drug or vaccine intervention remains a key strategy for developing new ways to prevent and treat malaria, a disease that exacts an enormous social and economic toll worldwide. A number of investigators have proposed transmission-blocking vaccines as one component of an overall program of malaria control (Kaslow 1997). Such vaccines are designed to induce antibodies in humans that, when ingested by the mosquito along with a *Plasmodium*-containing blood meal, interfere with the development of the parasite within the mosquito midgut. Animal models of transmission-blocking vaccines, based primarily on two *P. falciparum* zygote/ookinete surface proteins, Pfs25 and Pfs28, have demonstrated proof of principle (Gozar et al. 1998), but results of human clinical trials have not been reported to date.

A *Plasmodium* ookinete-secreted enzyme, *chitinase* (E.C. 3.2.1.14), has been demonstrated to be another target of blocking malaria transmission from humans to mosquitoes (Shahabuddin et al. 1993). *Chitinases* are found in prokaryotes and eukaryotes (Flach et al. 1992); their biologic roles include cell wall modification (e.g. fungi (Kuranda and Robbins 1991), Entamoebae (Willagomez-Castro et al. 1992) and filaria parasites (Fuhrman and Piessens 1985)), carbon source degradation (e.g. *Streptomyces* spp. (Ni and Westpheling 1997; Robbins et al. 1988), *Serratia marcescens* (Roberts and Cabib 1982), and *Vibrio* spp. (Keyhani and Roseman 1996)), and plant and fungal host defense against chitin-containing pathogens (Flach et al. 1992). One other protozoan pathogen of man, *Leishmania donovani*, the agent of human visceral leishmaniasis, is known to use a *chitinase* in its life cycle (Schlein et al. 1991; Shakarian and Dwyer 1998). The *Leishmania chitinase* is thought to disrupt the sand fly cardiac valve, allowing amastigotes to be regurgitated from the midgut into the skin of the vertebrate host. The *Leishmania chitinase* is not thought to function in invasion of the arthropod vector per-se (Schlein et al. 1992). In contrast, *Plasmodium chitinase* is thought to be required for the parasite to invade the mosquito midgut after being taken up in a blood meal (Shahabuddin et al. 1993). Because of its critical biological function in the life cycle of the malaria parasite, the *Plasmodium chitinase* is a potential target for blocking transmission from the vertebrate host to the mosquito vector (Shahabuddin et al. 1993).

The potential importance of *chitinase* in malaria parasite biology was first suggested by a transmission electron micrograph showing the *P. gallinaceum* ookinete penetrating and appearing to focally degrade the chitinous peritrophic matrix (PM) in the *Aedes aegypti* midgut (Sieber et al. 1991). The PMs of the *Plasmodium* vectors *Anopheles gambiae* (which carries human malaria parasites) and *A. aegypti* (which carries avian malaria parasites) are composed of chitin, a β-1,4-linked polymer of GlcNAc, with intercalated proteins including trypsins and peritrophins (Perrone and Spielman 1988; Shen and Jacobs-Lorena 1997; Shen and Jacobs-Lorena 1998). *P. gallinaceum* ookinetes secrete active *chitinase* (Huber et al. 1991; Vinetz and Kaslow 1998). Although *chitinases* are found throughout the prokaryote and eukaryote kingdoms, the biological function of *Plasmodium chitinases* must be different, because ookinetes do not contain chitin and there is no evidence that ookinetes use chitin or mono- or oligomers of GlcNAc as a carbon source. *Chitinases* are critical for allowing the parasite to escape the mosquito midgut, as evidenced by the observation that addition of the *chitinase* inhibitor allosamidin to a blood meal prevents oocyst development (Shahabuddin et al. 1993). Both *P. gallinaceum* in *A. aegypti* and *P. falciparum* in *A. freeborni* fail to develop into oocysts in the presence of this inhibitor. This effect could be completely reversed by enzymatic degradation of the peritrophic matrix (PM) in vivo, by adding exogenous *chitinase* to the blood meal. These observations demonstrated that a *chitinase* is necessary for malaria parasites to invade the mosquito and initiate sporogonic development.

Because of intrinsic biologic interest and the potential for *Plasmodium chitinases* to be targets of interfering with malaria transmission (for a review of malaria transmission-blocking vaccines and the potential of *Plasmodium chitinases* as targets, see: Kaslow 1993; Shahabuddin and Kaslow 1993), a need exists for the identification of the malarial parasite *chitinase*.

SUMMARY OF THE INVENTION

To this end, the subject invention provides an isolated nucleic acid molecule encoding a *Plasmodium* sp. *chitinase*. The invention also provides an oligonucleotide complementary to at least a portion of the mRNA encoding the *Plasmodium* sp. *chitinase*.

The isolated nucleic acid molecules of the invention can be inserted into suitable expression vectors and/or host cells. Expression of the nucleic acid molecules encoding the *Plasmodium* sp. *chitinase* results in production of *Plasmodium* sp. *chitinase* in a host cell. Expression of the oligonucleotide in a host cell results in decreased expression of the *Plasmodium* sp. *chitinase*.

The invention further provides methods of screening a substance for the ability of the substance to modify *Plasmodium* sp. *chitinase* function, and a method of obtaining DNA encoding a *Plasmodium* sp. *chitinase*.

Further provided is an isolated nucleic acid molecule encoding a *Plasmodium* sp. *chitinase*, wherein the nucleic acid molecule encodes a first amino acid sequence having at least 90% amino acid identity to a second amino acid sequence. The second amino acid sequence is as shown in SEQ ID NO:3 or SEQ ID NO:4.

The invention further provides a DNA oligomer capable of hybridizing to a nucleic acid molecule encoding a *Plasmodium* sp. *chitinase*. The DNA oligomer can be used in a method of detecting presence of a *Plasmodium* sp. *chitinase* in a sample, which method is also provided by the subject invention.

The invention also provides an isolated *Plasmodium* sp. *chitinase*, a composition thereof, and antibodies or antibody fragments specific for the *Plasmodium* sp. *chitinase*. The antibodies and antibody fragments can be used to detect the presence of the *Plasmodium* sp. *chitinase* in samples. The subject invention further provides a method of producing an antibody specific for a *Plasmodium* sp. *chitinase* in a host. The method comprises selecting the isolated *Plasmodium* sp. *chitinase* or an antigenic portion thereof and introducing the selected *Plasmodium* sp. *chitinase* or antigenic portion thereof into a host to induce production of an antibody specific for *Plasmodium* sp. *chitinase* in the host. Further provided is an isolated *Plasmodium* sp. *chitinase* encoded by a first amino acid sequence having at least 90% amino acid identity to a second amino acid sequence, the second amino acid sequence as shown in SEQ ID NO:3 or SEQ ID NO:4.

The subject invention further provides a method of preventing infection of mosquitoes by *Plasmodium* sp., the method comprising exposing the *Plasmodium* sp. to an amount of a compound effective to interfere with function of *Plasmodium* sp. *chitinase*, thereby preventing infection of the mosquitoes by the *Plasmodium* sp.

Further provided is a method of preventing transmission of malaria by a mosquito feeding on a subject that may harbor *Plasmodium* sp. organisms. The method comprises administering to the subject an amount of a composition of the *Plasmodium* sp. *chitinase* effective to induce production of an antibody specific for *Plasmodium* sp. *chitinase* in the subject, wherein the antibody inhibits *Plasmodium* sp. *chitinase* and is transferred to a mosquito feeding on the subject thereby preventing infection of the mosquito by *Plasmodium* sp. organisms that may be harbored in the subject.

Alternatively, the method of preventing transmission of malaria by a mosquito feeding on a subject that may harbor *Plasmodium* sp. organisms can comprise administering to the subject an amount of a compound effective to interfere with function of *Plasmodium* sp. *chitinase* in the subject, wherein the compound is transferred to a mosquito feeding on the subject thereby preventing infection of the mosquito by *Plasmodium* sp. organisms that may be harbored in the subject.

Also provided is a method of preventing transmission of malaria by a mosquito that ingests *Plasmodium* sp. organisms. The method comprises introducing into the mosquito an amount of a compound effective to interfere with function of *Plasmodium* sp. *chitinase* thereby preventing infection of the mosquito by ingested *Plasmodium* sp. organisms.

BRIEF DESCRIPTION OF THE DRAWINGS

These and other features and advantages of this invention will be evident from the following detailed description of preferred embodiments when read in conjunction with the accompanying drawings in which:

FIG. 1a: quaternary ammonium anion exchange HPLC of crude ookinete extracts. The gradient from 20 to 500 mM NaCl was developed over 30 min. *Chitinase*-containing fractions (*) eluted at 150–250 mM NaCl. FIG. 1b: hydrophobic interaction HPLC. *Chitinase*-containing fractions from 1a were injected into a phenyl-TSK hydrophobic interaction column. *Chitinase*-containing fractions eluted 18 min after the ammonium sulfate concentration reached 0 M. FIG. 1c: because of a high base line, the *chitinase*-containing fractions from 1b were re-injected onto the same hydrophobic interaction column (HIC). FIG. 1d: *chitinase*-containing fractions from 1c were injected into a C18 reverse-phase HPLC column. FIG. 1e: SDS-polyacrylamide gel electrophoresis and Coomassie Blue staining of fractions from 1d. Solid lines in the panels indicate absorbance; lines with ♦ indicate *chitinase* activity.;

FIG. 3 shows the complete amino acid sequence of the *P. gallinaceum chitinase* gene, PgCHT1. Dashed box indicates putative signal sequence. N-terminal 1 and N-terminal 2 indicate the amino termini determined by direct Edman degradation sequencing of the purified 60-kDa doublet (FIG. 1e, fractions 62–64). GT29, GT33, and GT84 indicate the Edman degradation-determined amino acid sequences of tryptic peptides derived from the 60-kDa doublet. Barbells indicate the synthetic peptides used for making antisera (see Materials and Methods). Short arrows indicate sites of proteolysis by Endo Lys-C. The consensus catalytic active site and substrate-binding site are labeled and shaded. * indicates the termination codon;

FIG. 4a: aliquots of fractions 65 and 66 from FIG. 1e were subjected to 4–20% SDS-PAGE and transferred to nitrocellulose. The same blot was sequentially reacted with the carboxyl terminus antiserum (C-term) (right panel), stripped, and then reacted with the active site (AS) antiserum (left panel). FIGS. 4b and 4c show Western immunoblot and determination of enzymatic activity, performed in a time course experiment. At 1.5 h after exflagellation and fertilization, the parasites are in the zygote stage. At 10 h, the intermediate form in which ookinetes are exiting the residual body, the retort stage, are present. Fully mature ookinetes are not seen until about 15 h after zygote formation. FIG. 4b is a Western immunoblot of parasite proteins at various time points after zygote formation, using antisera directed against synthetic peptides derived from the catalytic active site and the carboxyl-terminal domain. Parasite proteins were extracted with a mixture of protease inhibitors (see Materials and Methods). An equal number of parasite equivalents were loaded into each lane or assayed for *chitinase* activity. Single arrowheads indicate proteins associated with peak 1 of *chitinase* activity; double arrowheads indicate proteins associated with peak 2 of *chitinase* activity. The thin arrow indicates the precursor of the protein doublet of 68-kDa indicated by the upper single arrowhead, as demonstrated by a Western immunoblot using antisera directed against the pro-enzyme domain. Protein bands that do not increase in intensity during the course of ookinete development, and thus presumably are not *chitinases*, are not indicated with arrowheads. FIG. 4c shows *chitinase* activity, as detected with 4-MU GlcNAc$_3$, as a function of time after zygote formation;

FIG. 5a shows that quaternary ammonium anion exchange HPLC of ookinete extracts using a shallower gradient than that used in FIG. 1a was able to separate peaks of *chitinase* activity. Proteins from each peak of *chitinase* activity were subjected to SDS-PAGE with a 4–20% polyacrylamide gel under both non-reducing and reducing conditions and immunoblotted (5b–5e). FIGS. 5b and 5d show non-reduced and reduced, respectively, probed with active site antiserum; FIGS. 5c and 5e show non-reduced and reduced, respectively, probed with carboxyl-terminal antiserum;

FIG. 7a: the NT1 form of PgCHT1 (amino acids (aa) Tyr$^{65}$ to Gln$^{587}$) was amplified from a synthetic PgCHT1 gene constructed in *E. coli* preferred codons with NcoI and XhoI restriction sites included in the 5' and 3' ends of the PCR primers, respectively. The NcoI and XhoI restriction enzyme-digested PCR product was cloned into the NcoI and XhoI restriction sites of the bacterial expression vector, pET32b. This vector expresses proteins fused to a 105-amino acid thioredoxin (trx) leader sequence and to hexahistidine tags (His$_6$) at both the amino and carboxyl termini. An enterokinase cleavage site allows for removal of the amino-terminal fusion protein, leaving the correct NT1 amino terminus of rPgCHT1-NT1. Endo Lys-C was experimentally determined (see FIGS. 6a–6d and text) to cleave rPgCHT1-NT1 as shown schematically. The PgCHT1-NT1 construct used for enzymological analysis corresponds to one of the forms of the PgCHT1 gene product secreted by ookinetes, as determined by direct amino-terminal sequencing of the purified 60-kDa *chitinase* (FIG. 1e and FIG. 3). FIG. 7b: rPgCHT1-NT1 degrades polymeric chitin in a glycol chitin activity gel. Equal amounts of rPgCHT1-NT1 (prepared and treated as described under Materials and Methods) were electrophoresed in a native, non-denaturing 8% polyacrylamide gel into which 0.02% glycol chitin had been incorporated. After the gel was run and was incubated in 0.1 M sodium phosphate, pH 6.8, the gel was counterstained with Calcofluor White and visualized by transillumination with UV light. FIG. 7c: rPgCHT1-NT1cleaves 4-MU GlcNAc$_3$ and is enhanced by Endo Lys-C but not enterokinase proteolytic treatment. *Chitinase* activity is represented as fold change of relative fluorescence units;

FIG. 9a: TLC analysis of end products produced by *P. gallinaceum* ookinete crude extracts on 4-MU GlcNAc$_{1-4}$ substrates. FIG. 9b: quantitation of fluorescence produced by *P. gallinaceum* ookinete crude extracts on 4-MU GlcNAc$_{1-4}$ substrates. FIG. 9c: TLC analysis of end products produced by Endo Lys-C-treated rPgCHT1 on 4-MU GlcNAc$_{1-4}$ substrates. FIG. 9d: quantitation of fluorescence produced by Endo Lys-C-treated rPgCHT1 on 4MU GlcNAc$_{1-4}$ substrates. Substrate lengths are indicated on top; reaction products are indicated at right. S, at left of panels 9a and 9c indicates unreacted substrates as standards. Free 4-MU fluorescences 12 times that of 4-MU derivatives of GlcNAc oligomers; thus, the weaker fluorescent bands corresponding to the mono-, di- and tetra-MU cannot be compared stoichiometrically to the free 4-MU;

FIG. 11 illustrates a comparison of amino acid sequences of PfCHT1 and PgCHT1. The predicted signal peptides are underlined. Putative proenzyme, catalytic, and chitin-binding domains are indicated; substrate-binding and catalytic active sites are overlined. NT1 and NT2 delineate the two secreted forms of PgCHT1;

FIGS. 12a–12c illustrate restriction mapping, chromosomal localization, and transcriptional activity of the PfCHT1 gene. FIG. 12a is a Southern blot of *P. falciparum* strain 3D7. Restriction enzymes used to digest the DNA are shown across the top; molecular sizes are indicated in bp at left. FIG. 12b shows chromosomal localization of PfCHT1 by PCR on pulse-field gel-electrophoresis-separated *P. falciparum* chromosomal DNA. Gene-specific primers demonstrate that PfCHT1 is located on chromosome 12. Std, 500-bp DNA ladder, shown at left. Chromosome numbers are at the top. Dd2, genomic DNA template from *P. falciparum* strain Dd2 used as a positive control. FIG. 12c shows reverse transcription-PCR (RT-PCR) analysis to determine the presence of PfCHT1 message in total RNA extracted from *P. falciparum*-infected A. freeborni midguts. The same preparation of RNA was used for RT-PCR of both PfCHT1 and Pfs28. RT-PCR of Pfs28 mRNA, which encodes an *P. falciparum* zygote/ookinete surface protein, was included as a positive control. The 100-bp ladder is indicated; +RT and RT, with and without reverse transcriptase;

In FIG. 13a, a lysate of induced bacteria cell mass was clarified, run over a nickel-Sepharose column, and eluted with a step gradient of imidazole in 1 M NaCl/20 mM Tris, pH 8.0. Fractions were assayed for *chitinase* activity by microfluorimetry with 4MU-GlcNAc$_3$. In FIG. 13b, samples-were analyzed by SDS/PAGE; the gel was stained with Coomassie blue. In FIG. 13c, treatment of pooled fractions 21 and 22 with enterokinase (EK) after dialysis of the protein against 20 mM Tris, pH 7.5/50 mM NaCl/2 mM CaCl$_2$ is shown;

FIGS. 14a–14c show analysis of the action of rPfCHT1 on native chitin oligosaccharide substrates and 4MU derivatives of chitin oligosaccharides. FIG. 14a shows TLC analysis of end products produced by rPfCHT1 on native GlcNAc$_{1-6}$. FIG. 14b shows TLC analysis of end products produced by rPfCHT1 on 4MU-GlcNAc$_{1-4}$. Oligosaccharide substrate lengths are indicated at the top, and reaction products are shown at right. The origins at which the reaction mixtures were spotted are as indicated. Free 4MU fluoresces 12 times more than 4MU derivatives of GlcNAc oligomers; thus, the weaker fluorescent bands corresponding to the mono-, di-, and tetra-MU cannot be compared stoichiometrically to the free 4MU. The origins at which the reaction mixtures were spotted are indicated. S, 4-MU GlcNAc$_{1-4}$ standards. FIG. 14c shows microfluorimetry analysis of initial rates of fluorescence produced by rPfCHT1 on 4MU substrates, as a measure of relative initial reaction rates of *chitinase* activity;

FIG. 15a shows the relative rates of rPfCHT1 activity at different pH levels. Shaded bar indicates that at pH 4.5, initial enzyme activity is linear for 10 min at 37° C., but then slows and is irreversibly gone at 20 min. rPfCHT1 has no *chitinase* activity at pH 3.5 or 4.0. Data are displayed as the mean of three separate experiments; errors are 5–7%. FIG. 15b shows relative rates of allosamidin inhibition of rPfCHT1 activity at pH 5.0 (■) and pH 6.0 and 7.0 (♦). 4MU-GlcNAc$_3$ was used as substrate for both sets of experiments.

DETAILED DESCRIPTION OF THE INVENTION

Figure 1A:
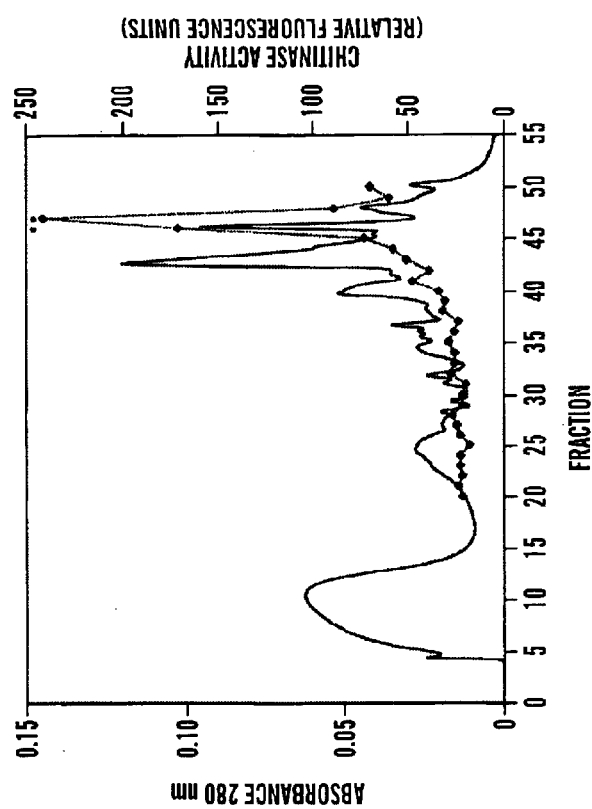
FIGS. 1a–1e illustrate the purification of the *P. gallinaceum chitinase*.
Figure 1B:
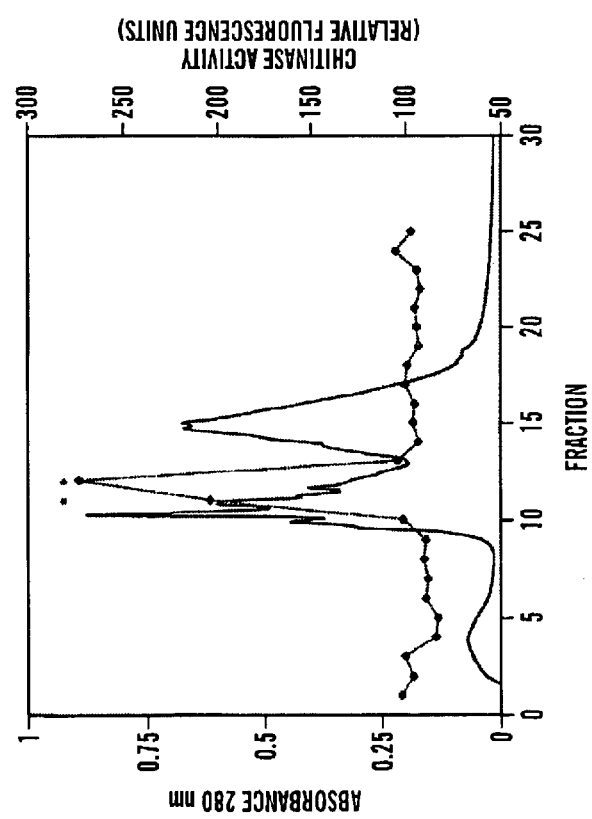
Figure 1C:
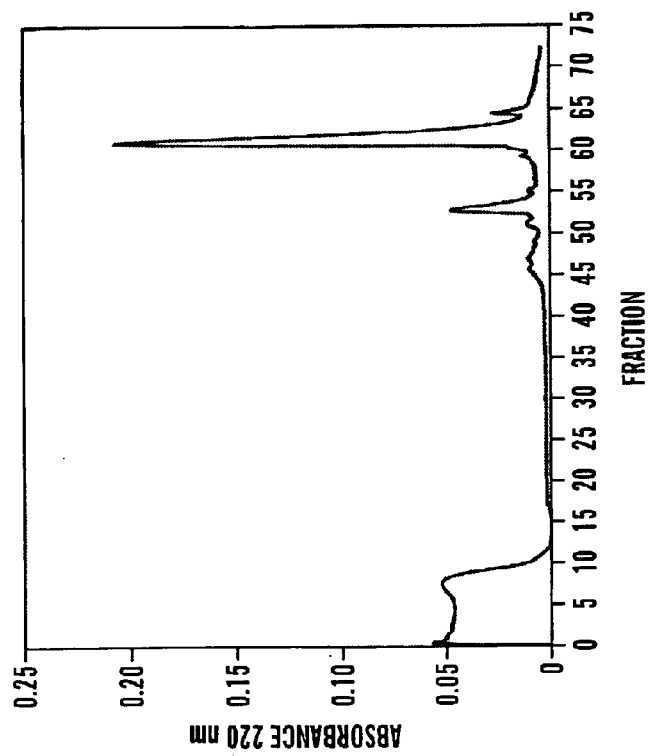
Figure 1D:
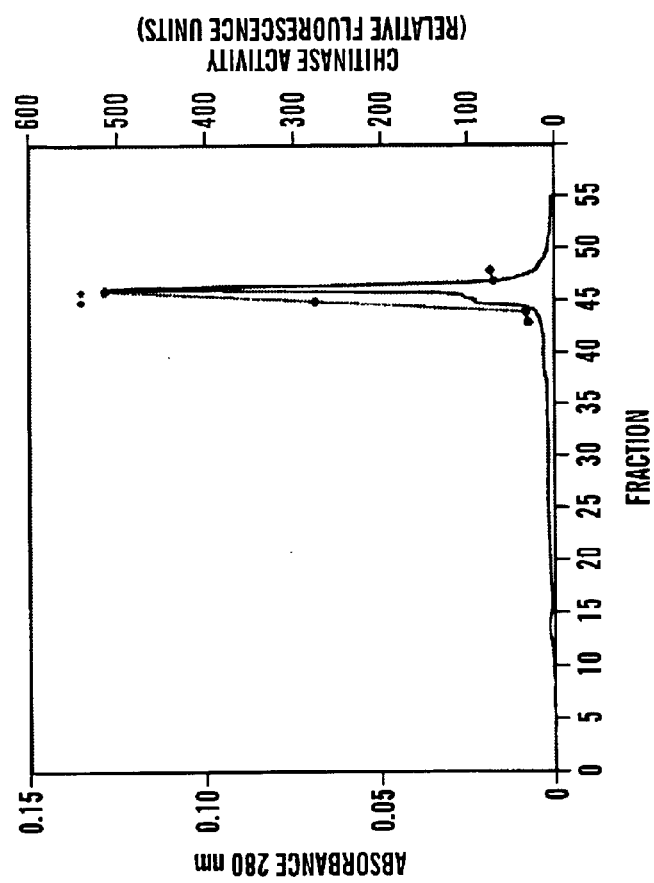

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic nucleic acid.

By a nucleic acid sequence "homologous to" or "complementary to", it is meant a nucleic acid that selectively hybridizes, duplexes or binds to DNA sequences encoding the protein or portions thereof when the DNA sequences encoding the protein are present in a genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein or peptide. The nucleic acid molecule includes both the full length nucleic acid sequences as well as non-full length sequences derived from the full length protein. It being further understood that the sequence includes the degenerate codons of the native sequence or sequences which may be introduced to provide codon preference in a specific host cell.

The term "located upstream" as used herein refers to linkage of a promoter upstream from a nucleic acid (DNA) sequence such that the promoter mediates transcription of the nucleic acid (DNA) sequence.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during, mitosis as an autonomous structure, or the plasmid is incorporated within the host's genome.

The phrase "heterologous protein" or "recombinantly produced heterologous protein" refers to a peptide or protein of interest produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques. As used herein, a "substantially purified" or "isolated" protein (or peptide) can be synthetically or chemically produced, or recombinantly produced. A "substantially purified" or "isolated" protein or peptide as used herein is not intended to include a protein or peptide separated from an organism.

"Biological sample" or "sample" as used herein refers to any sample obtained from a living organism or from an organism that has died. Examples of biological samples include body fluids and tissue specimens.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. High stringency may be attained, for example, by overnight hybridization at about 68° C. in a 6×SSC solution, washing at room temperature with 6×SSC solution, followed by washing at about 68° C. in a 6×SSC solution then in a 0.6×SSX solution.

Hybridization with moderate stringency may be attained, for example, by: 1) filter pre-hybridizing and hybridizing with a solution of 3× sodium chloride, sodium citrate (SSC), 50% formamide, 0.1M Tris buffer at pH 7.5, 5× Denhardt's solution; 2) pre-hybridization at 37° C. for 4 hours; 3) hybridization at 37° C. with amount of labeled probe equal to 3,000,000 cpm total for 16 hours; 4) wash in 2×SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al. 1989.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the peptide/protein to which the relevant sequence listing relates.

The DNA molecules of the subject invention also include DNA molecules coding for protein analogs, fragments or derivatives of the protein which differ from naturally-occurring forms (the naturally-occurring protein) in terms of the identity or location of one or more amino acid residues (deletion analogs containing less than all of the residues specified for the protein, substitution analogs wherein one or more residues specified are replaced by other residues, and addition analogs wherein one or more amino acid residues are added to a terminal or medial portion of the protein) and which share the function of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

As used herein, a "peptide" refers to an amino acid sequence of three to one hundred amino acids, and therefore an isolated peptide that comprises an amino acid sequence is not intended to cover amino acid sequences of greater than 100 amino acids. Preferably, the peptides that can be identified and used in accordance with the subject invention (whether they be mimotope or anti-mimotope peptides) are less than 50 amino acids in length, and more preferably the peptides are five to 20 amino acids in length or 20–40 amino acids in length.

The peptides can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptides depends, in part, on the desired characteristics of the peptide. For example, the incorporation of one or more (D)-amino acids can confer increased stability on the peptide and can allow a peptide to remain active in the body for an extended period of time. The incorporation of one or more (D)-amino acids can also increase or decrease the pharmacological activity of the peptide.

The peptides may also be cyclized, since cyclization may provide the peptides with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC, 46:257 (1981) and Raucher et al., Tetrahedron. Lett., 21:14061 (1980). An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual peptide based on the modifications to the backbone or side chain functionalities. For example, these types of alterations to the amino acid substituents and peptides can enhance the peptide's stability to enzymatic breakdown and increase biological activity. Modifications to the peptide backbone similarly can add stability and enhance activity.

One skilled in the art, using the above sequences or formulae, can easily synthesize the peptides. Standard procedures for preparing synthetic peptides are well known in the art. The novel peptides can be synthesized using: the solid phase peptide synthesis (SPPS) method of Merrifield (J. Am. Chem. Soc., 85:2149 (1964)) or modifications of SPPS; or, the peptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985).

With these definitions in mind, the subject invention provides an isolated nucleic acid molecule encoding a *Plasmodium* sp. *chitinase*. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the channel.

An example of such a Plasmodium sp. chitinase is the Plasmodium falciparum chitinase encoded by the nucleotide sequence as shown in SEQ ID NO:1 (this is the open reading frame). The amino acid sequence encoded by this nucleotide sequence is shown in SEQ ID NO:3. Another example of such a Plasmodium sp. chitinase is the Plasmodium gallinaceum chitinase encoded by the nucleotide sequence as shown in SEQ ID NO:2 (this is the open reading frame). The amino acid sequence encoded by this nucleotide sequence is shown in SEQ ID NO:4. The nucleotide sequence of the full gene for the Plasmodium gallinaceum chitinase is shown in SEQ ID NO:5.

The invention also provides an oligonucleotide that is complementary to at least a portion of the mRNA encoding the Plasmodium sp. chitinase. Oligonucleotides can be RNA or single-stranded DNA, and can be complementary to the entire mRNA molecule encoding the protein (i.e. of the same nucleotide length as the entire molecule). It may be desirable, however, to work with a shorter molecule. In this instance, the oligonucleotide can be complementary to a portion of the entire mRNA molecule encoding the protein. These shorter oligonucleotides are capable of hybridizing to the mRNA encoding the entire molecule, and preferably consist of about twenty to about one hundred nucleotides. These oligonucleotides can be used to reduce levels of Plasmodium sp. chitinase, by introducing into cells an RNA or single-stranded DNA molecule that is complementary to at least a portion of the mRNA of the protein (i.e. by introducing the oligonucleotide). The oligonucleotide can base-pair with the mRNA of the protein, preventing translation of the mRNA into protein. Thus, an oligonucleotide can prevent translation of mRNA encoding the protein into a functional protein. It may be desirable to place the oligonucleotide downstream and under the control of a particular promoter, so that the oligonucleotide will prevent translation of mRNA encoding the protein only in cells in which the particular promoter functions.

More particularly, an oligonucleotide complementary to at least a portion of mRNA encoding a Plasmodium sp. chitinase can be used to decrease expression of a functional channel. A cell with a first level of expression of a functional Plasmodium sp. chitinase is selected, and then the oligonucleotide is introduced into the cell. The oligonucleotide blocks expression of functional Plasmodium sp. chitinase, resulting in a second level of expression of a functional Plasmodium sp. chitinase in the cell. The second level is less than the initial first level.

Oligonucleotides can be introduced into cells by any suitable means. In one embodiment, the oligonucleotide RNA molecule is injected directly into the cellular cytoplasm, where the RNA interferes with translation. A vector may also be used for introduction of the oligonucleotide into a cell. Such vectors include various plasmid and viral vectors. For a general discussion of oligonucleotides such as antisense molecules and their use, see Han et al. 1991 and Rossi 1995.

The nucleic acid molecules of the subject invention can be expressed in suitable host cells using conventional techniques. Any suitable host and/or vector system can be used to express the Plasmodium sp. chitinase.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the Plasmodium sp. chitinase can be injected into the nucleus of a host cell or transformed into the host cell using a suitable vector, or mRNA encoding the Plasmodium sp. chitinase can be injected directly into the host cell, in order to obtain expression of Plasmodium sp. chitinase in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. One such virus widely used for protein production is an insect virus, baculovirus. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the Plasmodium sp. chitinase has been introduced can be used to produce the Plasmodium sp. chitinase.

Having identified the nucleic acid molecules encoding *Plasmodium* sp. *chitinases* and methods for expressing the *Plasmodium* sp. *chitinases* encoded thereby, the invention further provides methods of screening a substance (for example, a compound or inhibitor) for the ability of the substance to modify *Plasmodium* sp. *chitinase* function. In one embodiment, the method comprises introducing a nucleic acid molecule encoding the *Plasmodium* sp. *chitinase* into a host cell, and expressing the *Plasmodium* sp. *chitinase* encoded by the molecule in the host cell. The cell is then exposed to a substance and evaluated to determine if the substance modifies the function of the *Plasmodium* sp. *chitinase*. In another embodiment, an isolated *Plasmodium* sp. *chitinase* (see below) is exposed to the substance for evaluation of whether the substance modifies the function of the *Plasmodium* sp. *chitinase*. From these evaluations, substances effective in altering the function of the *Plasmodium* sp. *chitinase* can be found. Such agents may be agonists or antagonists, with antagonists being preferred herein.

The evaluation of a cell to determine if the substance modifies the function of the *Plasmodium* sp. *chitinase* can be by any means known in the art. The evaluation can comprise the direct monitoring of expression of *Plasmodium* sp. *chitinase* in the host cell, or the evaluation can be indirect.

The nucleic acid molecules of the subject invention can be used either as probes or for the design of primers to obtain DNA encoding other *Plasmodium* sp. *chitinases* by either cloning and colony/plaque hybridization or amplification using the polymerase chain reaction (PCR).

Specific probes derived from SEQ ID NO:1 or SEQ ID NO:2 can be employed to identify colonies or plaques containing cloned DNA encoding a member of the *Plasmodium* sp. *chitinase* family using known methods (see Sambrook et al. 1989). One skilled in the art will recognize that by employing such probes under high stringency conditions (for example, hybridization at 42° C. with 5×SSPC and 50% formamide, washing at 50–65° C. with 0.5×SSPC), sequences having regions which are greater than 90% homologous or identical to the probe can be obtained. Sequences with lower percent homology or identity to the probe, which also encode *Plasmodium* sp. *chitinases*, can be obtained by lowering the stringency of hybridization and washing (e.g., by reducing the hybridization and wash temperatures or reducing the amount of formamide employed).

More particularly, in one embodiment, the method comprises selection of a DNA molecule encoding a *Plasmodium* sp. *chitinase*, or a fragment thereof, the DNA molecule having a nucleotide sequence as shown in SEQ ID NO:1 or SEQ ID NO:2, and designing an oligonucleotide probe for *Plasmodium* sp. *chitinase* based on the nucleotide sequence of the selected DNA molecule. A genomic or cDNA library of an organism is then probed with the oligonucleotide probe, and clones are obtained from the library that are recognized by the oligonucleotide probe so as to obtain DNA encoding another *Plasmodium* sp. *chitinase*.

Specific primers derived from SEQ ID NO:1 or SEQ ID NO:2 can be used in PCR to amplify a DNA sequence encoding a member of the *Plasmodium* sp. *chitinase* family using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% homologous or identical to the primers will be amplified.

More particularly, in a further embodiment the method comprises selection of a DNA molecule encoding *Plasmodium* sp. *chitinase*, or a fragment thereof, the DNA molecule having a nucleotide sequence as shown in SEQ ID NO:1 or SEQ ID NO:2, designing degenerate oligonucleotide primers based on the nucleotide sequence of the selected DNA molecule, and employing such primers in the polymerase chain reaction using as a template a DNA sample to be screened for the presence of *Plasmodium* sp. *chitinase*-encoding sequences. The resulting PCR products can be isolated and sequenced to identify DNA fragments that encode polypeptide sequences corresponding to the targeted region of *Plasmodium* sp. *chitinase*.

Various modifications of the nucleic acid and amino acid sequences disclosed herein are covered by the subject invention. These varied sequences still encode a functional *Plasmodium* sp. *chitinase*. The invention thus further provides an isolated nucleic acid molecule encoding a *Plasmodium* sp. *chitinase*, the nucleic acid molecule encoding a first amino acid sequence having at least 90% amino acid identity to a second amino acid sequence, the second amino acid sequence as shown in SEQ ID NO:3 or SEQ ID NO:4. In further embodiments, the first amino acid sequence has at least 95%, 96%, 97%, 98%, or 99% amino acid identity to SEQ ID NO:3 or SEQ ID NO.:4.

The invention further provides an isolated DNA oligomer capable of hybridizing to the nucleic acid molecule encoding *Plasmodium* sp. *chitinase* according to the subject invention. Such oligomers can be used as probes in a method of detecting the presence of *Plasmodium* sp. *chitinase* in a sample. More particularly, a sample can be contacted with the DNA oligomer and the DNA oligomer will hybridize to any *Plasmodium* sp. *chitinase* present in the sample, forming a complex therewith. The complex can then be detected, thereby detecting presence of *Plasmodium* sp. *chitinase* in the sample.

The complex can be detected using methods known in the art. Preferably, the DNA oligomer is labeled with a detectable marker so that detection of the marker after the DNA oligomer hybridizes to any *Plasmodium* sp. *chitinase* in the sample (wherein non-hybridized DNA oligomer has been washed away) is detection of the complex. Detection of the complex indicates the presence of *Plasmodium* sp. *chitinase* in the sample. As will be readily apparent to those skilled in the art, such a method could also be used quantitatively to assess the amount of *Plasmodium* sp. *chitinase* in a sample.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

The invention further provides an isolated *Plasmodium* sp. *chitinase*. The protein is preferably encoded by a nucleotide sequence as shown in SEQ ID NO:1 or SEQ ID NO:2 (*Plasmodium falciparum* and *Plasmodium gallinaceum*, respectively). The protein preferably has an amino acid sequence as shown in SEQ ID NO:3 or SEQ ID NO:4 (*Plasmodium falciparum* and *Plasmodium gallinaceum*, respectively). Further provided is an isolated *Plasmodium* sp. *chitinase* encoded by a first amino acid sequence having at least 90% amino acid identity to a second amino acid sequence, the second amino acid sequence as shown in SEQ ID NO:3 or SEQ ID NO;4. In further embodiments, the first amino acid sequence has at least 95%, 96%, 97%, 98%, or 99% amino acid identity to SEQ ID NO:3 or SEQ ID NO:4.

It should be readily apparent to those skilled in the art that the met residue that is present at the amino terminal of the amino acid sequence of the *Plasmodium* sp. *chitinase* (i.e., SEQ ID NO:3 and SEQ ID NO:4) and the ATG that is present at the 5' end of the nucleotide sequence (i.e., SEQ ID NO:1 and SEQ ID NO:2), are often added in order to express the *chitinase* in a bacterial host cell. The non-met version of the *chitinase* is thus specifically intended to be covered by reference to SEQ ID NO:1, SEQ ID NO:2, SEQ ID NO:3, or SEQ ID NO:4.

It should also be readily apparent to those skilled in the art that the signal peptide is cleaved after secretion. Both the precursoe form of the *chitinase* which includes the signal peptide and the form minus the signal peptide are specifically intended to be covered by reference to SEQ ID NO:1, SEQ ID NO:2, SEQ ID NO:3, or SEQ ID NO:4.

The invention further provides an antibody or fragment thereof specific for the *Plasmodium* sp. *chitinase* of the subject invention. Antibodies of the subject invention include polyclonal antibodies and monoclonal antibodies capable of binding to the *Plasmodium* sp. *chitinase*, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the F(ab')$_2$, and the Fc fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic *Plasmodium* sp. *chitinase* (or an antigenic fragment thereof). Methods for immunization are well known in the art. Such methods include subcutaneous or intraperitoneal injection of the protein. One skilled in the art will recognize that the amount of the protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

In accordance with the above discussion, the subject invention further provides a method of producing an antibody specific for a *Plasmodium* sp. *chitinase* in a host. The method comprises selecting the isolated *Plasmodium* sp. *chitinase* or an antigenic portion thereof and introducing the selected *Plasmodium* sp. *chitinase* or antigenic portion thereof into a host to induce production of an antibody specific for *Plasmodium* sp. *chitinase* in the host.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express *Plasmodium* sp. *chitinase*, to identify samples containing *Plasmodium* sp. *chitinase*, or to detect the presence of *Plasmodium* sp. *chitinase* in a sample. More particularly, the antibodies or fragments thereof can thus be used to detect the presence of *Plasmodium* sp. *chitinase* in a sample, by contacting the sample with the antibody or fragment thereof. The antibody or fragment thereof binds to any *Plasmodium* sp. *chitinase* present in the sample, forming a complex therewith. The complex can then be detected, thereby detecting the presence of *Plasmodium* sp. *chitinase* in the sample. As will be readily apparent to those skilled in the art, such a method could also be used quantitatively to assess the amount of *Plasmodium* sp. *chitinase* in a sample. As should also be readily apparent, such an antibody may also be used to decrease levels of functional *Plasmodium* sp. *chitinase*, by blocking the protein. Such antibodies could therefore be used in the methods of the subject invention to prevent infection of mosquitoes by *Plasmodium* sp. by interfereing with function of *Plasmodium* sp. *chitinase*.

Further provided is a composition comprising the *Plasmodium* sp. *chitinase* or an antigenic portion thereof and a compatible carrier. Such compositions have numerous uses, including the use as a vaccine. More specifically, the subject invention further provides a method of preventing transmission of malaria by a mosquito feeding on a subject that may harbor *Plasmodium* sp. organisms. The method comprises administering to the subject an amount of a composition of the *Plasmodium* sp. *chitinase* effective to induce production of an antibody specific for *Plasmodium* sp. *chitinase* in the subject, wherein the antibody inhibits *Plasmodium* sp. *chitinase* and is transferred to a mosquito feeding on the subject thereby preventing infection of the mosquito by *Plasmodium* sp. organisms that may be harbored in the subject.

In the methods of the invention, tissues or cells are contacted with or exposed to the composition of the subject invention or a compound. In the context of this invention, to "contact" tissues or cells with or to "expose" tissues or cells to a composition or compound means to add the composition or compound, usually in a liquid carrier, to a cell suspension or tissue sample, either in vitro or ex vivo, or to administer the composition or compound to cells or tissues within a subject (including the malarial parasites and mosquitoes, and human subjects, for example).

In one embodiment, the invention provides a method of preventing infection of mosquitoes by *Plasmodium* sp., the method comprising exposing the *Plasmodium* sp. to an amount of a compound effective to interfere with function of *Plasmodium* sp. *chitinase*. It should be readily apparent that one might expose the *Plasmodium* sp. to the compound directly or indirectly (for example, expose the parasite directly, or expose the parasite via the mosquito vector or via the human host).

For example, one embodiment of the subject invention provides a method of preventing transmission of malaria by a mosquito feeding on a subject that may harbor *Plasmodium* sp. organisms which comprises administering to the subject an amount of a compound effective to interfere with function of *Plasmodium* sp. *chitinase* in the subject, wherein the compound is transferred to a mosquito feeding on the subject thereby preventing infection of the mosquito by *Plasmodium* sp. organisms that may be harbored in the subject. A further embodiment of the subject invention provides a method of preventing transmission of malaria by a mosquito that ingests *Plasmodium* sp. organisms. The method comprises introducing into the mosquito an amount of a compound effective to interfere with function of *Plasmodium* sp. *chitinase* thereby preventing infection of the mosquito by ingested *Plasmodium* sp. organisms.

Interfering with (decreasing or preventing) function of *Plasmodium* sp. *chitinase* refers to modifying expression of the protein and/or modifying activity of the protein such as by inhibiting the function of the protein.

Function of *Plasmodium* sp. *chitinase* can be interfered with by various methods, at the gene and protein levels. In one embodiment, the function is interfered with by reducing *Plasmodium* sp. *chitinase* gene expression of the *chitinase* protein in the parasite. This can be accomplished by exposing the parasites to a compound which reduces *Plasmodium* sp. *chitinase* gene expression. The compound could be, for example, an antisense oligonucleotide targeted to the *Plasmodium* sp. *chitinase*.

Other methods for interfering with *Plasmodium* sp. *chitinase* gene expression could also involve site-directed mutagenesis of the *chitinase* gene to prevent expression of the *chitinase*, or various gene therapy techniques.

Interference with function of the *Plasmodium* sp. *chitinase* can also be accomplished by exposing the *Plasmodium* sp. to a compound which inhibits function of the *Plasmodium* sp. *chitinase*. Inhibitors could readily be identified by screening methods (including the methods described above).

Using these screening methods, several inhibitors have been identified. These inhibitors include: barbituric acids, 1,3,5-triazinane-2-thiones, N-substituted-phenylcarbamates, and allosamizolines.

As used herein, "barbituric acids" are meant to include derivatives and congeners of barbituric acid, particularly derivatives and congeners of barbituric acid that is substituted in the 5-position with an alkyl group, preferably with an alkyl group which is itself substituted with a aryl group or a heterocyclic group. Derivatives and congeners of barbituric acid that is substituted in the 5-position with an alkyl group are meant to include compounds having the formula ("Formula 1"):

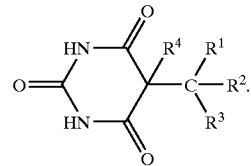

$R^1$, $R^2$, $R^3$, and $R^4$ can be independently selected from the group consisting of a hydrogen atom, a halogen atom, an alkyl group, an aryl group, and a non-aromatic heterocyclic group. For example, $R^4$ can be H, one or two of $R^1$, $R^2$, and $R^3$ can be hydrogen atoms, and the other two or one of $R^1$, $R^2$, and $R^3$ can be selected from the group consisting of an alkyl group, an aryl group, and a non-aromatic heterocyclic group. Alternatively, two or more of $R^1$, $R^2$, and $R^3$, taken together with the carbon to which they are bonded, can form a keto (C=O) group, a cycloalkyl group, an aryl group, or a non-aromatic heterocyclic group. For example, $R^1$ can be hydrogen, and $R^2$ and $R^3$, taken together with the carbon to which they are bonded, can form a cycloalkyl group, an aryl group, or a non-aromatic heterocyclic group, such as a cyclohex-1-yl group, a cyclohex-2-en-1-yl group, or a cyclohex-3-en-1-yl group; or $R^1$, $R^2$, and $R^3$, taken together with the carbon to which they are bonded, can form a cycloalkyl group, an aryl group, or a non-aromatic heterocyclic group, such as a phenyl group, a naphthyl group, or a cyclohex-1-en-1-yl group. Still alternatively, $R^4$ and one or more of $R^1$, R2, and $R^3$, taken together with the carbons to which they are bonded, can form a cycloalkyl group, an aryl group, or a non-aromatic heterocyclic group.

"Alkyl", as used herein, is meant to include linear alkyls (e.g., methyl, ethyl, n-propyl, n-pentyl, n-hexyl, n-heptyl, n-octyl, n-nonyl, and the like), branched alkyls (e.g., isobutyl, isopentyl, neopentyl, hex-2-yl, hex-3-yl, hept-2-yl, hept-3-yl, and the like), and cycloalkyls (e.g., cyclopentyl, cyclohexyl, cycloheptyl, 4-methylcyclohexyl, and the like). These alkyl groups can be substituted or unsubstituted. When substituted, suitable substituents include, for example, aryl groups, oxo (i.e., =O) substituents, thio (i.e., =S) substituents, halogen atoms, aldehyde groups, hydroxy groups, alkoxy groups (examples of which include C1–C8 alkoxy groups and-which are meant to include aryloxy groups), thiol, alkylthio or arylthio groups, carboxylic acid groups (which are meant to include carboxylic acid derivatives, such as salts, esters, amides, etc.), amine groups (primary, secondary, or tertiary), nitro groups, sulfonic acid groups, and the like, as well as combinations of these substituents. "Alkyl", as used herein is also meant to include alkyl groups which include one or more sites of unsaturation, such as a but-3-en-1-yl group, a hex-4-en-1-yl group, a hex-4-en-2-yl group, a 5-chlorohex-4-en-2-yl group, a but-3-yn-1-yl group, a cyclohex-3-en-1-yl group, a cyclohex-2-en-1-yl group, a cyclohex-1-en-1-yl group, and the like. "Aryl", as used herein, is meant to include aromatic homocyclic and heterocyclic rings and ring systems, which can optionally be fused and/or contain bridged ring systems and which can optionally be substituted with one or more substituents, for example, selected from alkyl groups, aryl groups, oxo (i.e., =O) substituents, thio (i.e., =S) substituents, halogen atoms, aldehyde groups, hydroxy groups, alkoxy groups (examples of which include C1–C8 alkoxy groups and which are meant to include aryloxy groups), thiol, alkylthio or arylthio groups, carboxylic acid groups (which are meant to include carboxylic acid derivatives, such as salts, esters, amides, etc.), amine groups (primary, secondary, or tertiary), nitro groups, sulfonic acid groups, and the like, as well as combinations of these substituents. "Non-aromatic heterocyclic group", as used herein is meant to include all substituted or unsubstituted cyclic moieties which are neither cycloalkyl groups nor aryl groups. Examples of non-aromatic heterocyclic groups include piperidinyl groups, morpholino groups, hexahydropyrimidinyl groups, 2,4,6-trioxohexahydropyrimidinyl groups (e.g., 2,4,6-trioxohexahydropyrimidin-5-yl groups), and the like. Bridged non-aromatic heterocyclic groups are also meant to be included within "non-aromatic heterocyclic groups".

Illustrative barbituric acids include those having the following formulae:

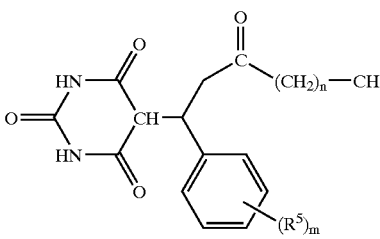

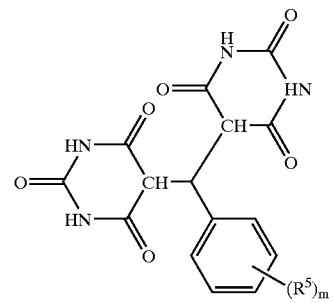

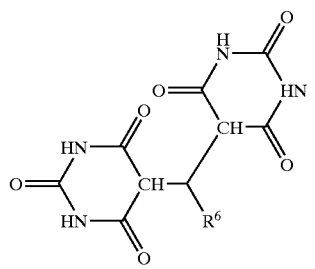

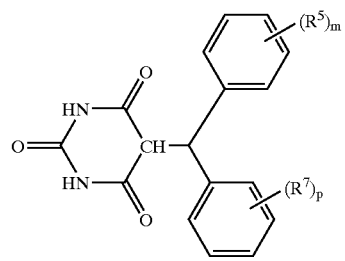

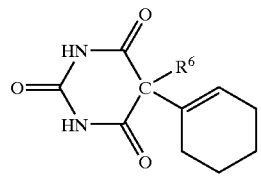

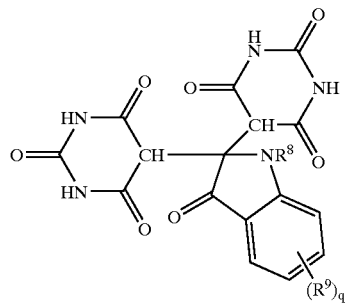

where n is an integer from 0 to 10, such as 0, 1, 2, 3, 4, 5, 6, 7, 9, or 10; each $R^5$, $R^7$, and $R^9$ is independently selected from the group consisting of alkyl groups, aryl groups, halogen atoms, aldehyde groups, hydroxy groups, alkoxy groups (examples of which include C1–C8 alkoxy groups and which are meant to include aryloxy groups), thiol, alkylthio or arylthio groups, carboxylic acid groups (which are meant to include carboxylic acid derivatives, such as salts, esters, amides, etc.), amine groups (primary, secondary, or tertiary), nitro groups, sulfonic acid groups, and the like; $R^6$ is a hydrogen atom, an alkyl group (e.g., a methyl, ethyl, or propyl group); $R^8$ is H, alkyl, or aryl; each of m and p is independently selected from 0, 1, 2, 3, 4, and 5; and q is selected from 0, 1, 2, 3, and 4.

Barbituric acids of the types discussed above can be obtained commercially, for example from Salor, Milwaukee, Wis. or from Maybridge Chemical Company Ltd., Trevillett, Tintagel, Cornwall TL34 OHW United Kingdom. Alternatively they can be readily prepared using conventional methods for synthesizing barbituric acids. Briefly, an appropriately substituted malonic acid dialkyl ester is condensed with urea, preferably in the presence of a strong base, such as sodium ethoxide. For example, barbituric acids having Formula 1, above, can be prepared from malonic acid dialkyl esters having the formula ("Formula 2"):

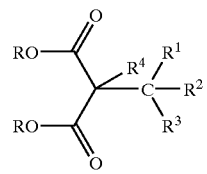

where R is, for example, an alkyl group, such as an ethyl group. As a further example, barbituric acids having the formula:

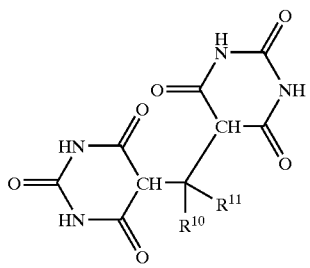

where each of $R^{10}$ and $R^{11}$ is, for example, a hydrogen atom, an aryl group, or an alkyl group (such as where $R^{10}$ is hydrogen and $R^{11}$ is an aryl or alkyl group), can be conveniently prepared in one step by reacting two equivalents of urea with a bis malonic acid dialkyl ester having the formula:

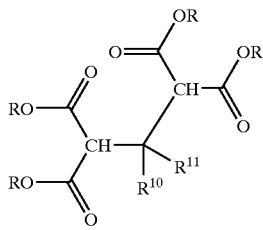

where each R represents, for example, an alkyl (e.g., ethyl) group. Further details relating to this reaction can be found, for example, in Dickey, Gray, Org. Syn., Coll. Vol. II, page 60 (1943), which is hereby incorporated by reference. Appropriately substituted malonic acid dialkyl esters and bis malonic acid dialkyl esters can be prepared by reacting malonic acid dialkyl esters using one or more appropriate electrophiles, such as an alkyl halide or an aryl isocyanate, e.g., having the formula $R^4X$, $XCR^1(R^2)(R^3)$, $R^{10}X$, or $R^{11}X$, where $R^1$, $R^2$, $R^3$, $R^4$, $R^{10}$, and $R^{11}$ represent the substituents on the desired substituted malonic acid dialkyl esters and X represents moiety whose anion, X⁻, is a good leaving group (e.g., Cl⁻) or NCO.

As used herein, "1,3,5-triazinane-2-thiones" are meant to include compounds having the formula:

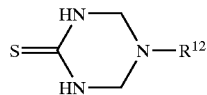

where $R^{12}$ represents an alkyl moiety or a nonaromatic heterocyclic group, as described above. Suitable nonaromatic heterocyclic groups include, for example azepan moieties (which may, optionally be substituted with an oxo (i.e. =O) group), such as 2-oxoazepan-3-yl moieties. Suitable alkyl moieties include unsubstituted branched or unbranched, cyclic or non-cyclic unsubstituted alkyl moieties (e.g., methyl, ethyl, propyl, isopropyl, butyl, isobutyl, t-butyl, 1,1,3,3, tetramethylbut-1-yl, cyclopropyl, cyclopentyl, cyclohexyl, cyclopropylmethyl, cyclopentylmethyl, cyclohexylmethyl, 3-methylcyclohexyl, 3,3-dimethylcyclohexyl, and 3,3,5-trimethylcyclohexyl moieties). Other suitable alkyl moieties include aryl-substituted branched or unbranched, cyclic or non-cyclic alkyl moieties, such as imidazolylalkyl moieties.(e.g., imidazol-1-ylmethyl, imidazol-1-ylethyl, and imidazol-1-ylpropyl moieties); phenylalkyl moieties (e.g., phenylmethyl, phenylethyl, phenylpropyl, and (2,6-dichlorophenyl)methyl moieties); pyridylalkyl moieties (e.g., (2-pyridyl)methyl, (3-pyridyl)methyl, (4-pyridyl)methyl, (2-pyridyl)ethyl, (3-pyridyl)ethyl, (4-pyridyl)ethyl, (2-pyridyl)butyl, (3-pyridyl)butyl, and (4-pyridyl)butyl) moieties; ((alkoxy-substituted)phenyl)methyl moieties (e.g., (4-methoxyphenyl)methyl, (3,4-dimethoxyphenyl)methyl, (4-methoxyphenyl)ethyl, and (3,4-dimethoxyphenyl)ethyl moieties); and thienylalkyl moieties (e.g., thien-2-ylmethyl, thien-2-ylethyl, thien-2-ylpropyl, thien-2-ylbutyl, 2-(thien-2-yl)eth-1-yl, and 2-(thien-2-yl)prop-1-yl moieties). Still other suitable alkyl moieties include hydroxy-substituted and alkoxy-substituted branched or unbranched, cyclic or non-cyclic alkyl moieties, such as methoxymethyl, 4-(propoxy)but-1-yl, 4-(phenoxy)but-2-yl, 1-(hydroxy)but-2-yl, 1-(hydroxy)pent-2-yl, and 1-(hydroxy)hex-2-yl moieties. Still other suitable alkyl moieties include amine-substituted branched or unbranched, cyclic or non-cyclic alkyl moieties, such as (N,N-disubstituted)aminoalkyl moieties (e.g., diethylaminomethyl, dimethylaminomethyl, diethylaminoethyl, dimethylaminomethyl, 4-(N-isopropyl-N-methylamino)but-2-yl, and 2-(N-phenyl-N-methylamino)but-2-yl moieties; and (N-unsubstituted)aminoalkyl moieties (e.g., aminomethyl, aminoethyl, aminopropyl, 2-aminobut-1-yl, and 4-aminocyclohexylethyl moieties). Still other suitable alkyl moieties include branched or unbranched, cyclic or non-cyclic alkyl moieties, which are substituted with nonaromatic heterocyclic groups, such as tetrahydropyrrol-2-ylmethyl, 1-(tetrahydropyrrol-2-yleth-1-yl), 3-(tetrahydropyrrol-2-ylprop-1-yl), (1-ethyltetrahydropyrrol-2-yl)methyl, tetrahydropyrrol-1-ylmethyl, tetrahydropyrrol-1-ylethyl, and 2-(tetrahydropyrrol-1-yl)prop-1-yl moieties.

"1,3,5-triazinane-2-thiones" are also meant to include compounds having the formulae:

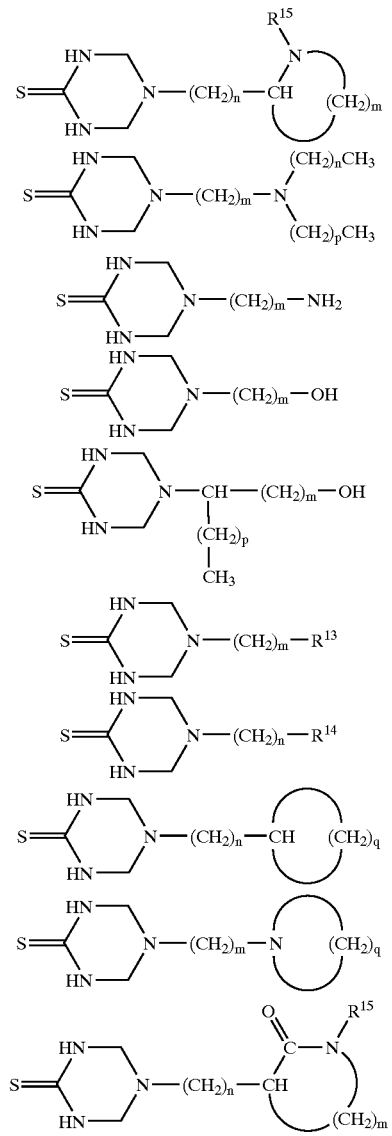

where each of n and p is independently selected from 0, 1, 2, 3, 4, 5, and 6; m is 1, 2, 3, 4, 5, or 6; q is 2, 3, 4, 5, 6, or 7; $R^{13}$ represents a heterocyclic aromatic group; $R^{14}$ represents a homocyclic aromatic group; and $R^{15}$ represents a hydrogen atom or an alkyl or aryl group.

1,3,5-Triazinane-2-thiones of the types discussed above can be obtained commercially, for example from Salor, Milwaukee, Wis. or from Maybridge Chemical Company Ltd., Trevillett, Tintagel, Cornwall TL34 OHW United Kingdom.

As used herein "N-substituted-phenylcarbamates" are meant to include compounds having the formula:

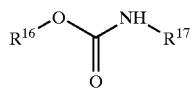

where $R^{16}$ represents an alkyl or aryl group and $R^{17}$ is an aryl group (as described above).

For example, the N-substituted-phenylcarbamates can have the formula:

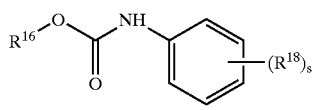

where each $R^{18}$ independently represents alkyl groups, aryl groups, oxo (i.e., =O) substituents, thio (i.e., =S) substituents, halogen atoms, aldehyde groups, hydroxy groups, alkoxy groups (examples of which include C1–C8 alkoxy groups and which are meant to include aryloxy groups), thiol, alkylthio or arylthio groups, carboxylic acid groups (which are meant to include carboxylic acid derivatives, such as salts, esters, amides, etc.), amine groups (primary, secondary, or tertiary), nitro groups, sulfonic acid groups, and the like; and s is 0, 1, 2, 3, 4, or 5. For example, one or more of $R^{18}$ can be a electron-withdrawing group, such as a nitro group, a halogen atom (e.g., fluoro, chloro, bromo, or iodo), a perhaloalkyl group (e.g., trifluoromethyl), or an alkoxy group (e.g., methoxy, ethoxy, etc.).

Illustratively, $R^{17}$ can be a 3-nitrophenyl group, a 3-trifluoromethylphenyl group, a 2,5-dimethoxyphenyl group, a 2-nitro-4-chlorophenyl group, a 2-methoxy-5-nitro group, a 2-fluoro-5-nitro group, a 5-chloro-2,4-dimethoxy group, a 4-nitrophenyl group, a 4-chlorophenyl group, a 3-chlorophenyl group, and a 4-fluoro-3-nitrophenyl group.

As indicated above, $R^{16}$ can be an aryl or alkyl group. Illustrative $R^{16}$ aryl groups include, quinolyl groups (e.g., 5-chloro-8-quinol-1-yl); naphthyl groups (e.g., 5-chloro-8-naphth-1-yl); cyanophenyl groups (e.g., 2-cyanophenyl); halogen substituted phenyl groups (e.g., 2-bromo-4-chlorophenyl, 2-bromo-4-chloro-5-methylphenyl, and 2-chloro-4-fluorophenyl); phenyl groups substituted with carboxylic acid moieties (e.g., 2-carboxyphenyl, 2-carbamoylphenyl, and 2-methoxycarbonylphenyl); phenyl groups bearing unsaturated alkyl substituents (e.g., 4-allyl-2-methoxyphenyl and 4-allylphenyl); and pyridyl groups (e.g., 2-pyridyl and 5-nitro-2-pyridyl). Illustrative $R^{16}$ alkyl groups include, for example, alkyl groups substituted with 2-oxo-1-imidazolidinyloxy moieties (e.g., a 2-(2-oxo-1-imidazolidinyloxy)eth-1-yl group) and alkyl groups substituted with a (N,N-disubstituted)aminoalkyl moiety (e.g., 2-(dimethylamino)eth-1-yl), an N-monosubstituted)aminoalkyl moiety, or an (N-unsubstituted)aminoalkyl moiety. Particular compounds that are illustrative of N-substituted-phenylcarbamates include those having the following formulae:

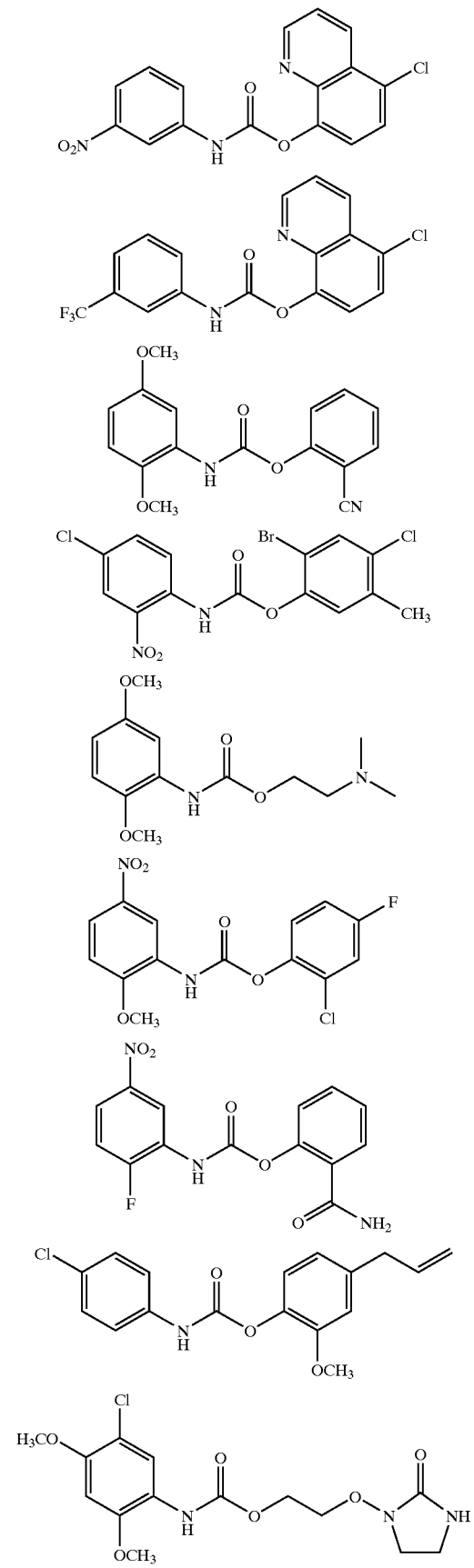

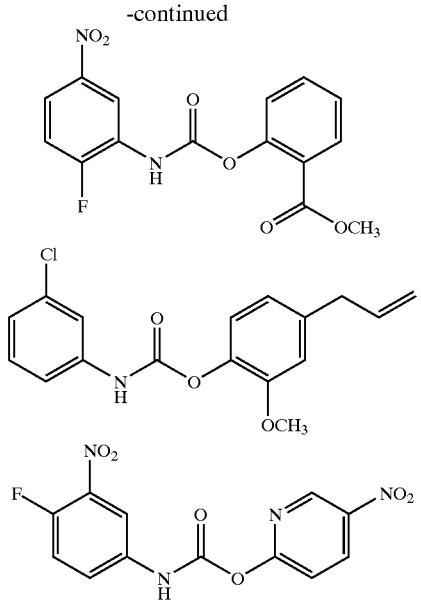

N-substituted-phenylcarbamates of the types discussed above can be obtained commercially, for example from Salor, Milwaukee, Wis.

As used herein, "allosamizolines" are meant to include compounds having the following formula:

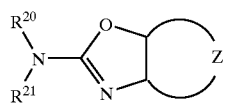

Each of $R^{20}$ and $R^{21}$ are independently selected from the group consisting of hydrogen, alkyl, and aryl; or $R^{20}$ and $R^{21}$, together with the nitrogen to which they are bonded, represent a 3–8 membered nonaromatic heterocyclic group. Z, when taken together with the carbons to which it is bonded, represents a optionally substituted 4–10 membered cycloalkyl ring (e.g. a cyclohexane ring, a cyclopentane ring, a cyclohex-3-ene ring (fused in the 1,2 position), a 4-hydroxycyclohexane ring (fused in the 1,2 position), etc.) or an optionally substituted nonaromatic heterocyclic group (e.g., a tetrahydrofuran ring (e.g., fused in the 2,3 position), a tetrahydropyran ring (e.g., fused in the 2,3 position), a tetrahydrothiophene ring (e.g., fused in the 2,3 position), a 4-hydroxytetrahydrofuran ring (e.g., fused in the 2,3 position), a 5-hydroxyalkyl- or 5-alkoxyalkyl-tetrahydrofuran ring (e.g., fused in the 2,3 position), and a 4-hydroxy-5-hydroxymethyltetrahydrofuran ring (fused in the 2,3 position)). Specific examples of allosamizolines include those compounds having the formulae:

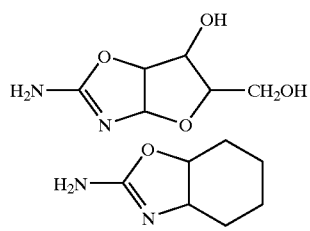

Allosamizolines of the types discussed above can be obtained commercially, for example from Salor, Milwaukee, Wis. or from Maybridge Chemical Company Ltd., Trevillett, Tintagel, Cornwall TL34 OHW United Kingdom.

"Barbituric acids", "1,3,5-triazinane-2-thiones", "N-substituted-phenylcarbamates", and "allosamizolines", as used herein, are meant to include their respective salts, hydrates, and the like. For example, the above-described salts can be pharmaceutically acceptable salts (e.g., salts formed with hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic, and the like). Other inhibitors identified using these screening methods include those having the following structural formulae:

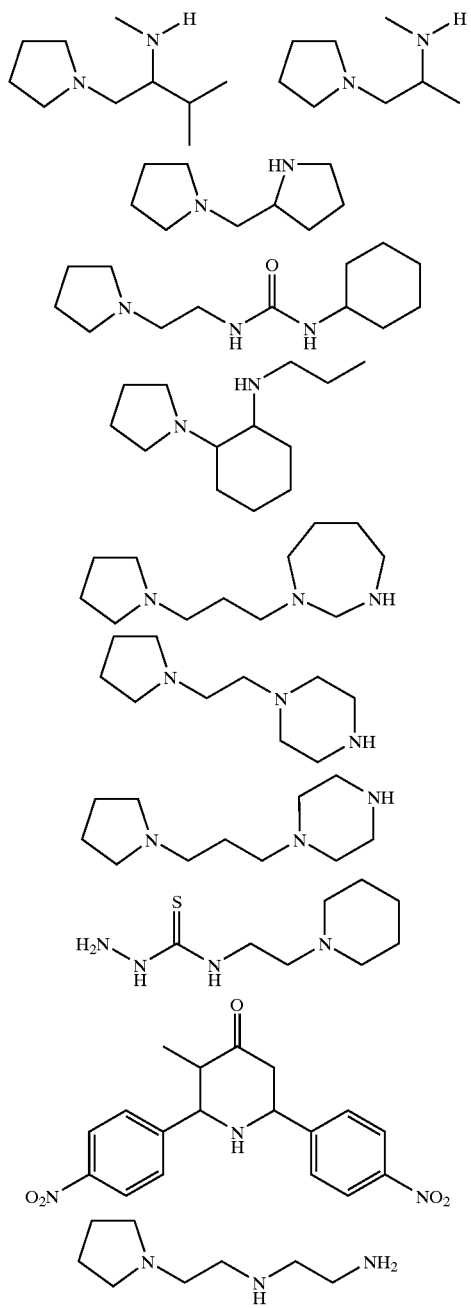

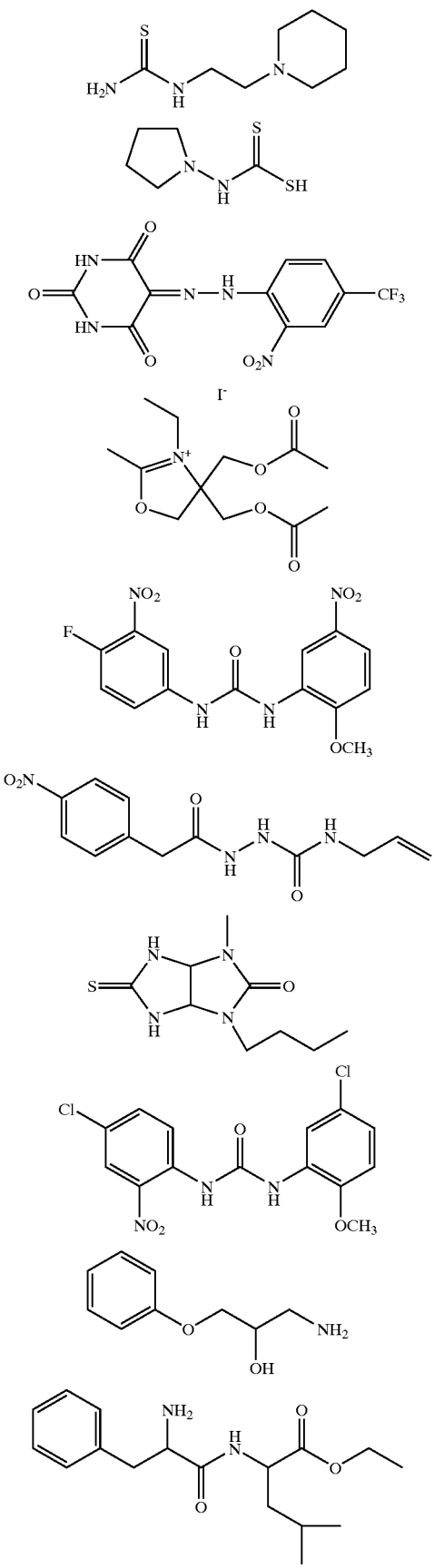

as well as their salts and hydrates, as discussed above.

The above described barbituric acids, 1,3,5-triazinane-2-thiones, N-substituted-phenylcarbamates, allosamizolines, and other potentially useful *chitinase* inhibitors may exist in various isomeric, tautomeric, stereoscopic, and diasteriomeric forms, all of which are meant to be encompassed by the formulae set forth above. Moreover, each of "barbituric acids", "1,3,5-triazinane-2-thiones", "N-substituted-phenylcarbamates", and "allosamizolines" is meant to include compounds that are isomerically, tautomerically, stereoscopically, and/or diasteriomerically pure as well as mixtures of such isomeric, tautomeric, stereoscopic, and diasteriomeric forms.

Other potential inhibitors of *chitinase* can be identified by using SYBYL to construct a homology model of the PfCHT1 active site and then by using a computer docking program (such as DOCK 4.0 or those described in Bugg et al., Scientific American, pages 92–98 (December 1993); West et al., TIPS, 16:67–74 (1995); and Dunbrack et al., Folding & Design, 2:27–42 (1997), which are hereby incorporated by reference) to search a database, such as the Available Chemical Database ("ACD") for candidate *chitinase* inhibitors. Once potential inhibitors of *chitinase* are identified, they can be tested using conventional enzyme inhibition assays. $IC_{50}$'s on the order of mM to $\mu$M (e.g., about 0.8 to about 2.3 mM) indicate that an inhibitor is particularly effective. Alternatively, other potential inhibitors of *chitinase* can be identified by producing crystals of purified PfCHT1 that are suitable for x-ray crystallographic studies, infiltrating candidate *chitinase* inhibitor compounds into the crystal, and analyzing the resulting complex by x-ray crystallography. Still alternatively, candidate *chitinase* inhibitors can be infiltrated into the crystal during the crystallization process, and the resulting complexes analyzed by x-ray crystallography.

The *chitinase* inhibitors described above can be used to prevent malaria transmission; to prevent and treat fungal diseases caused by, for example, *Pneumocyctis carinii, Histoplasma capsulatum, Cryptococcus neoformans, Coccidioides immitis, Candida* spp.; to prevent and treat human parasitic diseases including those caused by filaria spp., *Cryptosporidium parvum, Toxoplasma gondii*, and other apicomplexans, *Microsporidium* spp., *Leishmania* spp., *Trypanosoma* spp., *Giardia lamblia*, and *Entamoeba histolytica*; and to prevent and treat veterinary diseases caused by, for example, coccidan parasites, such as *Babesia* spp. and *Theileria* spp. The *chitinase* inhibitors described above can also be used to control, reduce, or eliminate arthropod pests of agricultural and human public health importance as well as veterinary arthropod parasites, such as fleas. The inhibitors can be used, for example, by placing them in areas that are known to be breeding grounds or other areas of infestation of the above described pests (e.g., kennels for fleas) or by placing them in areas that are known habitats of animals known to transmit (e.g., be carriers of) such pests and diseases (stagnant water for malaria-carrying mosquitos).

In addition to chemical inhibitors, peptide inhibitors could also be identified with screening methods (for example, using phage display libraries and other peptide screening methods).

Levels of functional *Plasmodium* sp. *chitinase* could also be modified by use of molecules which bind to transcription regulators of the *chitinase* gene (such as the promoter region of the gene).

In the context of this invention "modulation" or "modifying" generally means inhibition. This modulation can be measured in ways which are routine in the art, for example by Northern blot assay of mRNA expression or Western blot assay of protein expression.

The compounds and/or inhibitors used in the methods of the subject invention encompass any pharmaceutically acceptable salts, esters, or salts of such esters, or any other compound/inhibitor which, upon administration to a subject, is capable of providing (directly or indirectly) the biologically active metabolite or residue thereof. Accordingly, for example, the disclosure is also drawn to prodrugs and pharmaceutically acceptable salts of the compounds and/or inhibitors used in the subject invention, pharmaceutically acceptable salts of such prodrugs, and other bioequivalents.

In regard to prodrugs, the compounds and/or inhibitors for use in the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions.

In regard to pharmaceutically acceptable salts, the term pharmaceutically acceptable salts refers to physiologically and pharmaceutically acceptable salts of the compounds and/or inhibitors used in the subject invention: i.e., salts that retain the desired biological activity of the parent compound and do not impart undesired toxicological effects thereto.

Peptide inhibitors of *chitinase* can be identified by other methods also. For example, a monoclonal antibody can be prepared which specifically hybridizes to the *chitinase* protein, thereby interfering with activity. Once a monoclonal antibody which specifically hydridizes to the *chitinase* protein is identified, the monoclonal (which is itself a compound or inhibitor which can be used in the subject invention) can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305–318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305–318 (1988); Cwirla, S. E., et al., Proc Natl Acad Sci USA 87:6378–6382 (1990); Scott, J. K. & Smith, G. P., Science 249:386–390 (1990); Christian, R. B., et al., J Mol Biol 227:711–718 (1992); Smith, G. P. & Scott, J. K., Methods in Enzymology 217:228–257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305–318 (1988); Scott, J. K., Trends in Biochem Sci 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes the *Plasmodium* sp. *chitinase* can be identified. The sequences of these mimotopes represent short peptides which can then be used in various ways, for example as peptide inhibitors that bind to the *chitinase* and decrease the activity of the *chitinase*. Once the sequence of the mimotope is determined, the peptide inhibitors can be chemically synthesized.

Materials and Methods

A. *Plasmodium Gallinaceum*

Preparation of *P. gallinaceum* Ookinete *Chitinase*. The 8A strain of *P. gallinaceum* was used to infect 4–6-week-old White Leghorn chickens. A gametocyte-producing line was maintained by subpassage in chickens and periodic passage through mosquitoes. Ookinetes were cultured from purified zygotes in serum-free and protease-free M199 culture medium as described previously (Kaushal and Carter 1984). Preparations routinely yielded $5-15 \times 10^7$ ookinetes per 5 chickens, with transformation efficiencies of 50–90%. Twenty four to 30 h cultures of ookinetes were centrifuged, and the pellet and supernatants were pooled separately and frozen at 20° C. Extracts of ookinetes were prepared by addition of 20 mM sodium phosphate, pH 6.8, to the ookinete cell pellet, usually without protease inhibitors, followed by vigorous vortexing, three cycles of freeze-thawing (dry ice to room temperature), and sonication (6 cycles for 20 s on ice). For the experiment in which the time course of *chitinase* expression was determined with Western immunoblotting, a mixture of protease inhibitors was added directly to the fresh cell pellet in 20 mM sodium phosphate, pH 6.8 (2 mM AEBSF, 5 mM EDTA, 200 $\mu$M N-tosyl-L-phenylalanine chloromethyl ketone, 100 $\mu$M tosyl-L-lysine chloromethyl ketone, 1 mg/ml pepstatin, 2 mg/ml leupeptin, 2 mg/ml aprotinin, 1% Triton X-100). Pooled supernatants were 200-fold concentrated by centrifugal ultrafiltration (Centriprep 10, Amicon, Beverly, Mass.), dialyzed against 20 mM sodium phosphate, pH 6.8, and frozen at 20° C. until further use.

Protein Purification and *Chitinase* Detection. The high pressure liquid chromatography (HPLC) system consisted of a Thermoseparation Constametric Pump and a Spectromonitor 4100 UV detector (dual wavelength at 220 and 280 nm). The initial HPLC step consisted of 5.0 ml of pooled, dialyzed supernatants combined with soluble ookinete extracts injected into a quaternary ammonium anion exchange column (Q column) (Vydac 300VHP575. 0.75×5 cm, Hesperia, Calif.). Buffer A was 20 mM Tris, pH 8.0. Buffer B was 1 M NaCl in 20 mM Tris, pH 8.0. The gradient was developed over 30 min, from 100% Buffer A to 50% Buffer B at a flow rate of 1.0 ml/min. Fractions were collected at 1-min intervals. To individual wells of a 96-well black microfluorimetry plate (Microfluor B, Catalog #011-010-7205, Dynatek. Chantilly, Va.), 10 μl of each fraction was added to 160 μl of 20 mM Tris, pH 8.0, to which 30 μl of 4-methylumbelliferyl-N,N',N"-β-D-triacetylchitotrioside (4-MU GlcNAc$_3$) (Calbiochem, 125 μM solution in water) was added. Enzyme reactions were incubated at room temperature. A Dynatek Fluorolite 1000 (filters, excitation 365 nm and emission 450 nm) was used for kinetic fluorescence detection for 60 min.

*Chitinase*-containing fractions (those which produced linearly increasing fluorescence over the course of the kinetic assay) were identified, pooled, diluted 10-fold with saturated ammonium sulfate, pH 8.0 (to a total volume 5 ml), and injected into a Bio-Gel TSK-phenyl 5PW hydrophobic interaction column (Bio-Rad). Buffer A was 2 M ammonium sulfate with 20 mM Tris, pH 8.0. Buffer B was 20 mM Tris, pH 8.0. A gradient from 100% Buffer A to 100% Buffer B was developed over 30 min at a flow rate of 0.5 ml/min. For the anion exchange and hydrophobic interaction steps, *chitinase* activity was assessed without addition of any other buffers to the tested fractions and without changing the pH of the final solution before detection. Pilot experiments showed that *chitinase* activity was readily detectable in buffers with 10 mM to 1.5 M NaCl, and at pH 5.0 to pH 8.5 in 20 mM Tris.

*Chitinase*-containing fractions from the hydrophobic interaction HPLC were pooled, mixed with an equal volume of 50% acetonitrile, 0.1% trifluoroacetic acid, injected into a reverse-phase C-18 PRP Infinity column (Hamilton, Reno, Nev.), and eluted with a 10%–70% gradient of acetonitrile, 0.1% trifluoroacetic acid at a flow rate of 0.5 ml/min.

Amino-terminal Peptide Sequence Analysis. For purified, native, *P. gallinaceum* ookinete-produced *chitinase*, 10% of the volume of the acetonitrile fractions from the reverse-phase step was used to obtain amino-terminal sequence. Recovery of the purified protein from the sample tube was maximized by adding neat trifluoroacetic acid to a final concentration of 10%. One hundred percent of the recovered protein was applied to the biphasic column of a Hewlett-Packard G1005A (Palo Alto, Calif.), followed by a 1-ml wash with the manufacturer's sample loading solution. The purified protein was then subjected to automated Edman degradation using the manufacturer's recommended protocols and Chemistry Routine 3.5. For amino-terminal sequencing of endoproteinase Lys-C-treated rPgCHT1-NT1, the cleaved recombinant protein was run on SDS-PAGE, electroblotted to PVDF, stained with 0.05% Coomassie Blue in 40% methanol, 1% acetic acid, and destained with 50% methanol. The stained band was excised and submitted to automated Edman degradation on an Applied Biosystems 494/HT Procise Sequencing System in the University of Texas Medical Branch Protein Chemistry Core Facility.

Tryptic Digestion, HPLC Separation, and Microsequencing. To obtain amino acid sequence of internal tryptic peptide fragments, the remaining 90% of the acetonitrile fractions from the reverse-phase step was electrophoretically purified by SDS-PAGE. 50 μl of 2×SDS-PAGE sample buffer (Novex, San Diego, Calif.) was added to each 0.5-ml fraction from the reverse-phase step and concentrated by vacuum centrifugation (Hetovac, Heto Labs, Denmark). These fractions were size-fractionated by SDS-PAGE on a 4–20% gel (Novex), which was stained with Coomassie Blue R-250 (Bio-Rad) and destained for 4 h with Gel-Stain Destain Solution (Novex) with three changes of destaining solution. Stained bands were excised from the gel, rinsed twice with 50% acetonitrile in HPLC-grade water, and frozen on dry ice. Subsequent protein sequencing steps were performed at the Harvard University Microchemistry Laboratory (William Lane, Director, Cambridge, Mass.). The band was subjected to in-gel reduction, S-carboxyamidomethylation, and tryptic digestion (Promega) (Lane et al. 1991), and a 10% aliquot of the resultant mixture was analyzed. Sequence information was determined by capillary (180 μm×15 cm column, LC Packings, Amsterdam) reverse-phase chromatography coupled to the electrospray ionization source of a quadrupole ion trap mass spectrometer (Finnigan LCQ, San Jose, Calif.). The instrument was programmed to acquire successive sets of three scan modes consisting of full scan MS over the m/z 395–1200 atomic mass unit, followed by two data-dependent scans on the most abundant ion in that full scan. These data-dependent scans allowed the automatic acquisition of a high resolution (zoom) scan to determine charge state and exact mass and MS/MS spectra for peptide sequence information. The remainder (90%) of the peptide mixture was separated by microbore high performance liquid chromatography using a Zorbax C18 1.0×150 mm reverse-phase column on a Hewlett-Packard 1090 HPLC/1040 diode array detector. Optimum fractions were chosen based on differential UW absorbance at 205, 277, and 292 nm, peak symmetry, and resolution and then further screened for length and homogeneity by matrix-assisted laser desorption time-of-flight mass spectrometry on a Thermo BioAnalysis Lasermat 2000 (Hemel, UK). Strategies for peak selection, reverse-phase separation, and Edman microsequencing have been previously described (Lane et al. 1991). Tryptic peptides were submitted to automated Edman degradation of a Perkin-Elmer/Applied Biosystems 477A or Procise 494-HT protein sequencer (Foster City, Calif.). When possible, complementary Edman degradation data and MS/MS spectra were used to improve the final sequence interpretation.

Determination of DNA Sequence of *Chitinase* Gene and Non-translated Flanking Sequence. Degenerate oligodeoxynucleotides were designed based on the amino acid sequences of the following peptides (FIG. 2): GT29 (His to Lys) (SEQ ID NO:7: CA(T/C) TA(T/C) TA(T/C) AA(T/C) AA(C/T) ACI GA(T/C) TA(T/C) AAA), GT33 (Asn to Lys) (SEQ ID NO:8: AA(C/T) CCI GA(A/G) GT(A/C/T) CA(A/G) ACI CCI AAA), and GT84 (SEQ ID NO:9: CA(C/T) AA(A/G) CCI (C/T)TI GA(A/G) GTI GA(A/G) GA(A/G) C) (I represents inosine). Total RNA was isolated from 24-h post-exflagellation ookinetes with Trizol (Life Technologies, Inc.). First-strand CDNA synthesis, using 1 μg of total RNA, was prepared using the Capfinder system (CLONTECH, Palo Alto, Calif.). By using a Perkin-Elmer 9600 thermal cycler and Klen-Taq DNA polymerase (CLONTECH), the following polymerase chain reaction (PCR) cycling protocol was used: 94° C. for 3 min for 1 cycle; 94° C. for 30 s, 47° C. for 30 s, 68° C. for 3 min for 35 cycles; 4° C. on hold.

The full-length transcript was PCR-amplified using the ookinete first-strand cDNA prepared as described above as template (FIG. 2). To amplify the 5' end of the transcript, an antisense nondegenerate gene-specific oligonucleotide primer 2501 was synthesized (SEQ ID NO:10: GGG TTT TCA GTT ATA GTA AGG TC) based on the internal sequence of the PCR product generated by degenerate oligonucleotides derived from the amino acid sequences of GT84 and GT29; the 5' PCR primer from the Capfinder kit (SEQ ID NO:11: AAG CAG TGG TAA CAA CGC AGA GT) was used as the sense primer. Similarly, a sense nondegenerate gene-specific primer 2503 (SEQ ID NO:12: GAA AAA ATA TGC GAT GGG AAA GCA) was paired with the antisense cDNA synthesis primer (T30 SEQ ID NO:13: A/C/G A/C/G/T). The cycling protocol was as follows: 95° C. for 3 min for 1 cycle; then 95° C. for 30 s, 54° C. for 30 s, 68° C. for 3 min for 30 cycles; then 4° C. PCR products were ethanol-precipitated and resuspended in water. The DNA was phosphorylated and the ends made blunt (10 µl of 10× React 1 buffer (Life technologies, Inc.), 10 µl of 10 mM ATP, 2 µMl of 10 mM dNTP (dATP, dCTP, dGTP, dTTP), 10 units of T4 DNA polymerase, 10 units of T4 kinase, water to 100 µl, incubated at 37° C. for 60 min). The products of this reaction were electrophoresed and then purified from a Tris acetate/EDTA agarose gel using the Geneclean II kit (Bio 101, San Diego, Calif.). The DNA was ligated into pUC18 (SmaI-digested, bacterial alkaline phosphatase-treated, Amersham Pharmacia Biotech), electroporated (1.8 kV, 25 microfarads capacitance, 200 ohms resistance) (Gene Pulser, Bio-Rad) into electrocompetent DH10B E. coli (Life Technologies, Inc.), incubated in SOC (Life Technologies, Inc.) at 37° C. in a shaking incubator for 1 h, and plated on LB/ampicillin (100 µg/ml) plates. Plasmids from transformants were isolated by alkaline lysis (Wizard MiniPrep, Promega, Madison, Wis.). Clones containing the appropriately sized insert as determined by restriction analysis were sequenced using dye terminator reactions according to the manufacturer's instructions (DNA Sequencing Kit, Part Number 402079, Perkin-Elmer Applied Biosystems, Foster City, Calif.) and analyzed by an automated ABI sequencer (ABI Prism, 377 DNA Sequencer, Perkin-Elmer). Independent, cloned full-length genomic DNA and cDNA PCR products were sequenced in their entirety to verify the final sequence. Southern Blot Analysis. P. gallinaceum gDNA (10 µg) was digested with restriction enzymes DdeI, NcoI, EcoRI, and HindIII (Life Technologies, Inc.) in pairs as indicated in FIG. 3 and transferred to a nylon membrane (Hybond-N, Amersham Pharmacia Biotech). A 42-mer oligodeoxynucleotide probe (5 pmol) based on the coding sequence of the catalytic active site (SEQ ID NO:14: 645-T AAT GAT TTT GAT TTA GAT GGT GTA GAT ATT GAC TGG GAA CC-686) was end-labeled with [γ-$^{32}$P]ATP. After prehybridizing the membrane with 6×SSC, 0.1% SDS, 50 µg/ml heparin, 0.1% sodium pyrophosphate (Singh and Jones 1984), the blot was hybridized for 20 h at 45° C., washed sequentially with 6×SSC, 0.1% SDS at room temperature and 45° C., respectively, and finally washed with 1×SSC, 0.1% SDS at 45° C. and exposed to Kodak X-Omat AR film (Rochester, N.Y.) at 70° C. for 72 h.

Expression and Preparation of Recombinant PgCHT1. The NT1 form of rPgCHT1 PCR was amplified from a synthetic DNA template constructed in Escherichia coli-preferred codons (ECPC) (Operon, Alameda, Calif.). NT1 refers to the amino-terminal sequence of the larger of the two proteins in the purified 60-kDa *chitinase chitinase* doublet (FIG. 1*e*) that was determined by. Edman degradation analysis of the purified native protein. The sense primer used to make the rPgCHT1-NT1 construct was SEQ ID NO:15: GCG CCA TGG GTT ACG GTA GCT ATT GTG GCG; the antisense primer was SEQ ID NO:16: GCG CTC GAG TTG CAG CGG CAG GTC CAC (the Nco and XhoI sites, respectively, are underlined). PCR cycling conditions were 94° C.×6 min and then 18 cycles of 94° C.×30 s, 50° C.×30 s and then 68° C. for 1.5 min. The PCR product was digested and ligated into the NcoI and XhoI restriction sites of the expression vector pET32b. This vector expresses genes of interest as fusion proteins with a 105-amino acid thioredoxin leader sequence, amino- and carboxyl-terminal $His_6$ tags to facilitate purification by nickel-chelating chromatography, and an enterokinase cleavage site for removal of the amino-terminal fusion partner from the expressed protein. Transformants of the appropriate construct, verified by restriction enzyme analysis and automated sequencing of the construct in DH10B *E. coli* cells (Life Technologies, Inc.,), were then transfected into *E. coli* strain AD494 (DE3) (Derman et al. 1993) (Novagen, Madison, Wis.). The expression of rPgCHT1-NT1 in D494 (DE3) was further characterized by analyzing protein expression by Coomassie Blue-stained SDS-PAGE gels, Western immunoblotting, nickel-chelating chromatography, and assays of *chitinase* activity to demonstrate that protein of the appropriate size and activity was expressed.

Conditions for expressing protein for rPgCHT1-NT1 were as follows: 1) growth to A600=0.600 at 37° C. in a shaking incubator at 300 rpm; 2) addition of isopropyl-1-thio-β-D-galactopyranoside to 0.1 mM; 3) growth in a shaking incubator at 300 rpm at 18° C. for 16 h.

For enzymatic analysis of recombinant rPgCHT1-NT1, recombinant protein was partially purified in a single nickel-chelating chromatography step. Pellets of 2 liters of induced *E. coli* cells were pooled and resuspended in a lysis buffer of 20 mM Tris, 10 mM imidazole, 300 mM NaCl at 4° C., without the addition of protease inhibitors. The cell suspension was sonicated, centrifuged at 10,000×g, and then the supernatant was filtered through a 0.22-μm filter and batch-adsorbed to 1 ml of nickel-nitrilotriacetic acid (Ni-NTA)-agarose resin (Qiagen, Chatsworth, Calif.) at 4° C. Protein was eluted from the Ni-NTA beads with 250 mM imidazole in a buffer of 20 mM Tris, pH 8.0, 300 mM NaCl, after first washing with 10 column volumes of 10 mM and then 20 mM imidazole in the same buffer.

Protease Treatment of Recombinant NT1-PgCHT1. In triplicate, aliquots of rPgCHT1 were incubated with sequence grade endoproteinase Lys-C for 1 h at 23° C. (Roche Molecular Biochemicals) or recombinant enterokinase for 4 h at 23° C. Additional samples were heat-inactivated (10 min, 90° C.) or left untreated as controls. Amino-terminal protein sequencing was done in the University of Texas Medical Branch Protein Chemistry Core Facility using an Applied Biosystems 494/HT Procise Sequencing System.

Antibody Preparation and Immunoblotting. Two synthetic peptides were designed based on amino acid sequences found in the predicted open reading frame of the *P. gallinaceum chitinase* (numbered amino acids refer to FIG. 2): SEQ ID NO:17: 219-DLDGVDIDWEPHGK-232 (active site) and SEQ ID NO:18: 506-CDGKAAHYYNTDYKE-520 (carboxyl terminus). The peptides were chosen based on predicted antigenicity from a Kyle-Doolittle hydrophilicity plot. Peptide synthesis, carrier coupling, and structural analysis of the conjugates were performed by NIAID (Twinbrook Facility, Rockville, Md.). Peptide purity was verified by reverse-phase HPLC and mass spectroscopy. The peptides were coupled to keyhole limpet hemocyanin via the terminal cysteine (carboxyl-terminal peptide) or lysine (active site peptide). Molar coupling ratios of peptide:carrier, as determined by amino acid analysis, were 39 for the carboxyl-terminal peptide and 413 for the active site peptide.

Animal-use protocols for obtaining polyclonal mouse antisera were approved by the Animal Care and Use Committee, NIAID, National Institutes of Health. Mice were immunized according to the following schedule: each mouse received an intraperitoneal injection of 100 µg of conjugate emulsified in 100 µl of complete Freund's adjuvant (Sigma) for primary immunization, followed by 50 µg of conjugate emulsified in 100 µM of incomplete Freund's adjuvant three times at 3-week intervals.

For immunoblotting, proteins were separated on 4–20% SDS-PAGE gels (Novex) and electroblotted to nitrocellulose using the Novex Xcell BlotII module. After blocking with 5% dried skim milk in PBS, 0.05% Tween 20 (PBS-T), blots were incubated in primary polyclonal antisera at 1:1000 dilution in PBS, 0.05% Tween 20 for 1 h at room temperature. After three washes over 30 min with PBS-T, blots were incubated in secondary antibody (goat anti-mouse IgG heavy and light chain, alkaline phosphatase-conjugated, Kirkegaard & Perry Laboratories, Gaithersburg, Md.) at 1:5000 dilution in PBS, 0.05% Tween 20, for 1 h. After three washes over 30 min with PBS-T, the blots were developed in an alkaline phosphatase substrate (Western Blue, Promega, Madison, Wis.).

Analysis of *Chitinase* Activity. *Chitinase* activity of both native and recombinant *chitinases* was assessed in three ways. First, enzyme preparations were analyzed for their ability to degrade polymeric chitin, as described previously (Huber et al. 1991). Second, microfluorimetry (HTS7000, Perkin-Elmer, excitation 360 nm and emission 465 nm) was used to measure the hydrolysis of 4-MU GlcNAc, 4-MU GlcNAc$_2$, 4-MU GlcNAc$_3$, and 4-MU GlcNAc$_4$ (Sigma) as described previously. Initial enzyme reaction rates were measured. Enzymatic activity is reported as relative fluorescence units or fold change. Third, TLC was used to analyze the products of recombinant or ookinete-produced *P. gallinaceum chitinase* using native chitin oligosaccharides and synthetic 4-MU derivatives of chitin oligosaccharides as substrates. With native chitin oligosaccharides (GlcNAc$_{1-6}$, Calbiochem), 6 µl of 5 mM substrate was mixed with 4 µl of 5× citrate/phosphate, pH 3–7 (McIlvaine buffer), to which was added 10 µl of enzyme. The reaction mixtures were incubated at 37° C. overnight and then analyzed by TLC. 3 µl of the reaction mixture were applied to Silica Gel-60 TLC plates, 20×20 cm (EM Science, Gibbstown, N.J.) and chromatographed in isopropyl alcohol:ethanol:water (5:2:1). The plates were developed by spraying the plates with 10% sulfuric acid in ethanol followed by heating at 120° C. for 10–20 min to detect dark spots. The chromatograms were scanned on a flat-bed scanner and images processed using Adobe Photoshop 4.0 (Adobe Systems, Inc., San Jose, Calif.). Samples of enzyme reacted with synthetic 4-MU substrates (5 µl, containing 0.5 nmol of substrate/product) were applied to 10-cm Silica Gel-60 TLC plates following overnight incubation at 37° C. Products were separated as above. These chromatograms were visualized with a FLUOR-S imager using 366 nm excitation/456 nm emission filters (Bio-Rad).

Determination of pH Activity Profiles and Allosamidin Inhibition Curves. By using a citrate/sodium phosphate buffer with pH ranging from 3.0 to 7.0 in 0.5 pH unit increments, aliquots of enzyme were incubated with 4-MU GlcNAc$_3$ (100 µM). *Chitinase* reaction rates were analyzed by microfluorimetry. Allosamidin (Eli Lilly-and Co., Indianapolis) was made as a 2 mg/ml stock in water and diluted.

Computer Analysis. Analysis of DNA sequences was performed using the Lasergene set of programs (DNASTAR, Madison, Wis.). Homology searches were performed with gapped BLAST, with further profile analysis performed with PSI BLAST. The multiple alignments were generated using the GIBBS sampling procedure. The signal sequence was predicted using the algorithm of von Heijne (Nielsen et al. 1997).

B. *Plasmodium Falciparum*

Chemicals and Reagents. Routine chemicals were from Amresco (Euclid, Ohio) or Sigma. Molecular biology reagents were from Life Technologies (Gaithersburg, Md.). 4-Methylumbelliferone (4MU) substrates were from Sigma. Native chitin oligosaccharides (GlcNAc$_{1-6}$) were from Calbiochem.

Identification, Cloning, and Sequencing of PfCHT1. Sense and antisense primers derived from PfCHT1, spanning nucleotides 154–178 and 546–570, respectively, were used to generate a 417-bp digoxigenin (dig)-labeled probe by PCR, which was used to screen a phage library of *P. falciparum* genomic DNA (Thai isolate K1) (Goman et al. 1982). The probe contained the most highly conserved regions of the gene, including the substrate-binding and catalytic sites. Blots were developed by using an anti-dig detection system and chemiluminescence (Roche Molecular Biochemical, Indianapolis, Ind.). A HindIII fragment of DNA prepared from one positive plaque was subcloned into pUC19; this construct was called pUC19-4.2PfCHT1. The DNA sequence of PfCHT1 was established by automated sequencing.

Southern Blotting to Detect PfCHT1. Southern blots (containing 1 µg of *P. falciparum* 3D7 strain DNA per lane) were probed as described above by using the same 417-bp fragment. Final wash conditions were 2×SSC/0.5% SDS at 45° C.

Chromosomal Localization of PfCHT1. PCR, using two independent sets of PfCHT1-specific primers, was performed on individual chromosomes isolated from pulse-field electrophoresis-separated *P. falciparum* (XP5 clone; a progeny of the HB3×Dd2 genetic cross) as described (Su and Wellems 1999).

Expression and Preparation of Recombinant *P. falciparum Chitinase*. The expression construct was prepared by PCR-amplifying the native coding region of PfCHT1 using pUC19-4.2PfCHT1 as template. The NcoI-containing 5' primer was SEQ ID NO:19: GCG CCA TGG GTC ATC GAG CAC GAC CAG GTG AA. The XhoI-containing 3' primer was SEQ ID NO:20: CGCG CTC GAG ATG TAA AGA TTC TAC GAA ATA TTC. The construct began immediately after the predicted signal peptide cleavage site (Nielsen et al. 1997). PCR products were restriction-digested, ligated into the NcoI and XhoI restriction sites of the pET32b expression vector (Novagen), and transfected into DH10B *Escherichia coli* cells (Life Technologies). The correct construct was verified by restriction digestion and automated sequencing and used to transform the *E. coli* strain AD494 (DE3) (Novagen) for expression. Recombinant bacteria were grown in a fermentation system (BioFlo IV; New Brunswick Scientific), in LB with ampicillin at 100 µg/ml, as follows:(i) growth to OD$_{600}$=0.800 at.37° C.; (ii) addition of isopropyl β-D-thiogalactoside to 0.1 mM; and (iii) growth at 18° C. for 16 hr. Pellets were treated with 3 ml/g pellet of lysozyme (0.5 mg/ml) in 20 mM Tris, pH 8.0/200 mM NaCl/0.1 mM PMSF-and stirred at 22° C. for 20 min. Triton X-100 was added to a final concentration of 0.1% (vol/vol), the mixture was incubated for 5 min at 22° C., and 0.1 g/ml DNase I was added with a further 10-min incubation. The cell suspension was-centrifuged at 30,000×g for 1.5 hr, and the supernatant was directly run over a nickel-Sepharose column (AKTA Explorer System; Pharmacia). Recombinant PfCHT1 (rPfCHT1) was cleaved with recombinant enterokinase (Novagen) and amino-terminal sequencing of the PfCHT1 product done in the University of Texas Medical Branch Protein Chemistry Core Facility with an Applied Biosystems 494/HT Procise Sequencing System.

Assessment of *Chitinase* Activity. rPfCHT1 activity was assayed in glycol chitin gels by microfluorimetry and by TLC.

Determination of Substrate Specificity, pH Profile, and Allosamidin Inhibition Curves. Using a citrate/sodium phosphate buffer system with pH ranging from 4.0 to 7.0 in 0.5 pH unit increments, rPfCHT1 was incubated with native chitin oligosaccharides (GlcNAc$_{1-6}$) or 4MU-labeled GlcNAc$_{1-4}$ substrates and analyzed by TLC or microfluorimetry. Microfluorimetry results are reported as initial rates of substrate hydrolysis in relative fluorescence units.

Detection of PfCHT1 Transcripts in Mosquito Midgut Stages. *P. falciparum* sexual stages were produced by feeding infectious gametocytes (3D7 clone) to *Anopheles freeborni* (Templeton et al. 1998). Mosquito midguts containing ookinete stages were collected 24 hr postfeed. Total RNA was extracted from a pool of 70 midguts by using Trizol (Life Technologies). After treatment with DNase I, first-strand cDNA was generated by using a mixture of oligo(dT) and random hexamers. PCR amplification was performed in the presence or absence of reverse transcriptase (Superscript Preamplification System; Life Technologies) to control for genomic DNA contamination. Amplification of PfCHT1 was performed by using the primers SEQ ID NO:21: 5' ATT ATG CTT TTA TCT CTT GGA GG and SEQ ID NO:22: 5' AGT CTT TAC AAA ATC ACC AAT GG. As a control, a fragment of the *P. falciparum* gene, Pfs28, expressed by retort and ookinete stages in the mosquito midgut (Duffy and Kaslow 1997), was amplified by using the primers SEQ ID NO:23: 5° CAT AAC GTT GAA TAA GGC TCG GG and SEQ ID NO:24: 5' CTA TAT GAT GTA TCA GCC TGG TCC.

Molecular Modeling of PfCHT1. Homology models were constructed by using sequence alignment and energy was minimized by using SYBYL (Tripos Associates, St. Louis). The atomic coordinates of hevamine complexed with allosamidin (Protein Data Bank Code 1LLO) and *Serratia marcescens chitinase* Chi A (Protein DataBank Code 1CTN) were used as templates.

EXAMPLE I

Figure 1E:
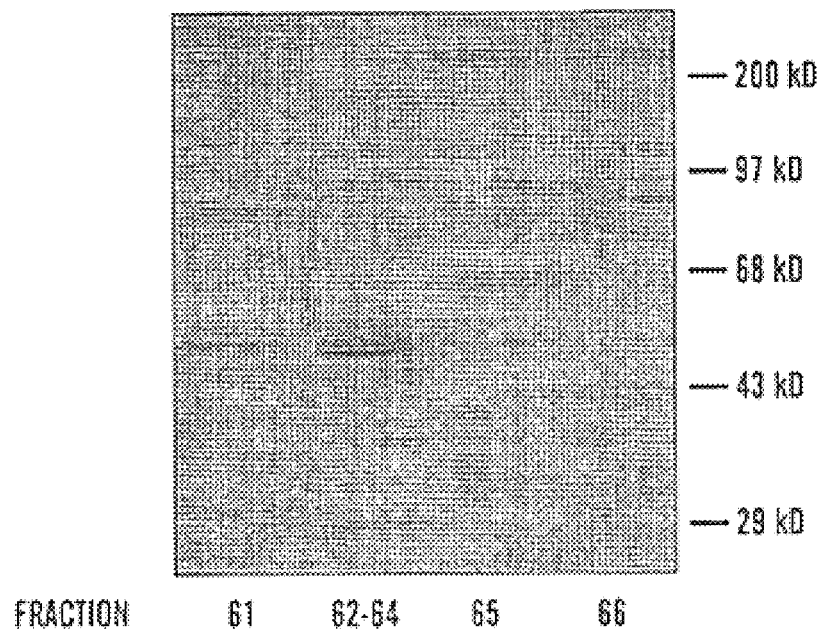

Purification and Microsequencing of the *P. gallinaceum* 60-kDa *Chitinase* Protein. A mixture of supernatants and soluble extracts of 2×10$^9$ *P. gallinaceum* ookinetes was sequentially subjected to anion exchange, hydrophobic interaction, and reverse-phase HPLC (FIGS. 1a–1e). 4-MU GlcNAc$_3$ was used as the substrate for following endochitinase activity through the anion exchange and hydrophobic interaction steps; acetonitrile/trifluoroacetic acid in the reverse-phase step irreversibly disrupted the *chitinase* activity. Coomassie Blue staining of the major peak (fractions 62–64) in the final purification step showed an apparently pure doublet with apparent molecular mass of 60 kDa (FIG. 1e). Fractions 62–64 contained a 60-kDa protein doublet; fractions 65–66 contained a single 60-kDa protein and a 210-kDa protein. The 60-kDa doublet was suspected to be a *chitinase* for two reasons as follows: most reported family 18 *chitinases* are between 35- and 80-kDa molecular mass; and polyclonal antisera raised to a synthetic peptide derived from the active site of the *Entamoeba histolytica chitinase* recognize an ookinete stage-specific 60-kDa doublet (Vinetz and Kaslow 1998). When an aliquot of pooled fractions 62–66 was subjected to immunoblot analysis, antisera to the *E. histolytica chitinase* active site recognized the 60-kDa doublet in fractions 62–64 and the 60 and 210-kDa proteins in fractions 65–66.

Ten percent of the pooled reverse-phase fractions 62–64 was analyzed by direct amino-terminal sequencing. The remaining 90% was lyophilized in the presence of SDS, subjected to SDS-PAGE, and stained with Coomassie Blue. The purified doublet was excised from the gel and subjected to microsequencing.

Direct Edman degradation of an aliquot of pooled fractions 62–64 (FIG. 1e; 5 pmol of protein as determined by amino acid analysis) showed two distinguishable amino-terminal sequences (amino-terminal 1 and amino-terminal 2, FIG. 3). Three peptides, GT29, GT33, and GT84 (FIG. 3), were produced by in situ trypsin digestion of the purified protein doublet and isolated by reverse-phase HPLC; these protein fragments were further analyzed by mass spectroscopy and Edman degradation.

EXAMPLE II

Figure 2:
FIG. 2 illustrates the cloning strategy of PgCHT1 cDNA. Reverse transcriptase PCR was performed using as template first strand cDNA (prepared with the Capfinder system; see Materials and Methods) synthesized from *P. gallinaceum* ookinete total RNA and degenerate oligonucleotide primers based on the amino acid sequences of GT29 and GTB4, as indicated by arrowheads within rectangles. The resulting PCR product was cloned and sequenced, from which the non-degenerate PCR primers 2503 and 2501 were designed. Primer 2501 paired with the Capfinder 5' oligonucleotide primer and Primer 2503 paired with the oligo(dT) primer (see Materials and Methods for primer sequences) were used for two separate PCR reactions using first strand ookinete cDNA as template. A single product was obtained with the primer pair 2501×5' PCR primer; this PCR product was cloned and sequenced. Several discrete bands were obtained with the primer pair 2503×oligo(dT); only the largest of these bands was cloned and sequenced. The sequences of these two reverse transcriptase-PCR products overlapped and gave rise to the full-length 2508-bp cDNA of PgCHT1 (GenBank™ accession number AF064079)
Figure 4A:
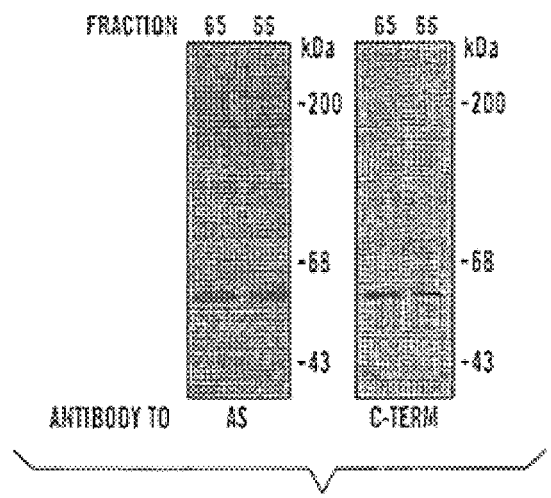
FIGS. 4a–4c show the different forms of *P. gallinaceum* ookinete-produced *chitinase* and time course of expression.
Figure 4B:
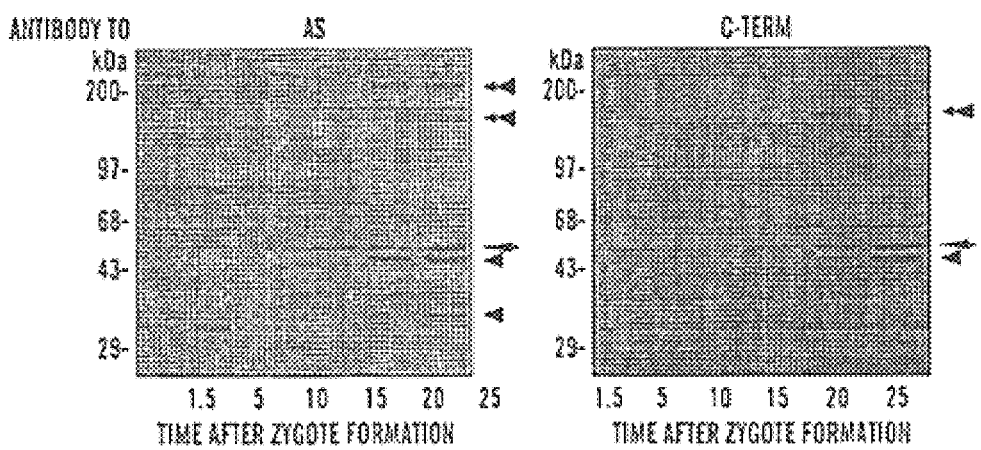
Figure 4C:
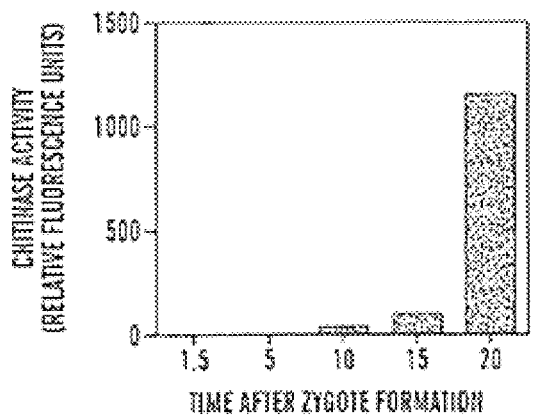

Determination of the DNA Sequence of the *P. gallinaceum Chitinase* Gene, PgCHT1, That Encodes the 60-kDa *Chitinase*. Degenerate oligodeoxynucleotide primers were synthesized based on the tryptic peptide sequences GT33, GT29, and GT84. PCR, using first-strand cDNA of mature *P. gallinaceum* ookinetes as template and the pairing of degenerate oligodeoxynucleotide primers GT33 with GT29 and GT29 with GT84, respectively, generated single products that were cloned and sequenced. These PCR fragments encoded amino acid sequences without recognizable homology on BLAST search. Nondegenerate gene-specific oligodeoxynucleotides, synthesized based on the internal sequences of these PCR products, were used as primers in two separate PCR reactions; these reactions used first-strand cDNA of mature *P. gallinaceum* ookinetes, prepared with the CLONTECH Capfinder system as template (FIG. 2). The first PCR reaction used the CLONTECH 5' Capfinder PCR primer and a gene-specific antisense 3' primer; similarly, the second PCR used the oligo(dT) primer as the 3' antisense primer and a gene-specific 5' sense primer. When amplifying the 5' end of the CDNA template, a single band was obtained, cloned, and sequenced; when amplifying the 3' end, several bands were obtained, and only the highest molecular weight band was cloned and sequenced. These two sequences (using PCR primers to cross the overlap between the two gene-specific primers) were combined to produce a 2508-bp cDNA corresponding to the full-length mRNA transcript from the initiation of transcription to the poly-adenylation tail (GenBank™ accession number AF064079). FIG. 3 depicts the full-length translated open reading frame. The two amino-terminal sequences of the purified 60-kDa doublet determined by direct Edman degradation and the amino acid sequences of tryptic digest fragments GT29, GT33, and GT84 of the 60-kDa doublet were all found in the amino acid sequence encoded by PgCHT1.

PCR products derived from either gDNA or cDNA as template had the same size and sequence, demonstrating that the open reading frame was a single exon. A Southern blot of *P. gallinaceum* gDNA probed with a 42-mer oligodeoxynucleotide probe directed against the active site was consistent with a single or low copy number copy gene.

EXAMPLE III

Analysis of the Primary Structure of the Encoded *P. gallinaceum* Chitinase. The cloned cDNA PCR product representing a full-length *chitinase* cDNA contains 275 bp of untranslated sequence at the 5' end, a 1761-bp open reading frame encoding 587 amino acids with a predicted molecular mass of 67,927 Da (FIG. 3), and 432 bp of untranslated sequence at the 3' end. Although a Kozak consensus sequence (Kozak 1987) is not present at the presumptive site of the initiation of transcription, a consensus sequence AAA(A/A)TG at the predicted transcriptional start site typical of *Plasmodium* spp. is present (Saul and Battistutta 1990). A secretory signal sequence of 22 amino acids is predicted, followed by a 42-amino acid lysine/asparagine-rich precursor region not found in the enzymatically active, purified 60-kDa *chitinase* doublet. Amino-terminal sequences 1 and 2 are colinear near the amino terminus. The two forms of the purified *chitinase* are predicted to be of molecular mass 60,595 and 59,117 Da, respectively, similar to the apparent molecular masses observed for the protein doublet on SDS-PAGE (FIG. 1*e*).

BLAST search with the full-length *P. gallinaceum* amino acid sequence revealed homologies to numerous other *chitinases*; similarities were limited to the substrate binding and catalytic active site motifs. On searching the *P. falciparum* chromosome 14 genome data base, a partial sequence of a *P. falciparum* gene encoding a family 18 glycohydrolase catalytic domain was found. This *P. falciparum* fragment was approximately 1000 bp and encoded motifs characteristic of the substrate-binding and catalytic active sites of family 18 glycohydrolases (Henrissat and Davies 1997). This *P. falciparum chitinase* has been further characterized (see Examples which follow). The substrate-binding site (amino acids 187–194) contains the consensus sequence SEQ ID NO:25: XXXSXGG, where X represents hydrophobic amino acids, except at the amino-terminal end where there is an unusual non-conservative isoleucine substitution for a lysine. Both *Plasmodium chitinases* are typical of family 18 glycohydrolases, with one exception: uniquely the *Plasmodium chitinases* lack a highly conserved tyrosine (or a conservative change such as phenylalanine) at position 229. A putative chitin-binding domain is present that, although not sharing significant amino acid sequence similarity with chitin-binding domains of any eukaryotic *chitinases*, has significant secondary structural homology to bacterial chitin-binding domains.

EXAMPLE IV

Analysis of Different Formns of *P. gallinaceum Chitinases* and Time Course of Expression. To confirm further that the *P. gallinaceum* gene sequence determined above encoded the purified 60-kDa doublet that was identified as a *chitinase*, antisera for use in Western immunoblots were prepared to synthetic peptides consisting of the catalytic active site and a peptide near the carboxyl terminus (FIG. 3). Antibody specificity of antisera raised against the synthetic peptides derived from the *P. gallinaceum* 60-kDa *chitinase* was confirmed by Western immunoblotting *P. gallinaceum* zygotes and ookinetes with immune and preimmune sera against both synthetic peptides; immune sera recognize proteins in ookinete but not zygote extracts (see below), whereas preimmune sera do not detect any proteins in the same preparations. Western immunoblot of purified *chitinase* (fractions 65 and 66 from FIG. 1*e*) with antisera to the carboxyl terminus detects only the 60-kDa doublet (FIG. 4*a*, right panel). Unexpectedly, antisera to the catalytic active site recognize, in addition to the 60-kDa doublet, a 210-kDa protein (FIG. 4*a*, left panel). This latter result suggests that the 210-kDa protein may lack the carboxyl-terminal epitope present in the putative chitin-binding domain of the 60-kDa doublet. The 60-kDa doublet and the 210-kDa protein co-eluted through a multiple step purification protocol (FIG. 1*e*), suggesting the possibility that *P. gallinaceum* ookinetes secrete at least two structurally related forms of *chitinase*, a 60-kDa doublet and a 210-kDa protein.

*P. gallinaceum* ookinetes produce a number of proteins (210-, 160-, 66-, 60-kDa doublet, 35-kDa) that are stage-specifically expressed in mature ookinetes and are not present in zygotes, as determined by analysis with Western immunoblot; all of these proteins react with antisera raised to a synthetic peptide derived from the active site of PgCHT1 (FIG. 4*b*, left panel). This antiserum lacked reactivity to *P. gallinaceum* zygote extracts (FIG. 4*b*, left panel) and non-recombinant *E. coli* extracts. Only a subset of these bands (160-, 66-, and 60-kDa doublet) react with antisera directed against the carboxyl-terminal region (FIG. 4*b*, right panel); the 66-kDa band (thin arrow) is the precursor to the 60-kDa doublet as shown by Western immunoblot of ookinete extracts with antisera raised to a synthetic peptide from the region between the signal peptide and the NT1 cleavage site. The appearance of these bands correlates in with the appearance of *chitinase* activity during the development of zygotes to ookinetes (FIG. 4*c*), consistent with the hypothesis that these bands are those of *chitinases*.

EXAMPLE V

*P. gallinaceum* Ookinetes Produce at Least Two Chromatographically and Immunologically Distinct *Chitinases*. Initially, only one broadpeak of endochitinase activity was isolated by anion exchange chromatography of *P. gallinaceum* ookinete extracts. When a slower flow rate and more gradual salt gradient were used to chromatograph ookinete extracts by strong anion exchange HPLC, two peaks of endochitinase activity (hereafter referred to as peak 1 and peak 2), as assessed by hydrolysis of 4-MU $GlcNAc_3$ were reproducibly resolved (FIG. 5*a*).

The separate peaks of *chitinase* activity were concentrated, subjected to SDS-PAGE under both reducing and non-reducing conditions, and Western immunoblotted using antisera that recognize the catalytic active site and carboxyl terminus (FIGS. 5*b*–5*e*). Several proteins reacted with antibody to the active site of PgCHT1. Western immunoblot of peak 1 (fractions 35–37) with active site antisera demonstrated the 60-kDa *chitinase* doublet both under non-reducing (FIG. 5*b*) and reducing (FIG. 5*d*) conditions. In addition, a 35-kDa protein in peak 1, of unknown function, reacted with the active site antisera. This 35-kDa protein is stage-specifically expressed in ookinetes, is not found in zygotes (FIG. 4*b*, left panel), and could be either a degradation product of another *chitinase* protein, the product of another *chitinase* gene, or simply an unrelated protein. Western immunoblot of peak 2 (fractions 42–44) with active site antisera demonstrated a predominant band of 210 kDa under non-reducing conditions (FIG. 5*b*) that, under reducing conditions (FIG. 5*d*), was not detected and was replaced by a 35-kDa protein. In addition, in fraction 42, a band of 160 kDa reacted with antiserum to the active site but not the carboxyl terminus (FIGS. 5*b*–5*e*). This 160-kDa protein is stage-specifically expressed in ookinetes and is not detectable in zygotes (FIG. 5*b*, both panels). Additional resolution of this second peak of *chitinase* activity with additional anion exchange chromatography and enzymatic analysis suggests that both the 210- and the 160-kDa proteins are

Figure 5B:
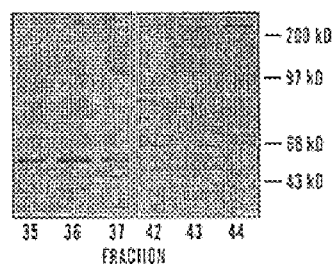
FIGS. 5a–5e show two chromatographically separable *chitinase* activities produced by *P. gallinaceum* ookinetes.
Figure 5C:
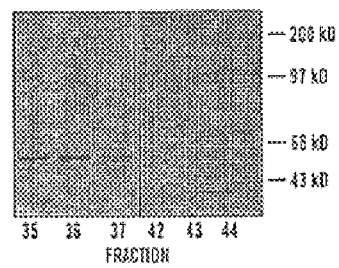
Figure 5A:
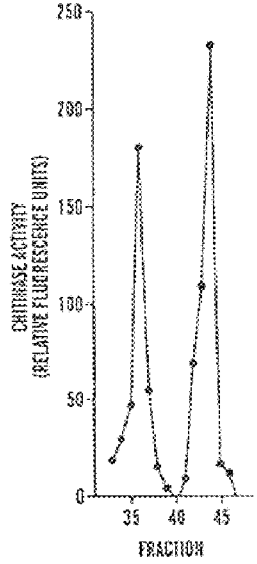
Figure 5D:
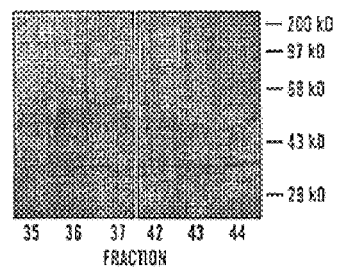
Figure 5E:
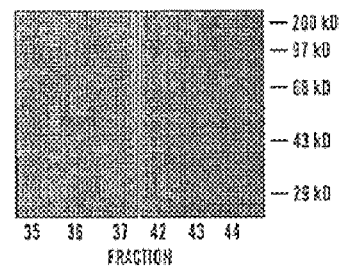
Figure 6A:
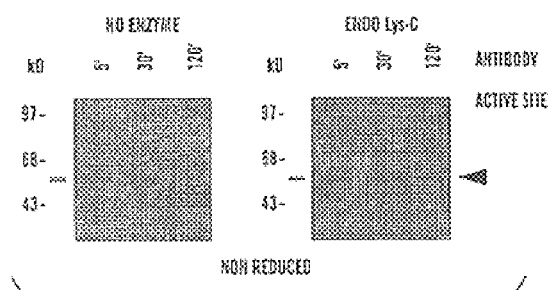
FIGS. 6a–6d show the effect of Endo Lys-C on *P. gallinaceum* ookinete-produced *chitinase*. Concentrated ookinete supernatants (from ~2×10$^7$ parasites per lane) were either treated with Endo Lys-C or buffer alone. Aliquots were taken for immunoblotting at 5, 30, and 120 min. An equal volume of 2× sample buffer with or without 10% β-mercaptoethanol was added to an aliquot of each fraction, and the samples were subjected to SDS-PAGE with a 16% polyacrylamide gel. After electroblotting, the blots were probed with active site or carboxyl terminus antiserum.
Figure 6B:
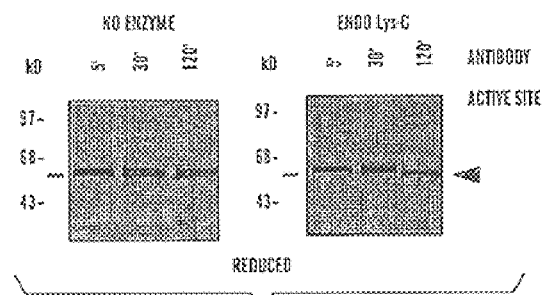
Figure 6C:
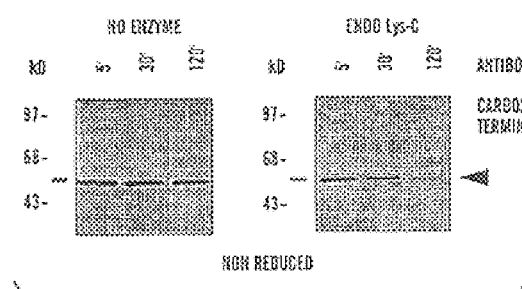
Figure 6D:
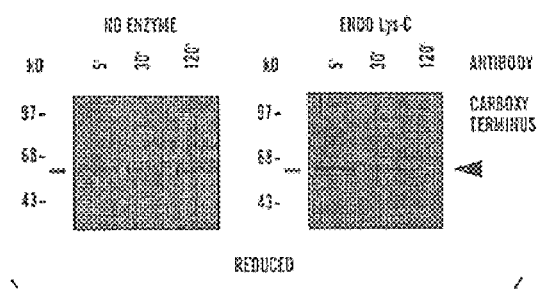

*chitinases*. The active site antisera-recognized both the 210- and 35-kDa bands, but the carboxyl-terminal antisera recognized neither (FIGS. 5b and 5c). This finding suggests that the carboxyl-terminal epitope is absent in the 210- and 35-kDa bands in the second peak of *chitinase* activity, as well as the 35-kDa protein in the first peak of *chitinase* activity.

EXAMPLE VI

Sites of Action of Endoproteinase Lys-C on the 60-kDa *P. gallinaceum* Chitinase. *P. gallinaceum* chitinase has been reported to be secreted as an inactive zymogen that mosquito midgut proteases activate to a fully active enzyme (Shahabuddin et al. 1993); this finding has become established in the literature (Shahabuddin et al. 1993; Shahabuddin 1998; Shahabuddin et al. 1996; Tellam et al. 1999). The serine protease endoproteinase Lys-C (Endo Lys-C) was reported to increase the *P. gallinaceum chitinase* activity in culture supernatants up to 13-fold. (Shahabuddin et al. 1993). To characterize further this phenomenon, Western immunoblotting of native, ookinete-secreted *chitinase* was used (FIGS. 6a–6d) and amino-terminal sequencing of Endo Lys-C-cleaved rPgCHT1 to delineate the sites where Endo Lys-C cleaves the 60-kba*P. gallinaceum chitinase*.

Concentrated ookinete supernatants were treated with Endo Lys-C and the reactions terminated with the serine protease inhibitor, AEBSF. It was found that *chitinase* activity, as assessed by 4-MU GlcNAc$_3$ hydrolysis, was unaffected by treatment with Endo Lys-C, in contrast to the results of others (Shahabuddin et al. 1993). Immunoblots were performed on the reaction mixtures, under non-reducing and reducing conditions, with polyclonal antisera to the active site- and carboxyl terminus-derived peptides (FIGS. 6a–6d). Endo Lys-C had two effects on the 60-kDa doublet as follows: 1) both bands of the doublet were cleaved, resulting in a single band running at a slightly smaller molecular mass than the bottom band of the doublet; and 2) a time-dependent disappearance of the carboxyl-terminal epitope occurred. Antisera to the active site demonstrated that a single full-length *chitinase* remained after Endo Lys-C treatment under non-reducing conditions. Under reducing conditions a small fragment was removed, resulting in a slightly faster migration of the processed *chitinase* (FIGS. 6a–6d, right top arrowhead). The precise epitope recognized by the carboxyl-terminal antisera, which demarcates the putative chitin-binding domain, contains a predicted Endo Lys-C site at $Lys^{509}$-$Ala^{510}$, consistent with the experimental findings. $Cys^{506}$, at the amino terminus of the epitope, may form a disulfide bridge with the only cysteine downstream from it, $Cys^{557}$ (FIG. 3).

Since Endo Lys-C converts the 60-kDa *chitinase* doublet to a slightly smaller single band, the amino-terminal site of action of this protease was determined. After treatment of rPgCHT1-NT1 with Endo Lys-C, the cleaved product was separated by SDS-PAGE, transferred to a PVDF membrane, and analyzed by Edman degradation. This analysis showed that Endo Lys-C cleaves rPgCHT1 on the carboxyl-terminal side of $Lys^{86}$, just downstream from the NT2 cleavage site (FIG. 3). Immunoblot of Endo Lys-C-treated rPgCHT1 with the anti-carboxyl-terminal antiserum showed loss of the epitope, similar to that found when native ookinete-produced 60-kDa *chitinase* was treated with Endo Lys-C (FIGS. 6a–6d).

EXAMPLE VII

Figure 7A:
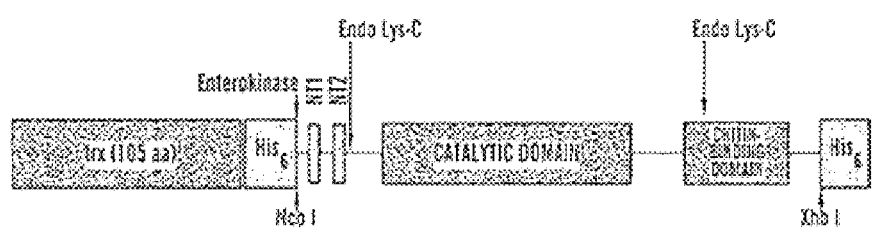
FIGS. 7a–7c show the expression of recombinant PgCHT1-NT1 and demonstrates that it is enzymatically active.

Expression of Recombinant PgCHT1. Numerous constructs of native codon-based PgCHT1, using different vectors expressed under a variety of temperature conditions and isopropyl-1-thio-β-D-galactopyranoside concentrations in *E. coli* host cells, did not produce more than ~5 μg of recombinant protein/liter-induced *E. coli* cells. Undetectable quantities of recombinant protein were obtained when attempting to express similar constructs in a well characterized *Saccharomyces cerevisiae* expression system (Kaslow and Shiloach 1994). Because the A+T codon bias of this gene (70.6%) was suspected to be the primary barrier to producing recombinant protein, a synthetic PgCHT1 gene was constructed using *E. coli*-preferred codons and used as a PCR template for making the rPgCHT1-NT1 construct (see Materials and Methods). Recombinant PgCHT1-NT1 (depicted schematically in FIG. 7a), expressed with a construct synthesized in *E. coli*-preferred codons and expressed in *E. coli* AD494 (DE3) cells, produced ~5–10 mg of recombinant protein/liter of induced cells, of which ~1–3% was soluble and active. Chitinase activity was readily detectable in crude soluble extracts of the cells. When the same constructs were expressed in *E. coli* BL21 (DE3) cells, no *chitinase* activity was detected, despite a comparable total quantity of protein produced. Western immunoblot analysis of protein obtained by a Ni-NTA purification step demonstrated that the eluted, soluble proteins were >90% PgCHT1. Approximately 20% of the soluble protein in eluted fractions was rPgCHT1-NT1 of the predicted length; the rest were aggregated and truncated forms of rPgCHT1.

EXAMPLE VIII

Figure 7B:
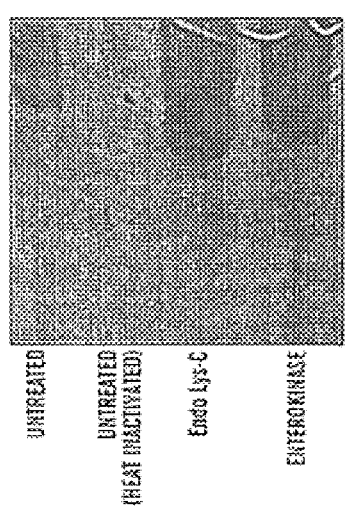
Figure 7C:
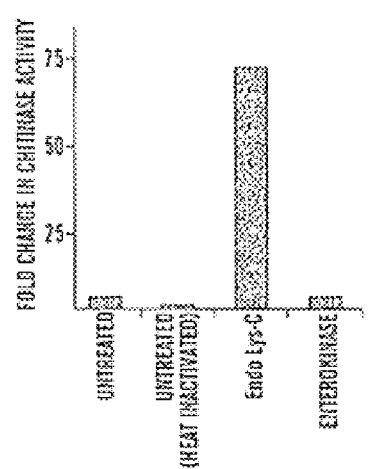
Figure 8:
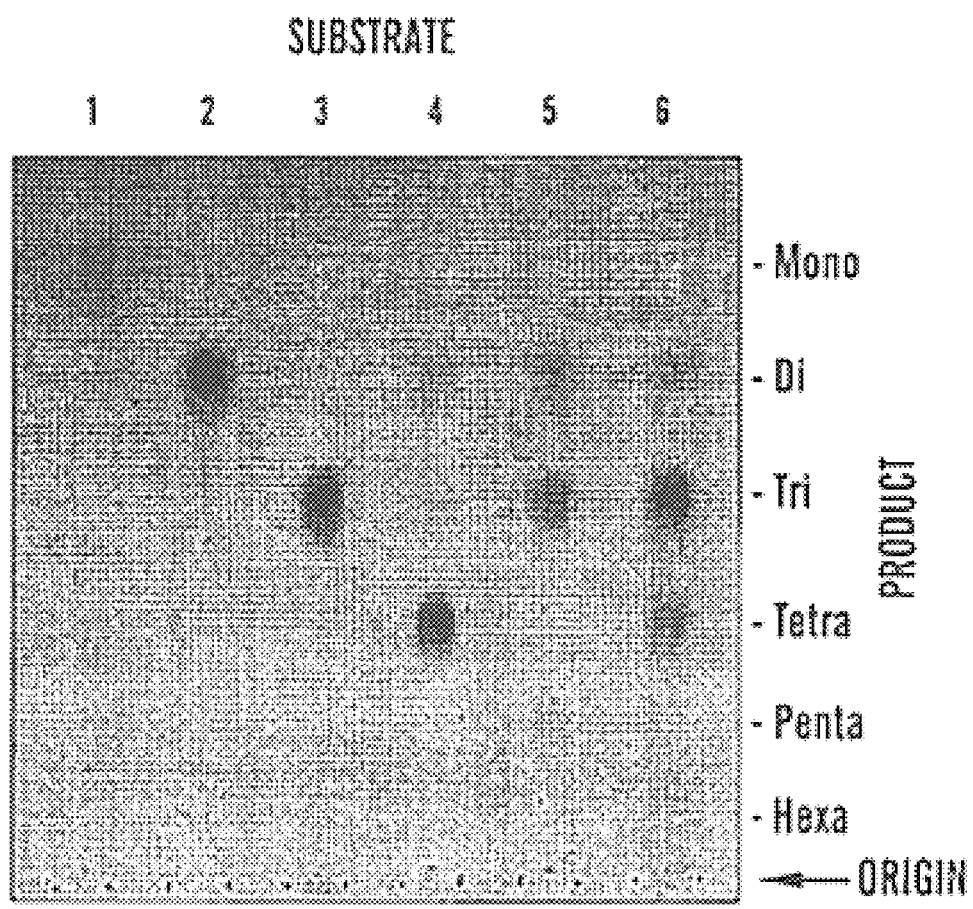
FIG. 8 shows thin layer chromatography analysis of native chitin oligosaccharide substrate preference of recombinant PgCHT1 and reaction products resulting from enzymatic hydrolysis. Substrate lengths GlcNAc$_{1-6}$ are indicated on top of the photograph. Reaction products are indicated on the right. The origins where the reaction mixtures were spotted are as indicated.
Figure 9A:
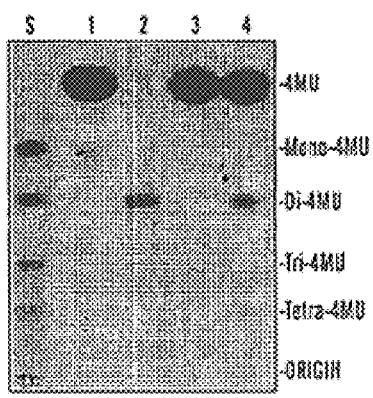
FIGS. 9a–9d show the analysis of activity of crude *P. gallinaceum* ookinete extracts and rPgCHT1 on 4-MU derivatives of chitin oligosaccharides.
Figure 9B:
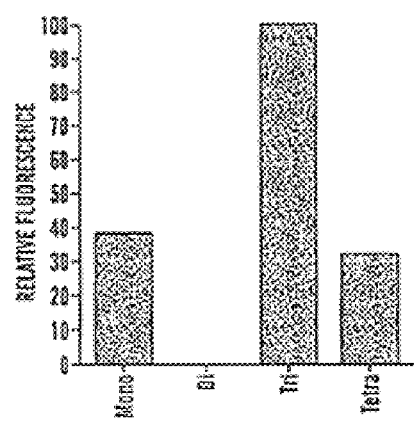
Figure 9C:
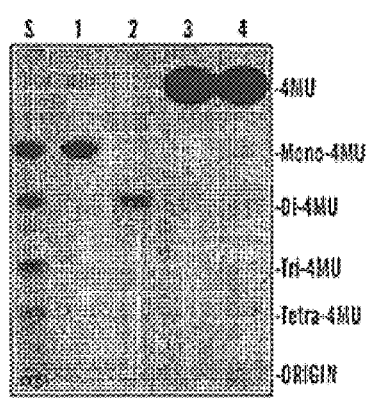
Figure 9D:
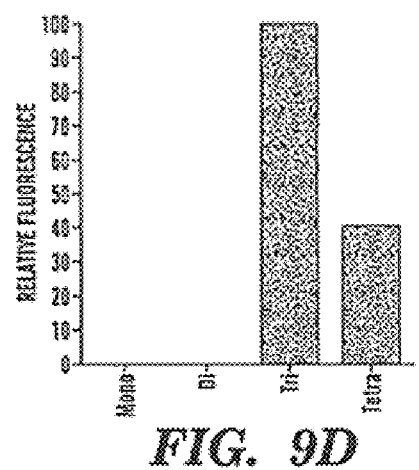

*P. gallinaceum* Chitinases Degrade Polymeric *Chitinase* and Have Identical Substrate Preferences and Reaction Product Profiles. A previous report demonstrated that several bands of chitinolytic activity were present in crude extracts and culture supernatants of *P. gallinaceum* ookinetes, as determined in a glycol chitin activity gel (Huber et al. 1991). rPgCHT1-NT1, whether or not treated with proteases, also degraded polymeric chitin in a glycol chitin activity gel (FIG. 7b); quantitation of chitin degradation was not possible from this experiment. As negative controls, Endo Lys-C alone and heat-inactivated rPgCHT1NT1 had no detectable *chitinase* activity in the activity gel. The ability of rPgCHT-NT1 to cleave 4-MU GlcNAc$_3$ was then assessed. When rPgCHT1-NT1 was treated with enterokinase to remove the thioredoxin fusion partner, there was no change in enzymatic rate of 4-MU GlcNAc$_3$ (FIG. 7c). However, to exploit the finding that Endo Lys-C cleaves PgCHT1 just downstream of the NT2 cleavage site, rPgCHT1 was treated with Endo Lys-C. This protease treatment increased *chitinase* activity 73-fold, using the 4-MU GlcNAc$_3$ substrate (FIG. 7c). As an additional control to show that the Endo Lys-C and enterokinase did in fact cleave the recombinant protein, Western immunoblot analysis performed before and after protease treatment demonstrated the appropriately sized cleavage products.

To characterize the substrate specificity and reaction product profiles of *P. gallinaceum chitinases*, the activities of ookinete-produced *chitinase* and rPgCHT1-NT1 were assessed with native chitin oligomers (FIG. 8) and 4-MU GlcNAc substrates (FIGS. 9a–9d). *P. gallinaceum* ookinete-produced *chitinase* (peak 1, peak 2, and unfractionated extracts) and rPgCHT1-NT1 had identical substrate preferences and reaction product profiles, with the exception that the crude extract had an N-acetylglucosaminidase activity not found in peak 1 or peak 2 of anion-exchanged chromatography fractionated ookinete extracts (FIGS. 8 and 9a–9d). Both parasite-produced *chitinase* and rPgCHT1-NT1 hydrolyzed 4-MU GlcNAc$_3$ and 4-MU GlcNAc$_4$ (FIGS. 9a–9d). Treatment of rPgCHT1-NT1 with Endo Lys-C had no effect on the pattern of substrates preferred by the enzyme nor on the reaction product profile. Regardless of whether rPgCHT1-NT1 was treated with Endo Lys-C, it did not hydrolyze 4-MU GlcNAc or 4-MU GlcNAc$_2$. The kinetics of Endo Lys-C-treated rPgCHT1-NT1 on 4-MU GlcNAc$_3$ and 4-MU GlcNAc$_4$ were analyzed. By using a Lineweaver-Burk plot, the Km values of Endo Lys-C-treated rPgCHT1 were determined to be 140 $\mu$M at pH 6.0 for 4-MU GlcNAc$_3$ and 100 $\mu$M at 6.0 for 4-MU GlcNAc$_4$. The Km values found for other recombinant and native *chitinases* are similar. For example, native and recombinant Brugia malayi *chitinase* has Km=40 $\mu$M (Venegas et al. 1996) and purified native *S. marcescens* ChiA and ChiB have Km=40 $\mu$M (Brurberg et al. 1996).

EXAMPLE IX

*P. gallinaceum Chitinases* Have Different pH Activity Profiles and Susceptibility to the Inhibitor Allosamidin. pH activity profiles were determined by microfluorimetry for peaks 1 and 2 of *chitinase* activity and for Endo Lys-C-treated rPgCHT1 (FIG. 10a) (peak 1 contains PgCHT1), using 4-MU GlcNAc$_3$ as substrate. Peak 2 *chitinase* activity had a broad pH optimum of pH 4.0–5.0. Peak 1 *chitinase* activity was optimal at pH 5.0. Similar to peak 1, rPgCHT1 also had a pH optimum of 5.0. This reproducible difference in pH activity profiles suggests that the two peaks of *chitinase* activity are comprised of *chitinases* with different amino acids present in the catalytic sites of the enzymes and thus are products of different genes.

Figure 10B:
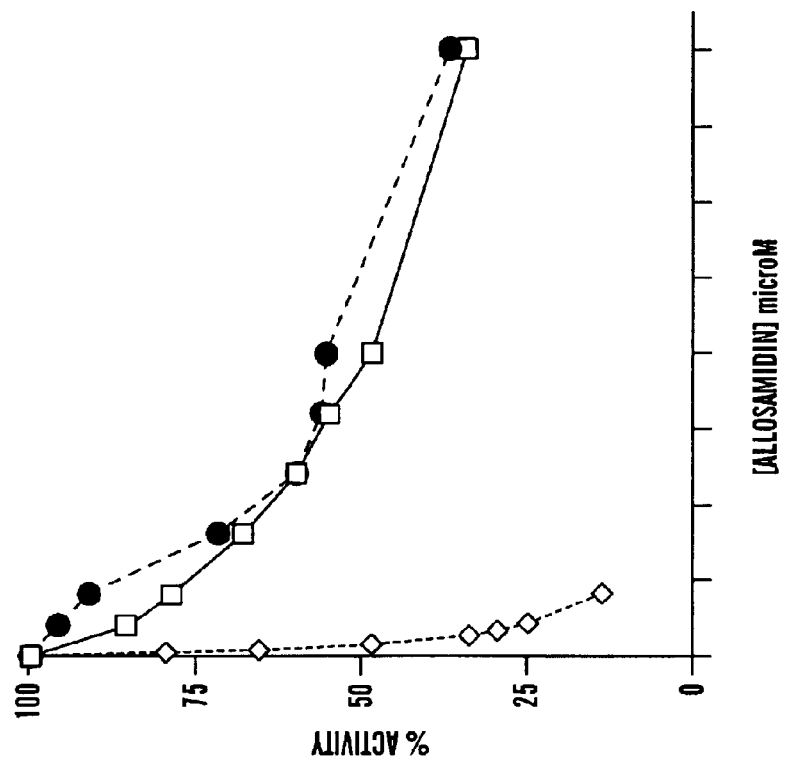
FIGS. 10a and 10b show the analysis of pH activity profile and allosamidin sensitivity of the two peaks of *chitinase* activity chromatographically separated from *P. gallinaceum* ookinete extracts as in FIGS. 6a–6d and Endo Lys-C-activated rPgCHT1-NT1. *Chitinase* activity is expressed as percent activity of enzyme in the absence of inhibitor (as detected with the 4-MU GlcNAc$_3$ substrate). - - - peak 1 of *chitinase* activity; ●, rPgCHT1; ◇, peak 2 of *chitinase* activity. These experiments were repeated two times each with two different preparations of enzyme.
Figure 10A:
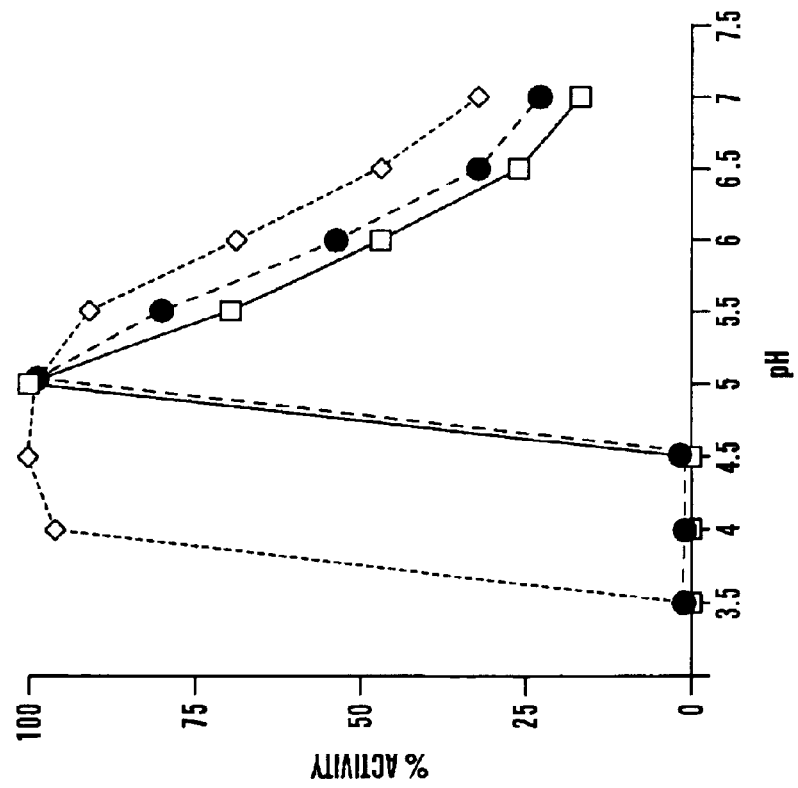

To confirm and extend the suggestion that *P. gallinaceum* ookinetes may secrete at least two *chitinases* derived from different genes, the sensitivity of each of the two peaks of *chitinase* activity and rPgCHT1 to the *chitinase* inhibitor allosamidin was determined (FIG. 10b). The IC$_{50}$ value estimated for peak 1 and rPgCHT1 were similar (7 and 12 $\mu$M, respectively). In contrast, the IC$_{50}$ value for peak 2 was 0.3 $\mu$M, about 30-fold less than that found for peak 1 or rPgCHT1. The allosamidin inhibition data provides additional evidence for a second *P. gallinaceum chitinase* gene and that peak 1 is the product of the PgCHT1 gene. The 1 and 0.1 mM concentrations of allosamidin used in previous studies to block oocyst development (Shahabuddin et al. 1993) far exceed the IC$_{50}$ values for both peaks of *chitinase* activity and would completely inhibit *chitinase* activity in ookinete extracts.

EXAMPLE X

*Plasmodium gallinaceum*. The above Examples report the purification of a 60-kDa *P. gallinaceum* ookinete-secreted *chitinase* and characterize the gene, PgCHT1, encoding it. The experiments presented identify at least two developmentally regulated *chitinases* expressed by *P. gallinaceum* ookinetes. Both are inhibited by allosamidin at concentrations far less than those used in in vivo studies for blocking ookinete penetration of the mosquito peritrophic membrane. Both are secreted and act as *endochitinases*, a property that would be expected of enzymes that allow the ookinete to penetrate and traverse the PM in the mosquito midgut.

At least two *chitinase* activities are separable by HPLC. The first, encoded by the gene, PgCHT1, was identified from peak 1 as a 60-kDa doublet (FIG. 1), which is composed of two forms of the protein, NT1 and NT2, which differ in size by 14 amino acids (FIG. 3). The NT1 form of PgCHT1, expressed as a recombinant protein in *E. coli*, has *chitinase* activity that is increased 73-fold by treatment with Endo Lys-C. The Endo Lys-C cleavage site is between eight and nine amino acid residues downstream from the amino terminus of the NT2 form.

Peak 2 *chitinase* hydrolyzes 4-MU derivatives in a pattern similar to that produced by peak 1 and rPgCHT1. However, peak 2 *chitinase* has a distinct pH activity profile and is about 30-fold more sensitive to allosamidin (FIG. 10b) than rPgCHT1 and native peak 1 *chitinase*. Under reducing and denaturing conditions, a number of proteins, including a 35-kDa protein in peak 2, were identified by Western immunoblotting that increase in expression in parallel with an increased *chitinase* activity (FIGS. 4a–4c and 5a–5e). The 35-kDa protein reacts with antisera prepared from a peptide from the catalytic domain of PgCHT1, but not with antisera from a carboxyl-terminal peptide of PgCHT1. Collectively, the different enzymatic properties and immunological reactivity of the peak 2 *chitinase* support that this *chitinase* is the product of a different gene, PgCHT2. Under non-reducing conditions, peak 2 *chitinase* migrates as a ~210-kDa protein.

An important goal of research on the malaria parasite *chitinases* is to develop novel ways to interrupt malaria transmission. With the cloning of a full-length *P. gallinaceum chitinase* gene, recombinant *chitinase* can be synthesized and tested as a transmission-blocking vaccine in an in vivo avian malaria transmission model.

EXAMPLE XI

Characterization of the Full-Length *P. falciparum Chitinase* Gene, PfCHT1. A partial sequence of PfCHT1 was identified initially in the *P. falciparum* genome project. A 4.2-kb fragment containing the full-length PfCHT1 gene was obtained from screening a phage library of *P. falciparum* genomic DNA. PfCHT1 has a predicted single-exon ORF of 1,134 bp, with a 71.2% A/T content. Sequence translation predicts a protein of 378 aa and an expected molecular mass of 42,792 Da. The 15 bp 5' to the predicted translational initiation site are SEQ ID NO:26: (–15) AATAAATATATAAAC (–1), consistent with sequences reported to flank the translational start sites of yeast, *P. falciparum*, and other protozoa (Yamauchi 1991; Saul and Battistutta 1990; Hamilton et al. 1987). A secretory signal peptide sequence of 28 aa is predicted to be present at the amino terminus (FIG. 11) (Nielsen et al. 1997), which further supports the assignment of the translational initiation codon. In the 400 bp of 90% AT-rich DNA 5' to the predicted start codon, no intron splice sites, exons, or start methionines are identifiable but stop codons are present in all three reading frames. PfCHT1 contains substrate binding and catalytic sites typical of family 18 *chitinases*. Comparison of PfCHT1 with PgCHT1 (FIG. 11) suggests that PfCHT1 lacks a chitin-binding domain. An encoded chitin-binding domain is not detectable within 1,500 bp of sequence downstream of the predicted stop codon within the 4.2-kb genomic clone that contains PfCHT1. In contrast to PgCHT1, PfCHT1 does not contain an amino acid sequence consistent with a proenzyme domain or sequences homologous to the NT1 or NT2 loops found in PgCHT1 (see FIG. 11).

Hybridization of a Southern blot with the same 417-bp digoxigenin-labeled fragment used to screen the genomic phage library demonstrated a single band on genomic DNA digested by five separate restriction enzymes. (FIG. 12a).

This is consistent with a single- or low-copy-number gene. Genomic DNA restricted by BglII yielded one predominant band of 8.2 kb and two smaller, less prominent, bands of 6–6.5 kb of uncertain significance. PfCHT1 has been localized to chromosome 12 (FIG. 12b).

To determine whether stages of *P. falciparum* developing within the mosquito midgut express PfCHT1, total RNA was prepared and analyzed for the presence of PfCHT1 transcript by reverse transcription-PCR (FIG. 12c). At 24 hr postblood meal, a PfCHT1 message was detectable in *P. falciparum*-infected mosquito midguts. Sequencing of the amplicons showed that they were identical to PfCHT1. A PfCHT1 message was not detected in midguts taken from mosquitoes 24 hr after a noninfectious blood meal. These findings demonstrate that *P. falciparum* ookinetes within the mosquito midgut transcribe PfCHT1.

PfCHT1 transcription was examined in cDNA libraries of other *P. falciparum* stages. PfCHT1 and the zygote/ookinete marker Pfs25 were both detected in gametocyte cDNA as well as in two asexual blood-stage cDNA libraries known to contain gametocyte transcripts. These results with Pfs25 are consistent with previous observations, which also noted that Pfs25 protein expression was delayed until after exflagellation and fertilization in the mosquito midgut (Kaslow et al. 1988). Zygotes of *P. gallinaceum* also contain PgCHT1 mRNA but undetectable PgCHT1 protein or *chitinase* enzymatic activity. No PfCHT1 mRNA was detected in a sporozoite cDNA-library (Fidock et al. 1998).

EXAMPLE XII

Figure 13A:
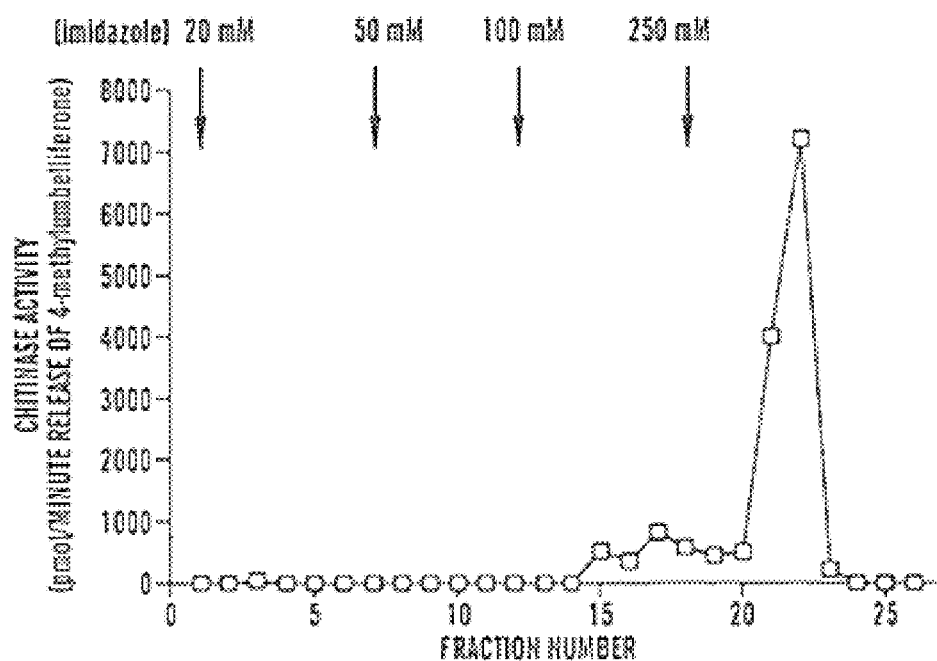
FIGS. 13a–13c show the purification of enzymatically active rPfCHT1.
Figures 13B, 13C:
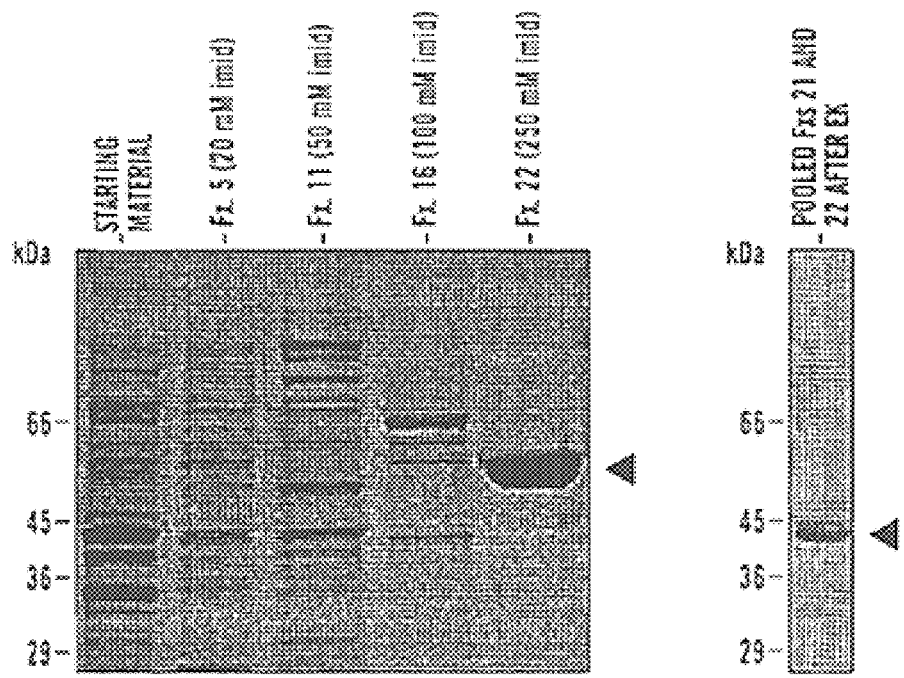

Expression of Enzymatically Active PfCHT1. rPfCHT1 was expressed as a thioredoxin (trx) fusion protein in the expression plasmid pET32b by using as host cells the *E. coli* mutant nonreducing strain AD494, which allows for intracytoplasmic formation of disulfide bonds. The trx-rPfCHT1 fusion protein was constructed with a hexahistidine ($His_6$) tag at both amino and carboxyl termini. The expressed *chitinase* began at the amino acid immediately after the predicted signal peptide cleavage site and included the remainder of the ORF. Chitinase activity was readily found in crude, soluble extracts of induced recombinant bacteria, as detected by hydrolysis of 4MU-chitotrioside. When the same construct was expressed in *E. coli* BL21 cells, *chitinase* activity was not detected, despite a comparable total quantity of recombinant protein produced. Chitinase activity, by the al measures described here, was not detectable in *E. coli* strains AD494 or BL21 transformed with the pET32b vector with no insert. Cell lysates from a 16-liter fermentation of rPfCHT1 were chromatographed with an iimidazole step gradient on a nickel-Sepharose column (FIG. 13a), yielding a trx-rPfCHT1 fusion protein of >95% purity as determined by Coomassie blue staining (FIG. 13b). Western immunoblot and amino-terminal sequencing confirmed the identity of the recombinant protein. The amino-terminal $His_6$ tag was found to be responsible for binding to nickel Sepharose; the carboxyl terminal $His_6$ sequence was found not to bind to nickel Sepharose. Therefore, any *chitinase* activity eluting from the nickel Sepharose column at 250 mM imidazole must have an intact amino-terminal $His_6$ tag, indicating that no unexpected proteolytic degradation of trx-rPfCHT1 had occurred to yield a shorter-length, enzymatically active rPfCHT1. The fused trx sequence was released by treatment with enterokinase, which yielded rPfCHT1 with a molecular mass of 39 kDa (FIG. 13c). The final yield was 7 mg of enterokinase-cleaved rPfCHT1 from a 16 L fermentation run. This 39-kDa protein had robust *chitinase* activity as determined by hydrolysis of 4MU-$GlcNAc_3$. Amino-terminal sequencing of this 39-kDa band gave the amino acid sequence SEQ ID NO:6: ARPGE, the amino terminus of rPfCHT1 as designed in the expression construct. The trx-rPfCHT1 fusion protein and its enterokinase-cleaved product rPfCHT1 had similar enzymatic activity. These experimental results, in conjunction with the comparison of the primary structures of PfCHT1 and PgCHT1 (FIG. 11), strongly suggest that PfCHT1 is not produced as a zymogen. This finding contrasts with previous suggestions that *P. gallinaceum* ookinete-secreted *chitinase* activity is synthesized as a zymogen that is activated by ookinete protease(s) (Shahabuddin et al. 1993; Shahabuddin et al. 1995; Shahabuddin et al. 1996; Shahabuddin 1998).

EXAMPLE XIII

Substrate Specificity of rPfCHT1. rPfCHT1 was found to digest polymeric chitin efficiently in a nondenaturing polyacrylamide activity gel into which glycol chitin had been incorporated. TLC was used to further characterizethe action of rPfCHT1 on native and 4MU-derivatized chitin oligosaccharide substrates (FIGS. 14a–14c). rPfCHT1 had no hydrolytic action on $GlcNAc_2$ or $GlcNAc_3$ but some activity on $GlcNAc_4$. rPfCHT1 had markedly more activity against the longer native chitin oligosaccharide substrates, $GlcNAc_5$ and $GlcNAc_6$ (FIG. 14a). rPfCHT1 did not cleave 4MU-GlcNAc or 4MU-$GlcNAc_2$ substrates, but cleaved the longer substrates (FIG. 14b). 4MU-$GlcNAc_3$ was hydrolyzed at only one glycosidic linkage, yielding 4-MU and $GlcNAc_3$. Cleavage of 4MU-$GlcNAc_3$ was rapid, about three times faster than from 4MU-$GlcNAc_4$, as measured by microfluorimetry (FIG. 14c). The likely reason for the slower release of 4MU from 4MU-$GlcNAc_4$ is that the enzyme also cleaves two other glycosidic bonds, yielding 4MU-GlcNAc and 4MU-$GlcNAc_2$, which cannot be hydrolyzed (FIG. 14b). These data indicate that rPfCHT1 acts as an *endochitinase*, similar to *P. gallinaceum* ookinete-secreted *chitinases*.

Figure 15A:
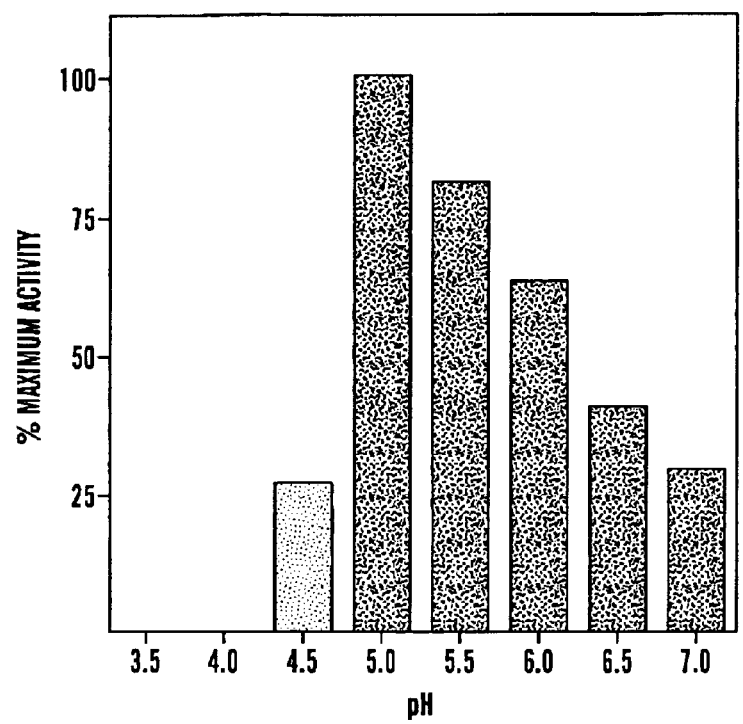
FIGS. 15a–15b show the pH activity profile and pH-dependent inhibition of rPfCHT1 by allosamidin.
Figure 15B:
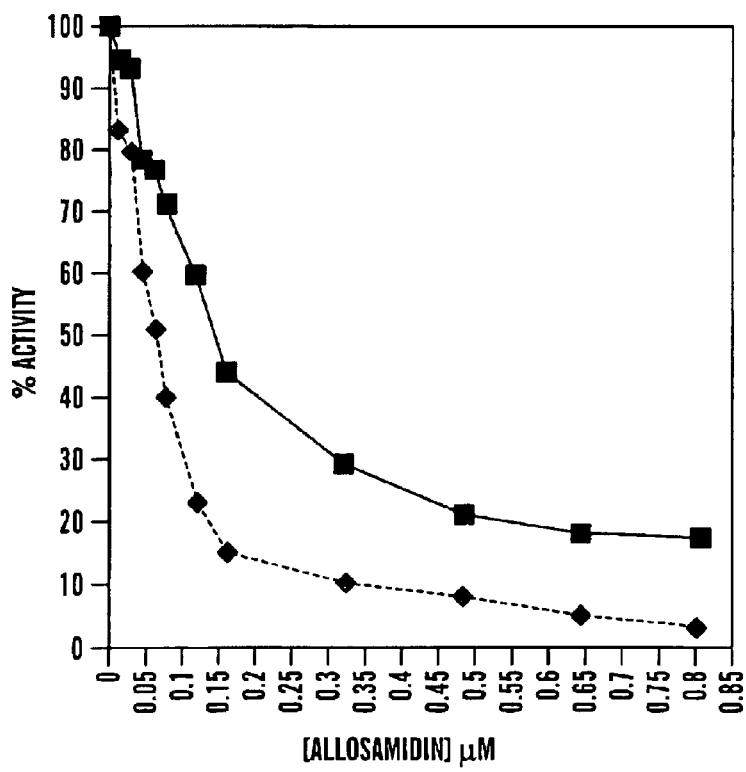

EXAMPLE XIV pH Profile and Allosamidin Sensitivity of rPfCHT1. pH-dependent activity profiles and allosamidin inhibitory concentration curves for rPfCHT1 were determined by microfluorimetry (FIGS. 15a–15b). The sensitivity of rPfCHT1 to allosamidin inhibition increases with rising pH; no difference in the $IC_{50}$ curve is seen above pH 6.0. The $IC_{50}$ of rPfCHT1 to allosamidin is 40 nM, less than that of PgCHT2 (300 nM); both are distinctly different from the $IC_{50}$ of rPgCHT1 (12 $\mu$M). The allosamidin concentration (0.1–1.0 mM) sufficient to block oocyst development in vivo (Shahabuddin et al. 1993) far exceeds the $IC_{50}$ of PfCHT1 (40 nM) for allosamidin in vitro, consistent with the hypothesis that PfCHT1 is involved in allowing the ookinete to penetrate the PM.

EXAMPLE XV

Figure 16:
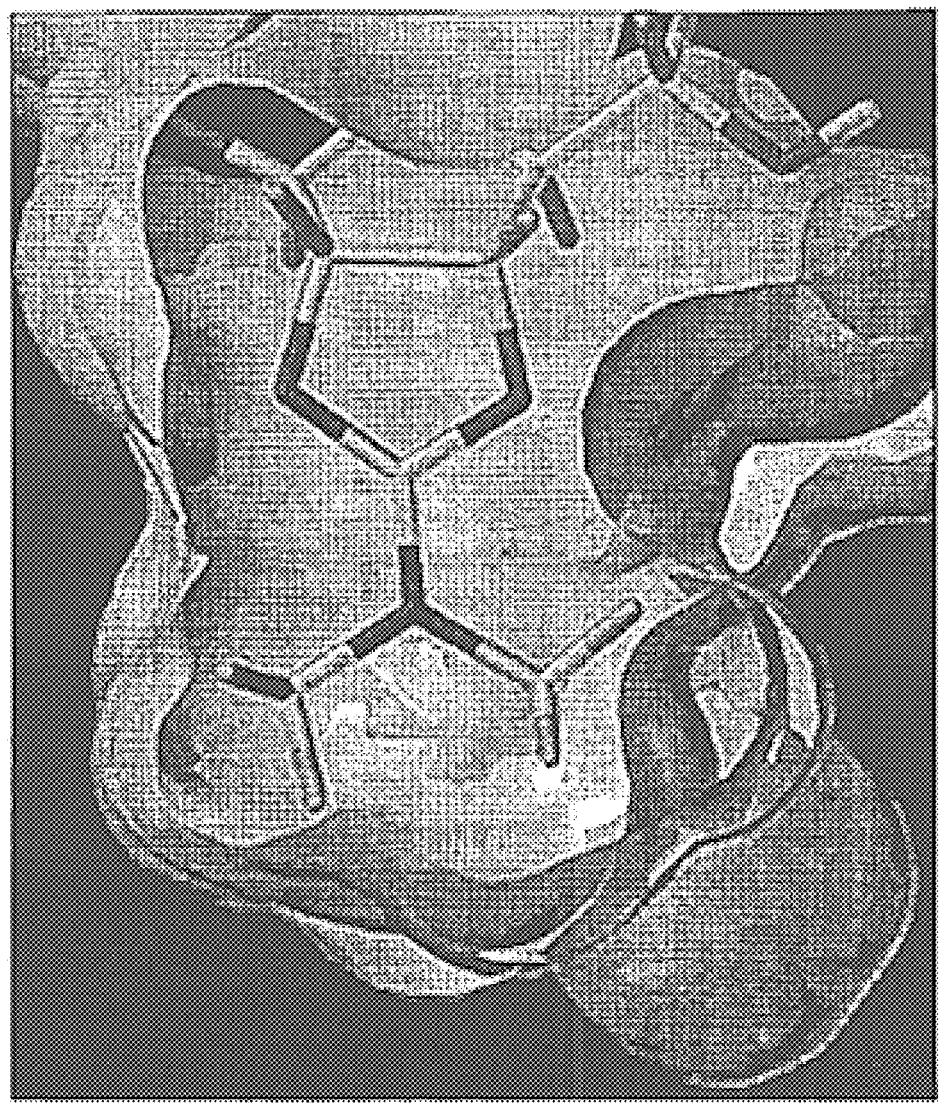
FIG. 16 shows the homology model depicting the overlapping catalytic sites of PfCHT1, PgCHT1, and human chitotriosidase complexed with allosamidin. The three active sites are almost perfectly superimposable, with the exception of a novel pocket found in PgCHT1, seen at lower right. The models were built by using the structure of hevamine complexed with allosamidin as a template.

Molecular Modeling of PfCHT1. PfCHT1 is predicted to have an $(\alpha\beta)_8$ triose isomerase barrel structure typical of family 18 *chitinases* (Terwisscha van Scheltinga et al. 1996). A majority of the active-site residues of PfCHT1 are common to either hevamine or *Serratia marcescens chitinase* ChiA, for which crystal structures are available (Terwisscha van Scheltinga et al. 1996; Perrakis et al. 1994). The *Plasmodium chitinases* are unique in that they have a Gly for Phe/Met (hevamine/ChiA, respectively) change at a position (353 for PfCHT1, 405 for PgCHT1) that is highly conserved among other family 18 *chitinases*. This position is in a critical area at the base of the catalytic site (FIG. 16) and may impart a unique structure. To explore further the potential implication of this position as a site for selective drug targeting, homology models were built for PfCHT1, PgCHT1, and human chitotriosidase (Boot et al. 1995) (FIG. 16). Although the Gly for Phe/Met change substantially enlarges the base of the catalytic pocket in PgCHT1, a complementary $Tyr^{309}$ in PfCHT1 on the β-7 strand compensates for the missing volume, resulting in an almost perfect overlap of the catalytic pocket with that of human chitotriosidase. In contrast, the $I^{361}$ change in the PgCHT1 β7 strand does not fully compensate for the Gly for Phe/Met change. The resulting unique pocket distinguishes PgCHT1 from PfCHT1 and may explain the differential sensitivity of PfCHT1 and PgCHT1 to allosamidin. In the model, allosamidin does not appear to contact $Gly^{405}$ of PgCHT1 but does appear to contact $Tyr^{309}$ in PfCHT1.

EXAMPLE XVI

*Plasmodium falciparum.* The above Examples report that PfCHT1 encodes an *endochitinase*, expressed by parasites within the mosquito midgut, with a marked preference for longer chitin oligosaccharide substrates, consistent with the predicted biological function of this enzyme. This substrate specificity is, to date, unique to *Plasmodium chitinases*.

The data provides evidence that *Plasmodium* ookinetes are likely to secrete products of more than one *chitinase* gene. The pH profile of rPfCHT1 and its sensitivity to allosamidin closely correspond to a second *P. gallinaceum* ookinete-secreted *chitinase* activity that is provisionally called PgCHT2 (see earlier Examples relating to *Plasmodium gallinaceum*). The pH activity profiles of both rPfCHT1 and PgCHT2 are shifted 0.5 pH units toward the acid range compared with both recombinant and native PgCHT1; rPfCHT1 and PgCHT2 also become irreversibly inactivated at 0.5 pH units lower than native and recombinant PgCHT1. rPfCHT1 has a sensitivity to allosamidin much closer to that of PgCHT2 than to PgCHT1. PfCHT1 has other features in common with PgCHT2: its size (molecular mass of secreted protein of 39 kDa vs. 35 kDa for PgCHT2; ookinete-secreted native PgCHT1 has a molecular mass of 55 kDa) and the apparent lack of a chitin-binding domain. It appears that PfCHT1 is the ortholog of PgCHT2.

As a target of blocking malaria parasite transmission to mosquitoes, *chitinase* differs from previously identified surface antigens of sexual stage parasites in that it has a well characterized biochemical activity at which nonimmunological interventions can be aimed. In addition to the traditional transmission-blocking vaccine approach, computational and structural biology-driven rational drug design can be used to identify *chitinase*-inhibitory drugs that block transmission. Such *chitinase* inhibitors which are nontoxic, inexpensive, highly potent, and bioavailable with a long half-life in vivo can be administered widely to human populations in endemic regions. There are precedents for administering pharmacological compounds to human populations in the water or food supplies: fluoridation of water supplies, iodination of salt, diethylcarbamazine in salt (Gelband 1994), and even quinine in tonic water.

Finally, *Plasmodium chitinase* can be used as a target in generating transgenic mosquitoes (Besansky and Collins 1992; Coates et al. 1998; Jasinskiene et al. 1998) that are refractory to ookinete invasion by secreting a *chitinase* inhibitory peptide into the midgut. An oligopeptide *chitinase* inhibitor selective for *P. falciparum chitinase* can be obtained from screening combinatorial phage display libraries as described above. A synthetic gene encoding the peptide under the control of a gut-specific, blood meal-inducible promoter such as that of carboxypeptidase (Tellam et al. 1999) or late trypsin could be used, in an appropriate construct, to transform Anopheles mosquitoes to a refractoriness phenotype.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Bayer, E. A., et al., Meth Enzym 62:308 (1979).
Besansky, N. & Collins, F. (1992) Parasitol. Today 8, 186–192[ISI].
Boot, R., Renkema, G., Strijland, A., Zonneveld, A. & Aerts, J. (1995) J. Biol. Chem. 270, 26252–26256[ISI][Abstract/Full Text].
Brurberg, M., Nes, I., and Eijsink, V. (1996) Microbiology 142, 1581–1589[Abstract]
Campbell, A. M., *Monoclonal Antibody Technology: Laboratory Techniques in Biochemistry and Molecular Biology*, Elsevier Science Publishers, Amsterdam, The Netherlands (1984).
Capecchi, M., Cell 22:479–488 (1980).
Coates, C. J., Jasinskiene, N., Miyashiro, L., and James, A. A. (1998) Proc. Natl. Acad. Sci. U. S. A. 95, 3748–3751 [Abstract/Full Text]
Derman, A., Prinz, W., Belin, D., and Beckwith, J. (1993) Science 262, 1744–1747[Medline]
Duffy, P. & Kaslow, D. (1997) Infect. Immunol. 65, 1109–1113[ISI][Abstract].
Engval, E., et al., Immunol 109:129 (1972).
Fidock, D., Nguyen, T., Dodemont, H., Eling, W. & James, A. (1998) Exp. Parasitol. 89, 125–128[ISI][Medline].
Flach, J., Pilet, P.-E. & Jolles, P. (1992) Experientia 48, 701–716[ISI][Medline].
Fuhrman, J., and Piessens, W. (1985) Mol. Biochem. Parasitol. 17, 93–104[Medline]
Gelband, H. (1994) Am. J. Trop. Med. Hyg. 50, 655–662 [ISI][Medline].
Goding, J. W., J Immunol Meth 13:215 (1976).
Goman, M., Langsley, G., Hyde, J. E., Yankovsky, N. K., Zolg, J. W. & Scaife, J. G. (1982) Mol. Biochem. Parasitol. 5, 391–400[ISI][Medline].
Gozar, M., Price, V. & Kaslow, D. (1998) Infect. Immunol. 66, 59–64[ISI][Abstract/Full Text].
Hamilton, R., Watanabe, C. & A de Boer, H. (1987) Nucleic Acids Res. 15, 3581–3595[ISI][Medline].
Han, L., et al., Proc Natl Acad Sci USA 88:4313–4317 (1991).
Henrissat, B., and Davies, G. (1997) Curr. Opin. Struct. Biol. 7, 637–644[Medline]
Huber, M., Cabib, E., and Miller, L. H. (1991) Proc. Natl. Acad. Sci. U. S. A. 88, 2807–2810[Abstract]
Innis, et al., *PCR Protocols*, Academic Press, San Diego, Calif. (1990).
Jasinskiene, N., Coates, C., Benedict, M., Cornel, A., Rafferty, C., James, A., and Collins, F. (1998) Proc. Natl. Acad. Sci. U. S. A. 95, 3743–3747[Abstract/Full Text]
Kaslow, D. (1993) Curr. Opin. Immunol. 5, 557–565 [Medline]
Kaslow, D. C. (1997) Int. J. Parasitol. 27, 183–189[ISI] [Medline].

Kaslow, D. C., Quakyi, I. A., Syin, C., Raum, M. G., Keister, D. B., Coligan, J. E., McCutchan, T. F. & Miller, L. H. (1988) Nature (London) 333, 74–76 [ISI][Medline]

Kaslow, D. C., and Shiloach, J. (1994) Bio/Technology 12, 494–499

Kaushal, D., and Carter, R. (1984) Mol. Biochem. Parasitol. 11, 145–156[Medline]

Keyhani, N. O., and Roseman, S. (1996) J. Biol. Chem. 271, 33414–33424[Abstract/Full Text]

Klein, T. M., et al., Nature 327:70–73 (1987).

Kozak, M. (1987) Nucleic Acids Res. 15, 8125–8148 [Medline]

Kuranda, M. J., and Robbins, P. W. (1991) J. Biol. Chem. 266, 19758–19767[Abstract]

Lane, W., Galat, A., Harding, M., and Schreiber, S. (1991) J. Protein Chem. 10, 151–160[Medline]

Lutz, et al., Exp Cell Res 175:109–124 (1988).

Mannino, R. J. and Gould-Fogerite, S., BioTechniques 6:682–690 (1988).

Miller, L.K., Bioessays 11:91–95 (1989).

Needleman and Wunsch, J Mol Biol 48:443 (1970).

Ni, X., and Westpheling, J. (1997) Proc. Natl. Acad. Sci. U. S. A. 94, 13116–13121[Full Text]

Nielsen, H., Engelbrecht, J., Brunak, S., and von Heijne, G. (1997) Protein Eng. 10, 1–6

Pearson and Lipman, Proc Natl Acad Sci USA 85:2444 (1988).

Perrakis, A., Tews, I., Dauter, Z., Oppenheim, A., Chet, I., Wilson, K. & Vorgias, C. (1994) Structure 2, 1169–1180 [ISI][Medline].

Perrone, J. & Spielman, A. (1988) Cell Tissue Res. 252, 473–478 [ISI][Medline]

Robbins, P. W., Albright, C., and Benfield, B. (1988) J. Biol. Chem. 263, 443–447[Abstract]

Roberts, R., and Cabib, E. (1982) Anal. Biochem. 127, 402–412 [Medline]

Rossi, J. J., British Medical Bulletin 51(1):217–225 (1995).

Sambrook et al., Molecular Cloning: A Laboratory Manual, 2d Edition, Cold Spring Harbor Laboratory Press, Cold Spring Harbor, N.Y. (1989).

Saul, A. & Battistutta, D. (1990) Mol. Biochem. Parasitol. 42, 55–62[ISI][Medline].

Schlein, Y., Jacobson, R., and Shlomai, J. (1991) Proc. R. Soc. Lond. Ser. B Biol. Sci. 245, 121–126[Medline]

Schlein, Y., Jacobson, R., and Messer, G. (1992) Proc. Natl. Acad. Sci. U. S. A. 89, 9944–9948[Abstract]

Shahabuddin, M. (1998) Parasitology 116,Suppl., S83–S93 [ISI].

Shahabuddin, M., and Kaslow, D. (1993) Parasit. Today 9, 252–255

Shahabuddin, M., Toyoshima, T., Aikawa, M., and Kaslow, D. (1993) Proc. Natl. Acad. Sci. U. S. A. 90, 4266–4270 [Abstract]

Shahabuddin, M., Criscio, M. & Kaslow, D. (1995) Exp. Parasitol. 80, 212–219[ISI][Medline].

Shahabuddin, M., Lemos, F., Kaslow, D. & Jacobs-Lorena, M. (1996) Infect. Immunol. 64, 739–743[ISI][Abstract].

Shakarian, A., and Dwyer, D. (1998) Gene (Amst.) 208, 315–322[Medline]

Shen, Z. & Jacobs-Lorena, M. (1997) J. Biol. Chem. 272, 28895–28900[ISr][Abstract/Full Text].

Shen, Z. & Jacobs-Lorena, M. (1998) J. Biol. Chem. 273, 17665–17670[ISI][Abstract/Full Text].

Shigekawa, K. and Dower, W. J., BioTechniques 6:742–751 (1988).

Sieber, K., Huber, M., Kaslow, D., Banks, S., Torii, M., Aikawa, M. & Miller, L. (1991) Exp. Parasitol. 72, 145–156 [ISI][Medline].

Singhi, L., and Jones, K. (1984) Nucleic Acids Res. 12, 5627–5638[Medline]

Smith and Waterman, Adv Appl Math 2:482 (1981).

Sternberger, L.A., et al., J Histochem Cytochem 18:315 (1970).

St. Groth, et al., J Immunol Methods 35:1–21 (1980).

Su, X. & Wellems, T. (1999) Exp. Parasitol. 91, 367–369 [ISI][Medline].

Tellam, R., Wijffels, G., and Willadsen, P. (1999) Insect Biochem. Mol. Biol. 29, 87–101[Medline]

Templeton, T., Keister, D., Muratova, O., Procter, J. & Kaslow, D. (1998) J. Exp. Med. 187, 1.599–1609[ISI] [Abstract/Full Text].

Terwisscha van Scheltinga, A., Hennig, M. & Dijkstra, B. (1996) J. Mol. Biol. 262, 243–257[Medline].

Venegas, A., Goldstein, J., Beauregard, K., and Oles, A. (1996) Mol. Biochem. Parasitol. 78, 149–159[Medline]

Villagomez-Castro, J., Calvo-Mendez, C., and Lopez-Romero, E. (1992) Mol. Biochem. Parasitol. 52, 53–62 [Medline]

Vinetz, J. & Kaslow, D. (1998) Exp. Parasitol. 90, 199–202 [ISI][Medline].

Yamauchi, K. (1991) Nucleic Acids Res. 19, 2715–2717 [ISI][Medline].

What is claimed is:

1. An isolated and purified nucleic acid molecule as set forth in SEQ ID NO:1.

2. The isolated nucleic acid molecule of claim 1 wherein said nucleic acid is deoxyribonucleic acid.

3. The isolated nucleic acid molecule of claim 1 wherein said nucleic acid is ribonucleic acid.

4. The isolated nucleic acid molecule of claim 3 wherein said ribonucleic acid is mRNA.

5. The isolated nucleic acid molecule of claim 2 wherein said deoxyribonucleic acid is cDNA.

6. The isolated nucleic acid molecule of claim 1 wherein said nucleic acid molecule encodes the amino acid sequence as shown in SEQ ID NO:3.

7. An expression vector comprising the nucleic acid molecule of claim 1.

8. The expression vector of claim 5 wherein the expression vector is selected from the group consisting of a plasmid and a virus.

9. An isolated host cell comprising the expression vector of claim 7.

* * * * *

SEQUENCE LISTING

```
<160> NUMBER OF SEQ ID NOS: 26

<210> SEQ ID NO 1
<211> LENGTH: 1137
<212> TYPE: DNA
<213> ORGANISM: Plasmodium falciparum

<400> SEQUENCE: 1
atgaatttta ccgtaaaata ctctttcctg gttatttgtc tgctgtgctg cctgctgtct      60
acttatgttt ctgttatcga aggtcatcgt gctcgtccgg gtgaatcccg caaaaacccg     120
cgtgaaatta tcaaaacgtt taaagaatcc ggtaaaggta tcatccaggg ttactatccg     180
tcctgggtga gctataatca caacctgaag gacctgaacc cgaacctgaa cgtggttcac     240
```

-continued

| | |
|---|---|
| atgagctttg ctaaaatgga tttaagctac gactccattg aatccatcgt aggtagcccg | 300 |
| ctgctgttta aaagcctgat tggcctggag tatattggtc tgaatgagta cttcaatgat | 360 |
| gccatgaatc tgcgcaaagc tcgtccggac attattatgc tgctgagcct gggcggtgag | 420 |
| acctaccatc cgtcctcctt cgattctgca ctcaacgcgg ttgaaaaaat cgcaaatctg | 480 |
| gtggatgaac tgggcttcga tggtattgat gtagattacg aaccgaacgg cagctttgat | 540 |
| ggtctgaatg ataaagaaaa agcggacttc tttgtacaat acgtgaccaa actgcgcgaa | 600 |
| tacatgtgtg atgataaact gatcagcatc agccagtcct ctaatggcgc tctgagctgc | 660 |
| atcggtttca acgacccgaa aaaaatctgt atggatgacg aagctccgta taacagcaaa | 720 |
| tatttcaaca aaccggacgt taagaaagaa ctgttacgcg cagcccagat ggcatctgcg | 780 |
| ggtggtgcca tctacctgat gaacaacctg aaagatatga ttgacatggt gtttgtgcag | 840 |
| acgttcaact acacgaactc taccgattct accgttatga agaattata cgactcctac | 900 |
| gcatactatg taaaagta cgattacgtg atcatcatgg gcttcaccct gatgttcccg | 960 |
| tccacgccgt tcaacccgaa cgataaaatg ctggtaaaat ctatcggcga tttcgtaaaa | 1020 |
| actgaaaaca aactgaataa acgcgcagat ggtttcggcc tgtggtctct gtccagcgac | 1080 |
| aacgcggccc ataatgaaca gctggcgatc gagtacttcg ttgaaagcct gcactaa | 1137 |

<210> SEQ ID NO 2
<211> LENGTH: 1764
<212> TYPE: DNA
<213> ORGANISM: Plasmodium gallinaceum

<400> SEQUENCE: 2

| | |
|---|---|
| atgaatttta aaatatcaat attttttaatt atagtatcca tcttgtattc tgcaaattcc | 60 |
| agaaccttga aggaaaaaa taatataaat aattcattgg gaataatacg ggaaaataaa | 120 |
| aataaaactc atcaaacgga aatacatgag tcttttttcac atcttaaatc gaataatagt | 180 |
| aattttgtag aatatggatc ttattgcgga gatgggtgta actctagaat tacaaaaaat | 240 |
| aataaaaata taaataaaaa tgatagaaaa tcaccaagac aaattttaga ggagtataaa | 300 |
| aaaaggaaac aaggtattat agcaggatac tatggttcat ggaacagtca aggtgataga | 360 |
| gcaaaacata tgattgattc aaacccaatg gtgtcaattt tatatattgc atttgctcgc | 420 |
| attaatatgt tatatgatgt atctagacca tttaatggaa gacaaagatt cctattaaga | 480 |
| aaacacggct tagaatatga aacctatggt atgatgctta atgaaattag acgtatcaga | 540 |
| aaagtacgtc cagatgtaat tattcttttta tccttaggtg gagaaaccta tatgatagat | 600 |
| atagaaaaag aaattgatta tgtggataaa atattgaagc ttgttaatga ttttgattta | 660 |
| gatggtgtag atattgactg ggaaccacat gggaagtttt acaacttaaa tgaattaaat | 720 |
| ttttcaaatt attatattaa attaattaac ttgttaagaa aaactattcc ggaagaaaag | 780 |
| ttaatttcaa tttctggttc atcaaatgct gcattatcat gcgtttcagg agttgcatct | 840 |
| ttctgtaaag atgaagaatc tccatataac actaaatttt tgtctgaaca aatagaaaca | 900 |
| aataagaat tacataggcc agcagcgatg ttatcagcag aactttat taatattttt | 960 |
| aatacagcaa aggagaaaat agatcttgta tttattcaaa catacaattt agaaactaca | 1020 |
| aatccagata taatggtaga tatgtactta tcccatttat attttggttt aaaatataac | 1080 |
| atcacaatca tattaggttt ttcattagaa cataacagag gtggatttag tcccgaaaat | 1140 |
| aaagaattat tagaattggt aggaaaaaca atacatgata aaaatcaaaa taataatagg | 1200 |
| gcagatggta tagggatatg gcatttattt atgaaagaac aattaccaac tggatcattc | 1260 |

-continued

```
gatgtagata ttttcttac aaatatttgg aaacatttaa atcctgaagt acaaactcca    1320 aaagaccta ctataactga aaaccctgaa gactgtagca caatagatga atatgttcca    1380
ggactcgtta ttccaaccat agggatatat acaaaacaca atgatgctat atggaaaact    1440
agatcttatt caattcatgc acctggtgta gacagatatg aatgggactt ggtcaaagta    1500
tgctatgaaa aaatatgcga tgggaaagca gcccattatt ataacactga ctataaagaa    1560
agctctatta ttatatggaa aggggaacca tatttaatta atggtggca acaaggacct     1620 ccggaaggtc aggcactaga gtcatacaca aaactagatg catccaaatg tccagggata    1680
gaagaatgga ataaaaaata tccacataaa ccactagaag taggaaca atatgaacaa     1740 gaagtggatt taccattaca ataa                                          1764
```

<210> SEQ ID NO 3
<211> LENGTH: 378
<212> TYPE: PRT
<213> ORGANISM: Plasmodium falciparum

<400> SEQUENCE: 3

```
Met Asn Phe Thr Val Lys Tyr Ser Phe Leu Val Ile Cys Leu Leu Cys
  1               5                  10                  15

Cys Leu Leu Ser Thr Tyr Val Ser Val Ile Glu Gly His Arg Ala Arg
                 20                  25                  30

Pro Gly Glu Ser Arg Lys Asn Pro Arg Glu Ile Ile Lys Thr Phe Lys
             35                  40                  45

Glu Ser Gly Lys Gly Ile Ile Gln Gly Tyr Tyr Pro Ser Trp Val Ser
         50                  55                  60

Tyr Asn His Asn Leu Lys Asp Leu Asn Pro Asn Leu Asn Val Val His
  65                  70                  75                  80

Met Ser Phe Ala Lys Met Asp Leu Ser Tyr Asp Ser Ile Glu Ser Ile
                 85                  90                  95

Val Gly Ser Pro Leu Leu Phe Lys Ser Leu Ile Gly Leu Glu Tyr Ile
            100                 105                 110

Gly Leu Asn Glu Tyr Phe Asn Asp Ala Met Asn Leu Arg Lys Ala Arg
        115                 120                 125

Pro Asp Ile Ile Met Leu Leu Ser Leu Gly Gly Glu Thr Tyr His Pro
    130                 135                 140

Ser Ser Phe Asp Ser Ala Leu Asn Ala Val Glu Lys Ile Ala Asn Leu
145                 150                 155                 160

Val Asp Glu Leu Gly Phe Asp Gly Ile Asp Val Asp Tyr Glu Pro Asn
                165                 170                 175

Gly Ser Phe Asp Gly Leu Asn Asp Lys Glu Lys Ala Asp Phe Phe Val
            180                 185                 190

Gln Tyr Val Thr Lys Leu Arg Glu Tyr Met Cys Asp Asp Lys Leu Ile
        195                 200                 205

Ser Ile Ser Gln Ser Ser Asn Gly Ala Leu Ser Cys Ile Gly Phe Asn
    210                 215                 220

Asp Pro Lys Lys Ile Cys Met Asp Glu Ala Pro Tyr Asn Ser Lys
225                 230                 235                 240

Tyr Phe Asn Lys Pro Asp Val Lys Lys Glu Leu Leu Arg Ala Ala Gln
                245                 250                 255

Met Ala Ser Ala Gly Gly Ala Ile Tyr Leu Met Asn Asn Leu Lys Asp
            260                 265                 270

Met Ile Asp Met Val Phe Val Gln Thr Phe Asn Tyr Thr Asn Ser Thr
```

```
                        275                 280                 285
Asp Ser Thr Val Met Lys Glu Leu Tyr Asp Ser Tyr Ala Tyr Tyr Gly
    290                 295                 300

Lys Lys Tyr Asp Tyr Val Ile Ile Met Gly Phe Thr Leu Met Phe Pro
305                 310                 315                 320

Ser Thr Pro Phe Asn Pro Asn Asp Lys Met Leu Val Lys Ser Ile Gly
                325                 330                 335

Asp Phe Val Lys Thr Glu Asn Lys Leu Asn Lys Arg Ala Asp Gly Phe
            340                 345                 350

Gly Leu Trp Ser Leu Ser Ser Asp Asn Ala Ala His Asn Glu Gln Leu
        355                 360                 365

Ala Ile Glu Tyr Phe Val Glu Ser Leu His
    370                 375

<210> SEQ ID NO 4
<211> LENGTH: 587
<212> TYPE: PRT
<213> ORGANISM: Plasmodium gallinaceum

<400> SEQUENCE: 4

Met Asn Phe Lys Ile Ser Ile Phe Leu Ile Ile Val Ser Ile Leu Tyr
  1               5                  10                  15

Ser Ala Asn Ser Arg Thr Leu Lys Gly Lys Asn Asn Ile Asn Asn Ser
                20                  25                  30

Leu Gly Ile Ile Arg Glu Asn Lys Asn Lys Thr His Gln Thr Glu Ile
            35                  40                  45

His Glu Ser Phe Ser His Leu Lys Ser Asn Asn Ser Asn Phe Val Glu
        50                  55                  60

Tyr Gly Ser Tyr Cys Gly Asp Gly Cys Asn Ser Arg Ile Thr Lys Asn
 65                  70                  75                  80

Asn Lys Asn Ile Asn Lys Asn Asp Arg Lys Ser Pro Arg Gln Ile Leu
                85                  90                  95

Glu Glu Tyr Lys Lys Arg Lys Gln Gly Ile Ile Ala Gly Tyr Tyr Gly
                100                 105                 110

Ser Trp Asn Ser Gln Gly Asp Arg Ala Lys His Met Ile Asp Ser Asn
            115                 120                 125

Pro Met Val Ser Ile Leu Tyr Ile Ala Phe Ala Arg Ile Asn Met Leu
        130                 135                 140

Tyr Asp Val Ser Arg Pro Phe Asn Gly Arg Gln Arg Phe Leu Leu Arg
145                 150                 155                 160

Lys His Gly Leu Glu Tyr Glu Thr Tyr Gly Met Met Leu Asn Glu Ile
                165                 170                 175

Arg Arg Ile Arg Lys Val Arg Pro Asp Val Ile Leu Leu Ser Leu
            180                 185                 190

Gly Gly Glu Thr Tyr Met Ile Asp Ile Glu Lys Glu Ile Asp Tyr Val
        195                 200                 205

Asp Lys Ile Leu Lys Leu Val Asn Asp Phe Asp Leu Asp Gly Val Asp
    210                 215                 220

Ile Asp Trp Glu Pro His Gly Lys Phe Tyr Asn Leu Asn Glu Leu Asn
225                 230                 235                 240

Phe Ser Asn Tyr Tyr Ile Lys Leu Ile Asn Leu Leu Arg Lys Thr Ile
                245                 250                 255

Pro Glu Glu Lys Leu Ile Ser Ile Ser Gly Ser Ser Asn Ala Ala Leu
            260                 265                 270
```

-continued

```
Ser Cys Val Ser Gly Val Ala Ser Phe Cys Lys Asp Glu Glu Ser Pro
        275                 280                 285
Tyr Asn Thr Lys Phe Leu Ser Glu Gln Ile Glu Thr Asn Lys Glu Leu
        290                 295                 300
His Arg Ala Ala Ala Met Leu Ser Ala Gly Thr Phe Ile Asn Ile Phe
305                 310                 315                 320
Asn Thr Ala Lys Glu Lys Ile Asp Leu Val Phe Ile Gln Thr Tyr Asn
                325                 330                 335
Leu Glu Thr Thr Asn Pro Asp Ile Met Val Asp Met Tyr Leu Ser His
            340                 345                 350
Leu Tyr Phe Gly Leu Lys Tyr Asn Ile Thr Ile Ile Leu Gly Phe Ser
        355                 360                 365
Leu Glu His Asn Arg Gly Gly Phe Ser Pro Glu Asn Lys Glu Leu Leu
370                 375                 380
Glu Leu Val Gly Lys Thr Ile His Asp Lys Asn Gln Asn Asn Asn Arg
385                 390                 395                 400
Ala Asp Gly Ile Gly Ile Trp His Leu Phe Met Lys Glu Gln Leu Pro
                405                 410                 415
Thr Gly Ser Phe Asp Val Asp Ile Phe Leu Thr Asn Ile Trp Lys His
            420                 425                 430
Leu Asn Pro Glu Val Gln Thr Pro Lys Asp Leu Thr Ile Thr Glu Asn
        435                 440                 445
Pro Glu Asp Cys Ser Thr Ile Asp Glu Tyr Val Pro Gly Leu Val Ile
450                 455                 460
Pro Thr Ile Gly Ile Tyr Tyr Lys His Asn Asp Ala Ile Trp Lys Thr
465                 470                 475                 480
Arg Ser Tyr Ser Ile His Ala Pro Gly Val Asp Arg Tyr Glu Trp Asp
                485                 490                 495
Leu Val Lys Val Cys Tyr Glu Lys Ile Cys Asp Gly Lys Ala Ala His
            500                 505                 510
Tyr Tyr Asn Thr Asp Tyr Lys Glu Ser Ser Ile Ile Ile Trp Lys Gly
        515                 520                 525
Glu Pro Tyr Leu Ile Lys Trp Trp Gln Gln Gly Pro Pro Glu Gly Gln
530                 535                 540
Ala Leu Glu Ser Tyr Thr Lys Leu Asp Ala Ser Lys Cys Pro Gly Ile
545                 550                 555                 560
Glu Glu Trp Asn Lys Lys Tyr Pro His Lys Pro Leu Glu Val Glu Glu
                565                 570                 575
Gln Tyr Glu Gln Glu Val Asp Leu Pro Leu Gln
            580                 585
```

<210> SEQ ID NO 5
<211> LENGTH: 2500
<212> TYPE: DNA
<213> ORGANISM: Plasmodium gallinaceum

<400> SEQUENCE: 5

```
ccctacggct gcgagaagac gacagaaggg gaaatatttt ttattttata gttttttgt      60
acttttaat  tttttttcaa agcttacatt atctgttttt ttttaatcat ttttctgtt     120
tttttgtttt tttgttcttt tgttcttttg ttcttttgtt cttttctttt agcttccat    180
aattcttttc caattttttt gtttaatttg tttgtgcttg tatgttatct taatattacc    240
atttcaatta tagtagtata taattttata gaaaatgaa  ttttaaaata tcaatatttt    300
taattatagt atccatcttg tattctgcaa attccagaac cttgaaagga aaaaataata    360
```

-continued

```
taaataattc attgggaata atacgggaaa ataaaaataa aactcatcaa acggaaatac      420
atgagtcttt ttcacatctt aaatcgaata atagtaattt tgtagaatat ggatcttatt      480
gcggagatgg gtgtaactct agaattacaa aaaataataa aaatataaat aaaaatgata      540
gaaaatcacc aagacaaatt ttagaggagt ataaaaaaag gaaacaaggt attatagcag      600
gatactatgg ttcatggaac agtcaaggtg atagagcaaa acatatgatt gattcaaacc      660
caatggtgtc aattttatat attgcatttg ctcgcattaa tatgttatat gatgtatcta      720
gaccatttaa tggaagacaa agattcctat taagaaaaca cggcttagaa tatgaaacct      780
atggtatgat gcttaatgaa attagacgta tcagaaaagt acgtccagat gtaattattc      840
ttttatcctt aggtggagaa acctatatga tagatataga aaaagaaatt gattatgtgg      900
ataaaatatt gaagcttgtt aatgattttg atttagatgg tgtagatatt gactgggaac      960
cacatgggaa gttttacaac ttaaatgaat taaattttc aaattattat attaaattaa     1020
ttaacttgtt aagaaaaact attccggaag aaaagttaat ttcaatttct ggttcatcaa     1080
atgctgcatt atcatgcgtt tcaggagttg catctttctg taaagatgaa gaatctccat     1140
ataacactaa atttttgtct gaacaaatag aaacaaataa agaattacat agggcagcag     1200
cgatgttatc agcaggaact tttattaata ttttttaatac agcaaaggag aaaatagatc     1260
ttgtatttat tcaaacatac aatttagaaa ctacaaatcc agatataatg gtagatatgt     1320
acttatccca tttatatttt ggtttaaaat ataacatcac aatcatatta ggttttttcat     1380
tagaacataa cagaggtgga tttagtcccg aaaataaaga attattagaa ttggtaggaa     1440
aaacaataca tgataaaaat caaaataata ataggggcaga tggtataggg atatggcatt     1500
tatttatgaa agaacaatta ccaactggat cattcgatgt agatattttt cttacaaata     1560
tttggaaaca tttaaatcct gaagtacaaa ctccaaaaga ccttactata actgaaaacc     1620
ctgaagactg tagcacaata gatgaatatg ttccaggact cgttattcca accatagga     1680
tatattacaa acacaatgat gctatatgga aaactagatc ttattcaatt catgcacctg     1740
gtgtagacag atatgaatgg gacttggtca agtatgcta tgaaaaaata tgcgatggga     1800
aagcagccca ttattataac actgactata agaaagctc tattattata tggaaagggg     1860
aaccatatt aattaaatgg tgcaacaag gacctccgga aggtcaggca ctagagtcat     1920
acacaaaact agatgcatcc aaatgtccag ggatagaaga atggaataaa aaatatccac     1980
ataaaccact agaagtagag gaacaatatg aacaagaagt ggatttacca ttacaataaa     2040
tgaggctttt tattaaaaat attaaagaa tatttcatag aaaaatgtag taattagtac     2100
aaatatacaa aaataataaa gtaaataaa catattacca tggtaaaata agataaatta     2160
tatttttttt attcttttta caaagaaaaa tatgcatttc tttaaatttt ttttgtaaa     2220
attagatgtt ataatttcta atactgttt aagaacagca aagtttcgaa aaacttgaat     2280
tttaaaaat aaaatatttt taatatttg caatttttt tatatttatg ttattaagaa     2340
ttcaatttt ttttgtgttt ttttatat atatttgaaa gaaaactta atatagagat     2400
aaaactgcma cagtaaatag ctaattataa agtttatgca ataatattaa aaataatata     2460
tttaaaaaaa ggaaaaaaaa aaaaaaaaa aaaaaaaaa                           2500
```

<210> SEQ ID NO 6
<211> LENGTH: 5
<212> TYPE: PRT
<213> ORGANISM: Plasmodium falciparum

```
<400> SEQUENCE: 6

Ala Arg Pro Gly Glu
 1               5

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: synthetic
      primer sequence
<221> NAME/KEY: modified_base
<222> LOCATION: (18)
<223> OTHER INFORMATION: i

<400> SEQUENCE: 7
caytaytaya ayaayacnga ytayaaa                                           27

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: synthetic
      primer sequence
<221> NAME/KEY: modified_base
<222> LOCATION: (6)
<223> OTHER INFORMATION: i
<221> NAME/KEY: modified_base
<222> LOCATION: (18)
<223> OTHER INFORMATION: i
<221> NAME/KEY: modified_base
<222> LOCATION: (21)
<223> OTHER INFORMATION: i

<400> SEQUENCE: 8
aayccngarg thcaracncc naaa                                              24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: synthetic
      primer sequence
<221> NAME/KEY: modified_base
<222> LOCATION: (9)
<223> OTHER INFORMATION: i
<221> NAME/KEY: modified_base
<222> LOCATION: (12)
<223> OTHER INFORMATION: i
<221> NAME/KEY: modified_base
<222> LOCATION: (15)
<223> OTHER INFORMATION: i

<400> SEQUENCE: 9
cayaarccny tngargtnga rgarc                                             25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 10
gggttttcag ttatagtaag gtc                                               23
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 11
aagcagtggt aacaacgcag agt                                          23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 12
gaaaaaatat gcgatgggaa agca                                         24

<210> SEQ ID NO 13
<211> LENGTH: 7
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 13 acgacgt                                                             7

<210> SEQ ID NO 14
<211> LENGTH: 42
<212> TYPE: DNA
<213> ORGANISM: Plasmodium gallinaceum
<220> FEATURE:
<223> OTHER INFORMATION: catalytic active site

<400> SEQUENCE: 14
taatgatttt gatttagatg gtgtagatat tgactgggaa cc                     42

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 15
gcgccatggg ttacggtagc tattgtggcg                                   30

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 16
gcgctcgagt tgcagcggca ggtccac                                      27

<210> SEQ ID NO 17
<211> LENGTH: 14

-continued

```
<212> TYPE: PRT
<213> ORGANISM: Plasmodium gallinaceum
<220> FEATURE:
<223> OTHER INFORMATION: active site

<400> SEQUENCE: 17

Asp Leu Asp Gly Val Asp Ile Asp Trp Glu Pro His Gly Lys
 1               5                  10

<210> SEQ ID NO 18
<211> LENGTH: 15
<212> TYPE: PRT
<213> ORGANISM: Plasmodium gallinaceum
<220> FEATURE:
<223> OTHER INFORMATION: carboxyl terminus

<400> SEQUENCE: 18

Cys Asp Gly Lys Ala Ala His Tyr Tyr Asn Thr Asp Tyr Lys Glu
 1               5                  10                  15

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 19
gcgccatggg tcatcgagca cgaccaggtg aa                                32

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 20
cgcgctcgag atgtaaagat tctacgaaat attc                              34

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 21
attatgcttt tatctcttgg agg                                          23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 22
agtctttaca aaatcaccaa tgg                                          23

<210> SEQ ID NO 23
<211> LENGTH: 23
<212> TYPE: DNA
```

```
<213> ORGANISM: Artificial Sequence
<220> FEATURE:
<223> OTHER INFORMATION: Description of Artificial Sequence: synthetic
      primer sequence

<400> SEQUENCE: 23
cataacgttg aataaggctc ggg                                          23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: synthetic
      primer sequence

<400> SEQUENCE: 24
ctatatgatg tatcagcctg gtcc                                         24

<210> SEQ ID NO 25
<211> LENGTH: 7
<212> TYPE: PRT
<213> ORGANISM: Plasmodium falciparum
<220> FEATURE:
<223> OTHER INFORMATION: consensus sequence of substrate-binding site

<400> SEQUENCE: 25

Xaa Xaa Xaa Ser Xaa Gly Gly
  1               5

<210> SEQ ID NO 26
<211> LENGTH: 15
<212> TYPE: DNA
<213> ORGANISM: Plasmodium falciparum

<400> SEQUENCE: 26
aataaatata taaac                                                   15
```